US 10,851,094 B2

(12) United States Patent
Sato

(10) Patent No.: US 10,851,094 B2
(45) Date of Patent: Dec. 1, 2020

(54) 2-SUBSTITUTED BENZOTHIAZOLYL-3-SUBSTITUTED PHENYL-5-SUBSTITUTED SULFONATED PHENYL-2H-TETRAZOLIUM SALT, REAGENT FOR BIOLOGICAL COMPONENT CONCENTRATION MEASUREMENT CONTAINING SAID SALT, AND BIOLOGICAL COMPONENT CONCENTRATION MEASUREMENT METHOD USING SAID SALT

(71) Applicant: TERUMO KABUSHIKI KAISHA, Tokyo (JP)

(72) Inventor: Hiroya Sato, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 155 days.

(21) Appl. No.: 16/255,535

(22) Filed: Jan. 23, 2019

(65) Prior Publication Data

US 2019/0185465 A1 Jun. 20, 2019

Related U.S. Application Data

(63) Continuation of application No. PCT/JP2017/031677, filed on Sep. 1, 2017.

(30) Foreign Application Priority Data

Sep. 14, 2016 (JP) .................................. 2016-179911

(51) Int. Cl.
| | | |
|---|---|---|
| *C07D 417/04* | (2006.01) | |
| *C12Q 1/26* | (2006.01) | |
| *G01N 33/66* | (2006.01) | |
| *G01N 33/92* | (2006.01) | |
| *C12Q 1/32* | (2006.01) | |
| *C12Q 1/60* | (2006.01) | |
| *C12Q 1/54* | (2006.01) | |
| *C12Q 1/62* | (2006.01) | |
| *C07D 513/04* | (2006.01) | |

(52) U.S. Cl.
CPC ......... *C07D 417/04* (2013.01); *C07D 513/04* (2013.01); *C12Q 1/26* (2013.01); *C12Q 1/32* (2013.01); *C12Q 1/54* (2013.01); *C12Q 1/60* (2013.01); *C12Q 1/62* (2013.01); *G01N 33/66* (2013.01); *G01N 33/92* (2013.01)

(58) Field of Classification Search
CPC ...... C07D 417/04; C07D 513/04; C12Q 1/26; C12Q 1/32; C12Q 1/54; C12Q 1/60; C12Q 1/62; G01N 33/92
See application file for complete search history.

(56) References Cited

U.S. PATENT DOCUMENTS

| 5,250,695 | A | 10/1993 | Blatt et al. |
| 7,767,822 | B2 | 8/2010 | Albarella et al. |
| 2007/0111274 | A1 | 5/2007 | Fukuoka |

FOREIGN PATENT DOCUMENTS

| CN | 105418526 A | 3/2016 |
| EP | 0 476 457 A2 | 3/1992 |
| JP | S60-75470 A | 4/1985 |
| JP | S61-84 A | 1/1986 |
| JP | H04-270278 A | 9/1992 |
| JP | H04-288076 A | 10/1992 |
| JP | H04-321685 A | 11/1992 |
| JP | H04-340466 A | 11/1992 |
| JP | H06-107644 A | 4/1994 |
| JP | H08-53444 A | 2/1996 |
| JP | H11-193266 A | 7/1999 |
| JP | 2008-526990 A | 7/2008 |
| JP | 2008197077 A | * 8/2008 |

OTHER PUBLICATIONS

Machine translation of JP-2008197077, published 2008,—A downloaded from Espacenet on Aug. 17, 2020 (Year: 2008).*

(Continued)

*Primary Examiner* — Susan M Hanley
(74) *Attorney, Agent, or Firm* — Foley & Lardner LLP

(57) ABSTRACT

A 2-substituted benzothiazolyl-3-substituted phenyl-5-substituted sulfonated phenyl-2H-tetrazolium salt represented by the following Formula (1):

[Chemical Formula 1]

$$(SO_3^-)_m \overset{R^1}{\underset{}{\text{—}}} \overset{(R^2)_n}{\underset{}{\text{—}}} (SO_3^-)_p \quad (X^+)_{m+p-1}$$

(with benzothiazole ring bearing $(OR^3)_q$)

wherein, $R^1$ can be a hydrogen atom, a hydroxyl group, a methoxy group, and an ethoxy group; $R^2$ can be a nitro group, $-OR^4$, and a carboxyl group; $R^3$ is a hydrogen atom, a methyl group, or an ethyl group, while at least one is a methyl group or an ethyl group; $R^4$ is a methyl group or an ethyl group; m is 1 or 2; n is an integer from 0 to 2; p is 0 or 1; n+p is 1 or greater; q is 1 or 2; when q is 2, the $OR^3$'s are disposed adjacently to each other and may form a ring; and X is a hydrogen atom or an alkali metal atom.

17 Claims, 17 Drawing Sheets

(56) References Cited

OTHER PUBLICATIONS

Translation of the Written Opinion of the International Searching Authority dated Nov. 7, 2017 in corresponding application No. PCT/JP2017/031677.
Extended European Search Report dated Jan. 20, 2020 for corresponding European Patent Application No. 17850725.7.
Munetaka Ishiyama et al: "A New Sulfonated Tetrazolium Salt That Produces a Highly Water-Soluble Formazan Dye", Chemical and Pharmaceutical Bulletin, Jun. 15, 1993 (Jun. 15, 1993), pp. 1118-1122.
International Searching Authority, "International Search Report," issued in connection with International Patent Application No. PCT/JP2017/031677, dated Nov. 7, 2017.
International Searching Authority, "Written Opinion," issued in connection with International Patent Application No. PCT/JP2017/031677, dated Nov. 7, 2017.

\* cited by examiner

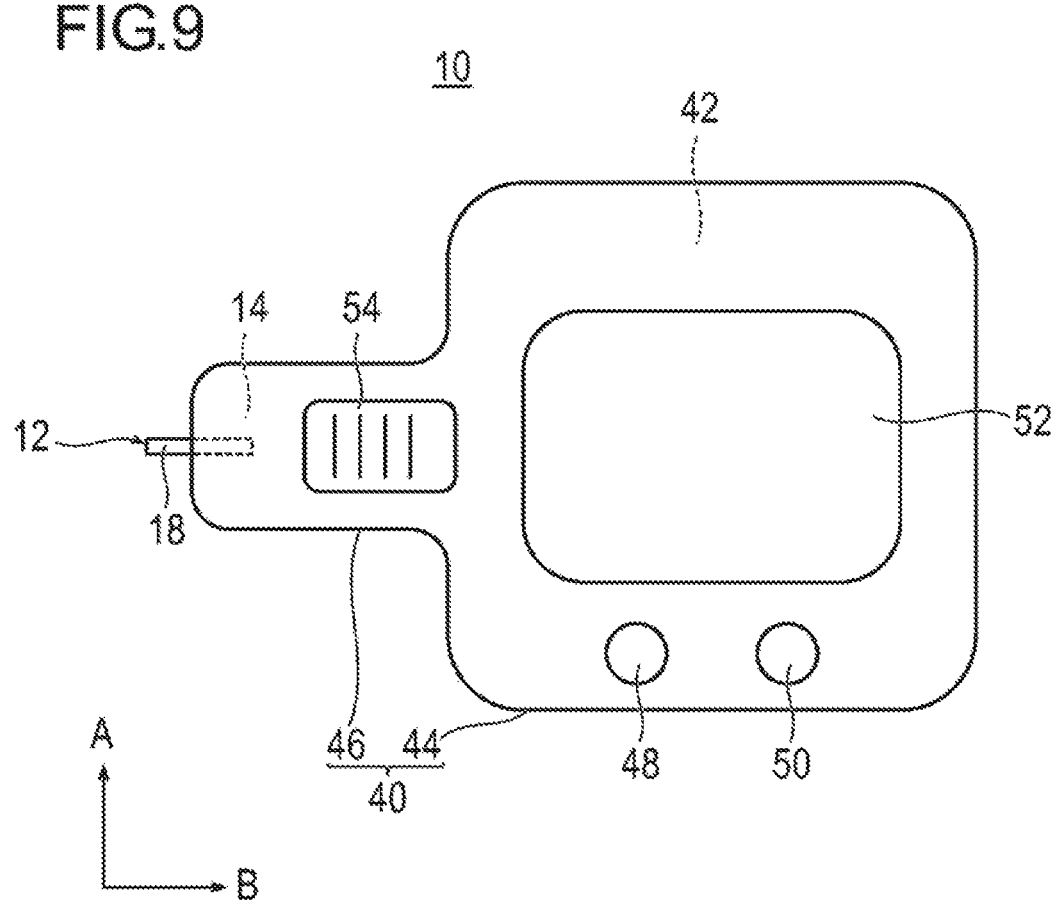

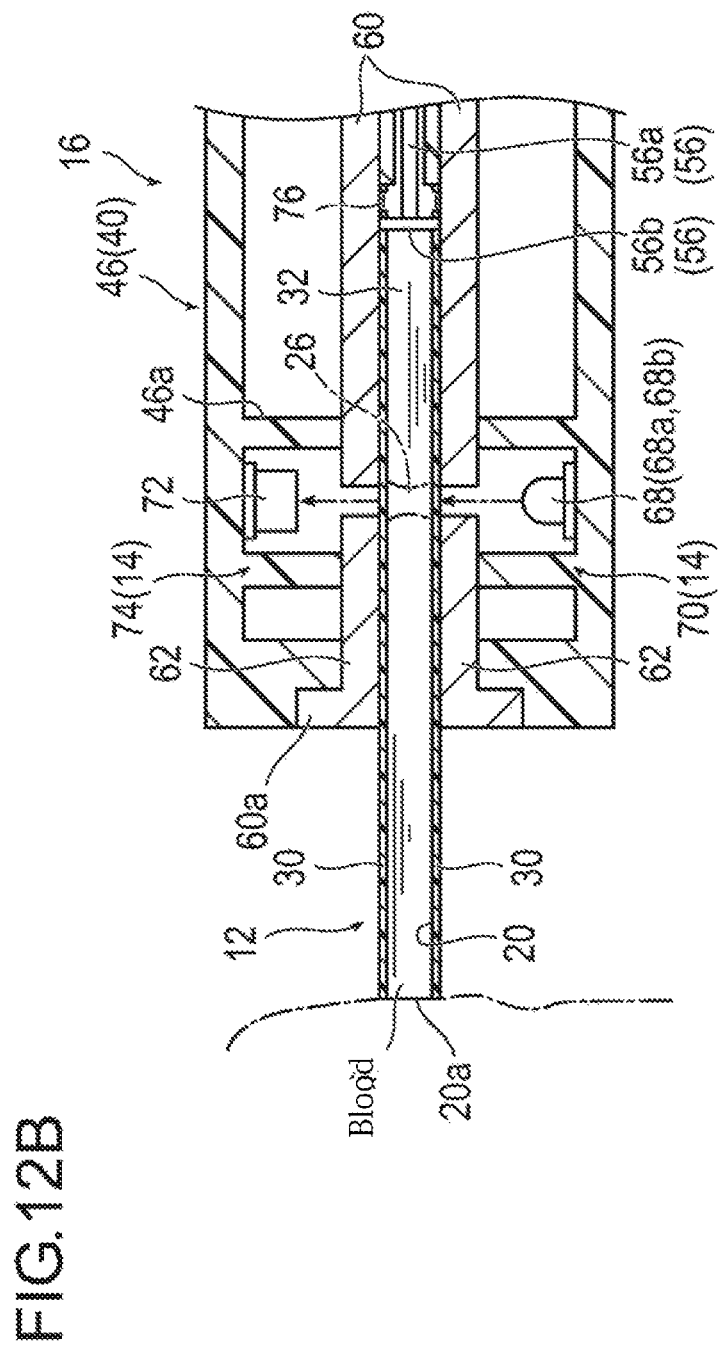

FIG.13A
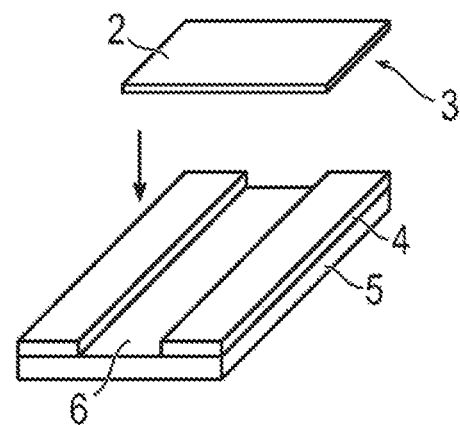
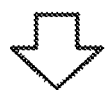
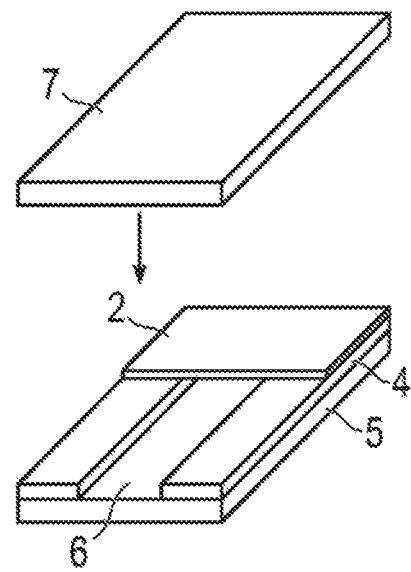

FIG. 13B
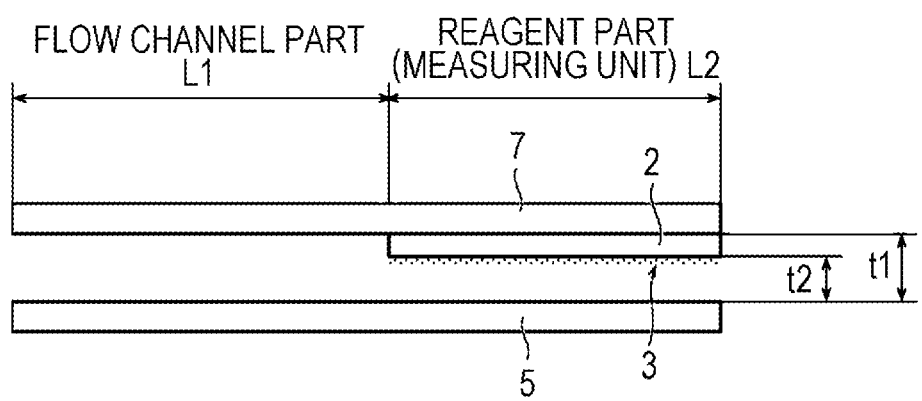
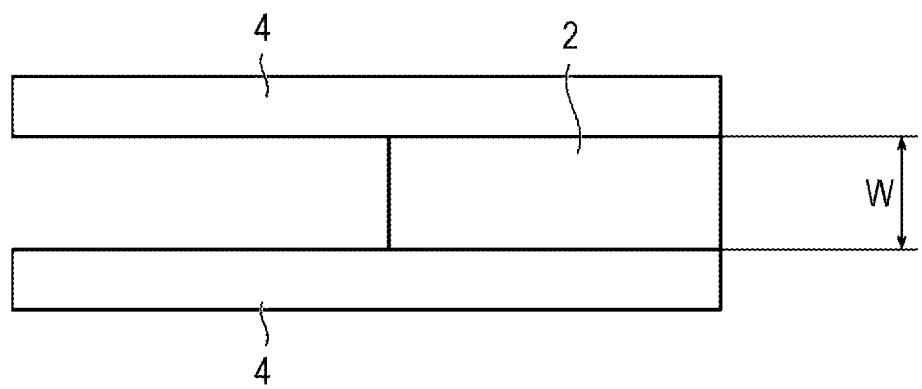

2-SUBSTITUTED BENZOTHIAZOLYL-3-SUBSTITUTED PHENYL-5-SUBSTITUTED SULFONATED PHENYL-2H-TETRAZOLIUM SALT, REAGENT FOR BIOLOGICAL COMPONENT CONCENTRATION MEASUREMENT CONTAINING SAID SALT, AND BIOLOGICAL COMPONENT CONCENTRATION MEASUREMENT METHOD USING SAID SALT

CROSS-REFERENCE TO RELATED APPLICATIONS

This is a bypass continuation of PCT Application No. PCT/JP2017/031677, filed on Sep. 1, 2017, which claims priority to Japanese Application No. 2016-179911, filed on Sep. 14, 2016. The contents of these application are hereby incorporated by reference in their entireties.

BACKGROUND

The present disclosure relates to a 2-substituted benzothiazolyl-3-substituted phenyl-5-substituted sulfonated phenyl-2H-tetrazolium salt, a reagent for biological component concentration measurement including the salt, and a method for measuring a biological component concentration using the salt.

BACKGROUND ART

In clinical chemical examinations, there are available methods for detecting and quantitatively determining the amount of a biological component included in a body fluid of an organism, such as blood or urine, depending on the amount of a coloring material that is detected, and reagents used for these methods are referred to as indicator reagents.

For example, JP 8-53444 A discloses a method for quantitatively determining a reduced nicotinic acid amide adenine dinucleotide using a water-soluble tetrazolium salt compound having the following structure:

[Chemical Formula 1]

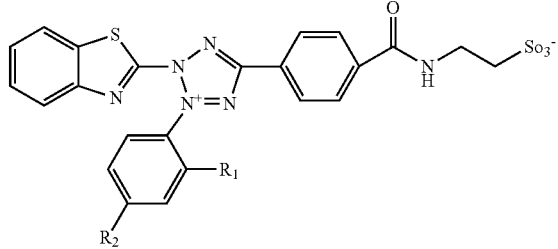

in which $R^1$ represents a hydrogen atom or a methoxy group; $R^2$ represents a hydrogen atom, a carboxyl group, or sulfonic acid.

SUMMARY

Formazan dye produced from the tetrazolium salt of the aforementioned JP 8-53444 A is highly water-soluble; however, the color development intensity in the wavelength range (600 nm or greater) that does not overlap with the main absorption band of hemoglobin is not sufficient. For this reason, when the tetrazolium salt of the aforementioned JP 8-53444 A is used, sufficient sensitivity cannot be achieved for whole blood samples.

Therefore, the present disclosure was achieved in view of such circumstances, and for a reagent for biological component concentration measurement has a sufficient coloring peak in a wavelength range (600 nm or greater) that does not overlap with the main absorption band of hemoglobin. Thereby, it is an object of the disclosure to provide a means capable of quantitatively determining a biological component with sufficient sensitivity even for a whole blood sample.

Another object of this disclosure is to provide a means capable of maintaining the water-solubility of a reagent for biological component concentration measurement while quantitatively determining a biological component stably with sufficient sensitivity even in the case of using the whole blood as a sample.

The inventors of the present disclosure conducted a thorough investigation in order to solve the problems described above, and as a result, the inventors found that the issues described above can be addressed by a tetrazolium salt having a benzothiazolyl group with a methoxy group or an ethoxy group introduced therein, at the 2-position of a tetrazole skeleton; a substituted phenyl group at the 3-position of the tetrazole skeleton; and a phenyl group having at least one sulfo group ($—SO_3^-$), at the 5-position of the tetrazole skeleton. Thus, the inventors have completed the present disclosure.

That is, the above-described object can be achieved by a 2-substituted benzothiazolyl-3-substituted phenyl-5-substituted sulfonated phenyl-2H-tetrazolium salt represented by the following Formula (1):

[Chemical Formula 2]

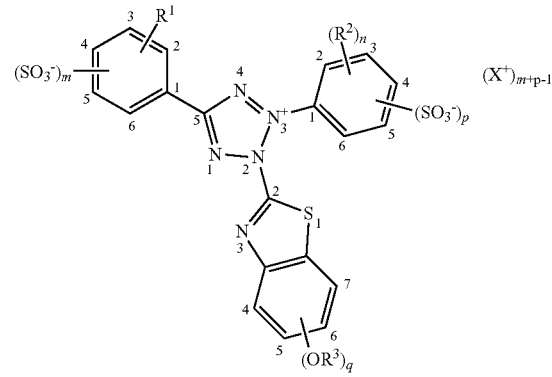

in which in Formula (1), $R^1$ represents any one selected from the group consisting of a hydrogen atom, a hydroxyl group, a methoxy group, and an ethoxy group; $R^2$ represents any one selected from the group consisting of a nitro group, $—OR^4$, and a carboxyl group ($—COO^-$), while multiple $R^2$'s may be identical with or different from each other; $R^3$ represents a hydrogen atom, a methyl group, or an ethyl group, while at least one is a methyl group or an ethyl group; $R^4$ represents a methyl group or an ethyl group; m represents the number of sulfo groups ($—SO_3^-$) bonded to the phenyl group at the 5-position of the tetrazole skeleton, and is 1 or 2; n represents the number of $R^2$'s bonded to the phenyl group at the 3-position of the tetrazole skeleton, and is an integer from 0 to 2; p represents the number of sulfo groups (—SO₃⁻) bonded to the phenyl group at the 3-position of the tetrazole skeleton, and is 0 or 1; n+p is 1 or greater; q is 1 or 2; when q is 2, the OR³'s are disposed adjacently to each other, while in this case, the OR³'s may be bonded to each other and form a ring; and X represents a hydrogen atom or an alkali metal atom.

BRIEF DESCRIPTION OF THE DRAWINGS

FIG. 9 is a plan view schematically illustrating a blood glucose meter (component measuring apparatus) equipped with a sensor chip according to the present embodiment.

FIG. 12B is a second plan cross-sectional view illustrating the operation of mounting subsequent to FIG. 12A.

FIG. 13A is a schematic diagram illustrating a blood glucose meter sensor used in Evaluation Example 2.

FIG. 13B is a diagram for explaining the length, width, and thickness of the inner surface of the blood glucose meter sensor of FIG. 13A.

DETAILED DESCRIPTION

Figure 1:
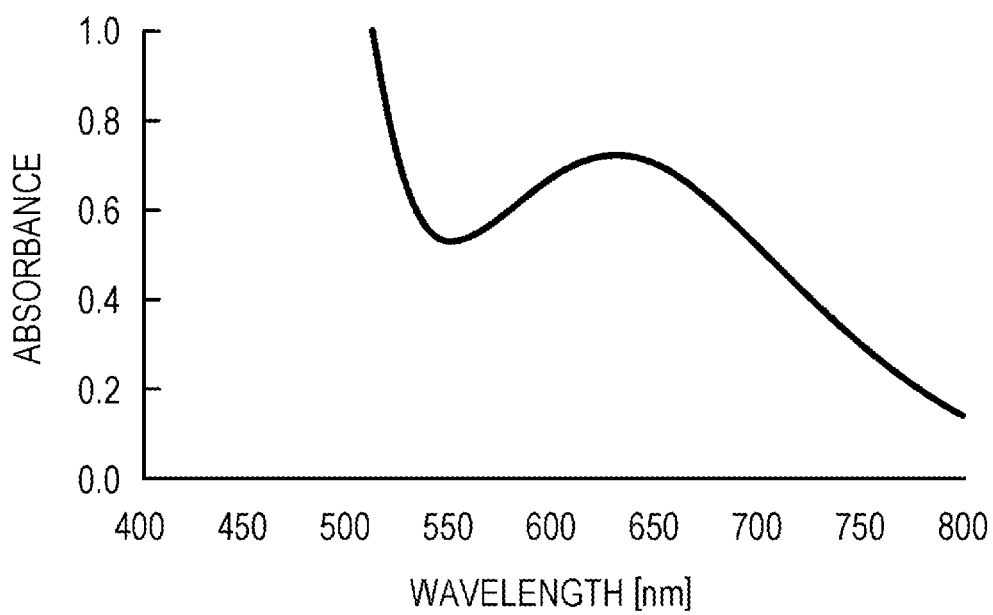
FIG. 1 is a diagram showing a spectrum of a Ni²⁺ chelate compound of formazan produced from tetrazolium compound 1.

According to a first aspect of the present disclosure, a 2-substituted benzothiazolyl-3-substituted phenyl-5-substituted sulfonated phenyl-2H-tetrazolium salt having a structure represented by the following Formula (1):

[Chemical Formula 3]

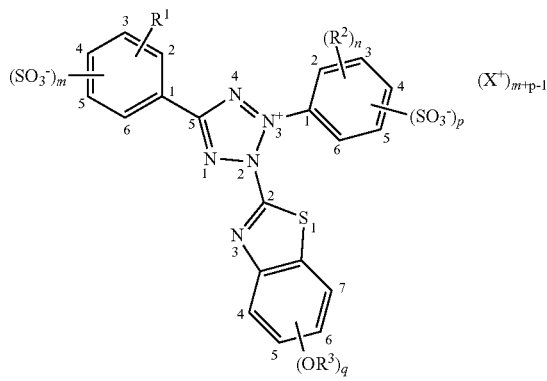

is provided. According to the present specification, the 2-substituted benzothiazolyl-3-substituted phenyl-5-substituted sulfonated phenyl-2H-tetrazolium salt of Formula (1) described above will be simply referred to as "tetrazolium salt of the present disclosure" or "tetrazolium salt".

A chelate compound formed from a transition metal ion and formazan produced from the tetrazolium salt of the present disclosure has the maximum absorption wavelength in a wavelength range (600 nm or greater) that does not overlap with the main absorption range of hemoglobin. For this reason, the influence of coloring substances existing in the blood is low, and the measurement error can be reduced. In the present specification, the chelate compound of a transition metal ion and formazan produced from the tetrazolium salt of the present disclosure is also simply referred to as "formazan compound".

The formazan produced from the tetrazolium salt of the aforementioned JP 8-53444 A has maximum absorption at 510 to 550 nm (paragraph [0011]). In fact, in Example 3 of the aforementioned JP 8-53444 A, the NADH concentration is quantitatively determined by means of the absorbance at 550 nm (paragraph [0029], FIG. 2). Meanwhile, in the case of measuring the concentration of a biological component (for example, glucose) using whole blood sample, it is necessary that the measurement wavelength is in a wavelength range that does not overlap with the main absorption band of hemoglobin. The wavelength for detecting the red blood cell concentration in the blood is about 510 to 540 nm, and the maximum absorption wavelength of oxygenated hemoglobin is approximately 550 nm. Therefore, in the case of biological component measurement using the whole blood as a sample, it is preferable that the maximum absorption wavelength of formazan be 600 nm or greater. In that case, in the formazan produced from the tetrazolium salt of JP 8-53444 A, the influence exerted by blood cells cannot be sufficiently eliminated, and it is difficult to measure the biological component concentration with satisfactory sensitivity. For this reason, it is necessary to shift the maximum absorption wavelength of the tetrazolium salt of JP 8-53444 A toward the longer wavelength range side. Generally, when a formazan of a certain kind is subjected to the action of a transition metal ion (for example, nickel ion or cobalt ion), and thereby a chelate compound is produced, the maximum absorption wavelength can be shifted toward the longer wavelength side. However, in Example 3 of JP 8-53444 A, even if a transition metal ion (for example, nickel ion) is added in order to shift the maximum absorption wavelength toward the longer wavelength side, the formazan does not form a chelate (see Comparative Example 5 described below), and when the amount of addition of the transition metal ion is increased, a precipitate is formed. Therefore, it is not apt to say that the tetrazolium salt of JP 8-53444 A can be suitably used as a reagent for a whole blood sample.

In contrast, the formazan compound produced from the tetrazolium salt of the present disclosure is such that the maximum absorption wavelength is in a wavelength range (600 nm or greater, particularly 630 nm or greater) that does not overlap with the absorption band of blood. Therefore, detection noises originating from a biological sample can be reduced by using the tetrazolium salt of the present disclosure. That is, a signal related to a biological component can be detected with high sensitivity. The detailed mechanism for providing the above-described effects is still not clearly understood; however, the mechanism may be considered as follows. In addition, the following mechanism is only a speculation and is not intended to limit the technical scope of the present disclosure.

The inventors of the present disclosure found that since the tetrazolium salt of the present disclosure has the benzothiazolyl group at the 2-position of the tetrazole skeleton substituted with an alkoxy group, the maximum absorption wavelength of formazan produced from the tetrazolium salt or a chelate compound of formazan and a transition metal ion can be shifted toward the longer wavelength side (comparison between Example 2 and Comparative Example 1 that are described below).

Furthermore, by means of the benzothiazolyl group existing at the 2-position of the tetrazole ring, the formazan produced from the tetrazolium salt of the present disclosure can efficiently and rapidly form a chelate compound with a transition metal ion such as $Co^{2+}$ or $Ni^{2+}$. This is thought to be due to the nitrogen atom of the benzothiazolyl group. Here, it is speculated that when the benzothiazolyl group is substituted with an alkoxy group, since the alkoxy group is an electron-donating group, the electron density of the benzothiazolyl group increases, and the formation of a chelate compound of formazan and a transition metal ion is carried out more rapidly. Therefore, it is considered very important to introduce an alkoxy group into the benzothiazolyl group existing at the 2-position of the tetrazole ring, in order to shift the maximum absorption wavelength toward the longer wavelength side while retaining the chelating ability of the formazan produced from a tetrazolium salt with a transition metal compound (comparison between Example 2 and Comparative Example 2 described below).

Therefore, when the tetrazolium salt of the present disclosure is used, the maximum absorption wavelength of the formazan compound produced from the tetrazolium salt of the present disclosure can be further shifted to a wavelength range (600 nm or greater, particularly 630 nm or greater) that does not overlap with the main absorption band of hemoglobin. For this reason, it is made possible to measure a biological component concentration with the maximum absorption wavelength existing in a wavelength range (600 nm or greater) that does not overlap with the main absorption band of hemoglobin, and even a biological component concentration in a whole blood sample can be accurately measured by using the tetrazolium salt of the present disclosure.

Furthermore, in the tetrazolium salt of the present disclosure, the phenyl group at the 5-position of the tetrazole skeleton has one or two sulfo groups (—$SO_3^-$), and the phenyl group at the 3-position of the tetrazole skeleton has zero or one sulfo group (—$SO_3^-$). Therefore, the tetrazolium salt has one to three sulfo groups (—$SO_3^-$) in the compound. Accordingly, the tetrazolium salt is water-soluble. Furthermore, the tetrazolium salt of the present disclosure has excellent stability.

Therefore, a biological component concentration can be measured rapidly with high sensitivity by using the tetrazolium salt of the present disclosure. Furthermore, a biological component concentration can be measured with high sensitivity even after a long-term storage, by using the tetrazolium salt of the present disclosure.

In the following description, embodiments of the present disclosure will be explained in detail.

The tetrazolium salt according to an embodiment of the present disclosure has a structure represented by the following Formula (1):

[Chemical Formula 4]

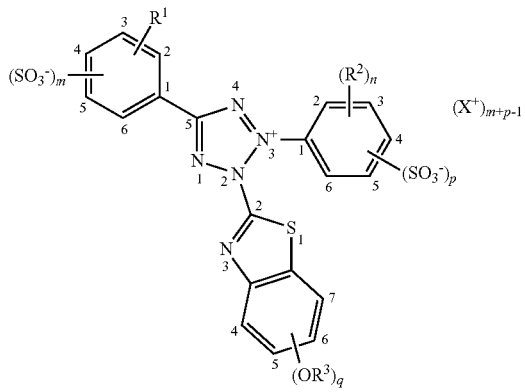

In Formula (1), $R^1$ represents any one selected from the group consisting of a hydrogen atom, a hydroxyl group, a methoxy group, and an ethoxy group; $R^2$ represents any one selected from the group consisting of a nitro group, —$OR^4$, and a carboxyl group; $R^3$ represents a hydrogen atom, a methyl group, or an ethyl group, while at least one is a methyl group or an ethyl group; $R^4$ represents a methyl group or an ethyl group; m represents the number of sulfo groups (—$SO_3^-$) bonded to the phenyl group at the 5-position of the tetrazole skeleton, and is 1 or 2; n represents the number of $R^2$'s bonded to the phenyl group at the 3-position of the tetrazole skeleton, and is an integer from 0 to 2; p represents the number of sulfite ions (—$SO_3^-$) bonded to the phenyl group at the 3-position of the tetrazole skeleton, and is 0 or 1; n+p is 1 or greater; q is 1 or 2; when q is 2, the $OR^3$'s are disposed adjacently to each other, while in this case, the $OR^3$'s may be bonded to each other and form a ring; and X represents a hydrogen atom or an alkali metal atom.

The tetrazolium salt according to another embodiment of the present disclosure has a structure represented by the following Formula (1'):

[Chemical Formula 5]

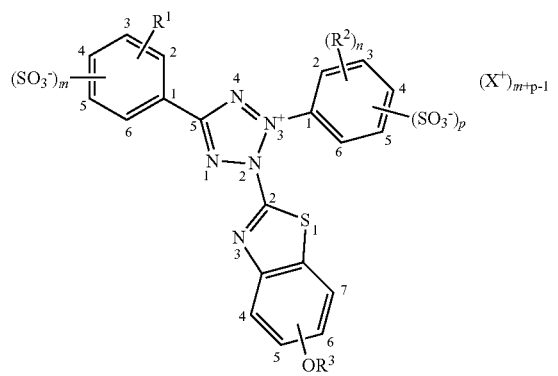

Formula (1')

In this formula, $R^1$ represents anyone selected from the group consisting of a hydrogen atom, a hydroxyl group, a methoxy group, and an ethoxy group; $R^2$ represents any one selected from the group consisting of a nitro group —$OR^4$, and a carboxyl group; $R^3$ and $R^4$ each independently represent a methyl group or an ethyl group; m represents the number of sulfo groups (—$SO_3^-$) bonded to the phenyl group at the 5-position of the tetrazole skeleton, and is 1 or 2; n represents the number of $R^2$ bonded to the phenyl group at the 3-position of the tetrazole skeleton, and is an integer from 0 to 2; p represents the number of sulfo groups (—$SO_3^-$) bonded to the phenyl group at the 3-position of the tetrazole skeleton, and is 0 or 1; n+p is 1 or greater; and X represents a hydrogen atom or an alkali metal atom.

In Formula (1), a substituted benzothiazolyl group exists at the 2-position of the tetrazole skeleton. In regard to the above-described Formula (1), since a benzothiazolyl group exists at the 2-position of the tetrazole ring, the compound can form a chelate compound with a transition metal compound efficiently and rapidly (the maximum absorption wavelength of the formazan compound can be shifted to a longer wavelength range). Then, since at least one methoxy group or ethoxy group is introduced into the benzothiazolyl group at the 2-position of the tetrazole skeleton, the maximum absorption wavelength at the time of chelation between formazan thus produced and a transition metal ion such as $Ni^{2+}$ is further shifted toward the longer wavelength side (comparison between Example 2 and Comparative Example 1 described below).

Furthermore, q is 1 or 2. Here, in the case of q=1, $R^3$ represents a methyl group or an ethyl group, and from the viewpoint of water-solubility, $R^3$ is preferably a methyl group. In a case in which $R^3$ is an alkyl group having 3 or more carbon atoms, the tetrazolium salt and formazan produced from the tetrazolium salt have poor water-solubility, which is not preferable.

In regard to Formula (1), from the viewpoint of the effect of shifting the maximum absorption wavelength toward the longer wavelength side at the time of chelation with a transition metal ion such as $Ni^{2+}$, it is preferable that at least one of —$OR^3$ of the substituted benzothiazolyl group existing at the 2-position of the tetrazole skeleton is bonded to the 6-position of the benzothiazolyl group.

In the case of q=1, the position of substitution of —$OR^3$, which is a substituent of the benzothiazolyl group existing at the 2-position of the tetrazole skeleton, is not particularly limited, and the position of substitution may be any one of the 4-position, 5-position, 6-position or 7-position. From the viewpoint of the effect of shifting the maximum absorption wavelength toward the longer wavelength side at the time of chelation with a transition metal ion such as $Ni^{2+}$, it is preferable that the position of substitution of —$OR^3$ is bonded to the 6-position of the benzothiazolyl group.

In the case of q=2, $R^3$ represents a hydrogen atom, a methyl group, or an ethyl group, and at least one is a methyl group or an ethyl group. Furthermore, when q is 2, these $OR^3$'s may be disposed adjacently to each other, and the $OR^3$'s may be bonded to each other and form a ring. In this case, a suitable combination is a combination of a hydrogen atom and a methyl group for $R^3$, or a combination of a methyl group and a methyl group for $R^3$. In the case of q=2, the positions of substitution of —$OR^3$, which is a substituent of the benzothiazolyl group existing at the 2-position of the tetrazole skeleton, are not particularly limited as long as two —$OR^3$'s are disposed adjacently to each other, and the positions of substitution may be any one of the combinations of the 4,5-positions, the 5,6-position, and the 6,7-position. From the viewpoint of the effect of shifting the maximum absorption wavelength toward the longer wavelength side at the time of chelation with a transition metal ion such as $Ni^{2+}$, for the position of substitution of at least one —$OR^3$, it is preferable that —$OR^3$ is bonded to the 6-position of the benzothiazolyl group, that is, the positions of substitution of two —OR³'s are preferably the 5,6-position, or the 6,7-position. Specifically, in a case in which q is 2, it is preferable that the substituted benzothiazolyl group existing at the 2-position of the tetrazole skeleton is any one of the following substituents.

[Chemical Formula 6]

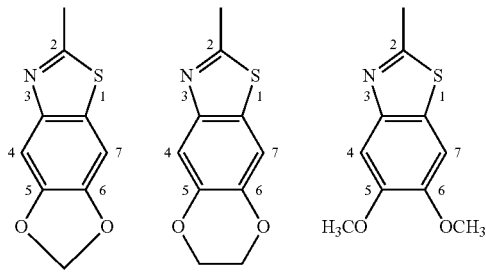

Furthermore, when q is 2, in a case in which the substituted benzothiazolyl group existing at the 2-position of the tetrazole skeleton is any one of the above-described substituents, it is preferable that the substituted sulfonated phenyl group existing at the 3-position of the tetrazole skeleton is a 4-methoxy-5-sulfophenyl group, from the viewpoint of the effect of shifting the maximum absorption wavelength toward the longer wavelength side at the time of chelation with a transition metal ion such as $Ni^{2+}$.

In Formula (1), a substituted sulfonated phenyl group exists at the 5-position of the tetrazole skeleton. $R^1$, which is a substituent for the sulfonated phenyl group, is any one selected from the group consisting of a hydrogen atom, a hydroxyl group, a methoxy group, and an ethoxy group. From the viewpoint of enhancing the water-solubility of the tetrazolium salt and the formazan produced from the tetrazolium salt, $R^1$ is preferably a hydrogen atom or a hydroxyl group. From the viewpoint that the compound can stably form a chelate with a transition metal ion in a wide pH region, $R^1$ is more preferably a hydrogen atom. Furthermore, the position of substitution in a case in which $R^1$ is a hydroxyl group, a methoxy group, or an ethoxy group is not particularly limited; however, the position of substitution is preferably the 4-position.

At the 5-position of the tetrazole skeleton, at least one sulfo group ($-SO_3^-$) exists (m=1 or 2). It is considered that due to this sulfo group, the water-solubility of the tetrazolium salt and the formazan produced from the tetrazolium salt is enhanced. In regard to Formula (1), m represents the number of sulfo groups ($-SO_3^-$) bonded to the phenyl group at the 5-position of the tetrazole skeleton, and is 1 or 2. Particularly, in a case in which a sulfo group is at the 2-position or the 4-position, and in a case in which sulfo groups are at the 2,4-position, a further enhancement of water-solubility can be exhibited. Furthermore, when sulfo groups are at the 2,4-position, it is advantageous from the viewpoint that the synthesis of building blocks for synthesizing the compound is easier. From the viewpoint that the compound is highly water-soluble and can stably form a chelate compound with a transition metal ion in a wide pH region, or from the viewpoint that water-solubility is enhanced, it is preferable that m=2, and it is more preferable that m=2, and $R^1$ represents a hydrogen atom.

At this time, in a case in which m=2, it is preferable that p, which is the number of sites at which a sulfo group ($-SO_3^-$) is bonded to the phenyl group at the 3-position of the tetrazole skeleton, is 1. When such a number of substituents are selected, the water-solubility of the tetrazolium salt and the formazan produced therefrom is further enhanced.

In addition, from the viewpoint of water-solubility, it is preferable to satisfy any one of the following items (1) to (4): (1) m=2, and p=1; (2) m=1, and n=0; (3) in regard to the phenyl group existing at the 5-position of the tetrazole skeleton, $R^1$ is a hydroxyl group, and at this time, a sulfo group ($SO_3^-$) and a hydroxyl group are at the 2,4-position or the 4- and 6-positions; and (4) p=0, and at least one of $R^2$'s is a carboxyl group. It is more preferable that (1) m=2, and p=1; or (4) p=0, and at least one of $R^2$'s is a carboxyl group. In the item (3), it is speculated that since the sulfo group ($SO_3^-$) and the hydroxyl group do not exist as adjacent substituents on the benzene ring, there is no, or less, hydrogen bonding between the substituents, and the two substituents can efficiently contribute to water-solubility.

Here, the position of bonding of a sulfo group ($-SO_3^-$) to the phenyl group existing at the 5-position of the tetrazole skeleton is not particularly limited. From the viewpoint of the effect of further enhancing the water-solubility of the tetrazolium salt and the formazan produced from the tetrazolium salt, and from the viewpoint that the maximum absorption wavelength can be shifted toward the longer wavelength side, in the case of m=2, it is preferable that sulfo groups ($-SO_3^-$) exist at the 2,4-position or the 3,5-position of the phenyl group. It is particularly preferable that sulfo groups exist at the 2,4-position of the phenyl group, and a tetrazolium salt compound that does not precipitate even in the presence of a transition metal ion at a high concentration can be obtained. That is, by using this tetrazolium salt as an indicator reagent, a reagent composition for biological component measurement that can be quantitatively determined even in a case in which the biological component is at a high concentration, can be produced. That is, according to a preferred embodiment of the present disclosure, it is preferable that the phenyl group at the 5-position of the tetrazole skeleton is a phenyl group in which sulfo groups ($-SO_3^-$) exist at the 2- and 4-positions.

In regard to Formula (1), a substituted phenyl group exists at the 3-position of the tetrazole skeleton. Since the phenyl group is essentially substituted, n+p is 1 or greater.

$R^2$ as a substituent for the phenyl group at the 3-position of the tetrazole skeleton is any one selected from the group consisting of a nitro group, $-OR^4$, and a carboxyl group. From the viewpoint of the formability of a chelate between formazan and a transition metal ion, $R^2$ is preferably a nitro group or $-OR^4$, and from the viewpoint of water-solubility, $R^2$ is preferably a carboxyl group. Furthermore, n represents the number of $R^2$ bonded to the phenyl group at the 3-position of the tetrazole skeleton, and is an integer from 0 to 2. As described below, by introducing $R^2$, the maximum absorption wavelength of the compound can be moved to a longer wavelength range, or the stability of the compound can be enhanced. Therefore, it is preferable that n=1 or 2. In a case in which two $R^2$'s exist, that is, n=2, $R^2$'s may be identical or different.

When n=1 or 2, it is preferable that at least one of $R^2$'s is a $-OR^4$ group. That is, a suitable embodiment of the present disclosure is such that n is 1 or 2, and at least one of $R^2$'s is a $-OR^4$ group. When an alkoxy group is introduced as a substituent of the phenyl group, stability of the compound is enhanced. From the viewpoint of enhancing the water-solubility of the tetrazolium salt and the formazan produced from the tetrazolium salt, it is preferable that the $-OR^4$ group is a methoxy group. Here, it is preferable that $R^4$ is a methyl group or an ethyl group, and from the viewpoint of water-solubility, it is preferable $R^4$ is a methyl group. In a case in which $R^4$ is an alkyl group having 3 or more carbon atoms, the tetrazolium salt and the formazan produced from the tetrazolium salt have poor water-solubility, which is not preferable.

The position of substitution of $R^2$ in a case in which n is 1 or 2 is not particularly limited; however, it is preferable that the position of substitution of the substituted sulfophenyl group existing at the 3-position of the tetrazole skeleton is the 2-position, 3-position, 4-position, 5-position, or 6-position; it is preferable that at least one of $R^2$ is at the 2-position or the 4-position; and it is preferable that the position of substitution is the 2-position and/or the 4-position. By adopting such a structure, water-solubility is enhanced, and at the same time, the stability of the tetrazolium salt and the formazan produced from the tetrazolium salt can be enhanced.

p represents the number of sulfo groups ($-SO_3^-$) bonded to the phenyl group at the 3-position of the tetrazole skeleton, and is 0 or 1. From the viewpoint of enhancing the water-solubility of the tetrazolium salt and the formazan produced from the tetrazolium salt, it is preferable that p=1. In the case of p=1, since a sulfo group is an electron-withdrawing group, when there is another electron-withdrawing group (for example, a nitro group), the cationic charge of the nitrogen atom on the tetrazolium ring may be destabilized, and the stability of the compound may be deteriorated. As described above, stability of the compound is enhanced by introducing an alkoxy group as a substituent of the phenyl group; however, when a nitro group is introduced at the same time, an enhancement of the stability induced by the introduction of an alkoxy group may not be exhibited. Therefore, from the viewpoint of enhancing stability, in the case of p=1, n is 1 or 2, and preferably n is 1. Meanwhile, $R^2$ is preferably any one selected from the group consisting of $-OR^4$ and a carboxyl group, and it is more preferable that $R^2$ is $-OR^4$. Alternatively, from the viewpoint of enhancing the water-solubility of the tetrazolium salt and the formazan produced from the tetrazolium salt, it is preferable that p=0, and at least one of $R^2$'s is a carboxyl group. That is, according to a suitable embodiment, in regard to Formula (1), p is 1, or p=0 and at least one of $R^2$'s is a carboxyl group. More suitably, m=2 and p=1, or p=0 and at least one of $R^2$'s is a carboxyl group.

In a case in which p=1, the position of substitution of the sulfo group ($-SO_3^-$) that substitutes the phenyl group at the 3-position of the tetrazole skeleton is not particularly limited; however, it is preferable that the position of substitution is the 3-position or the 5-position. When the sulfo group is substituted at this position, the stability of the tetrazolium salt and the formazan produced from the tetrazolium salt can be enhanced more effectively.

Furthermore, in regard to Formula (1), the substituent existing at the 3-position of the tetrazole skeleton is preferably a 4-methoxy-3-sulfophenyl group, a 2-methoxy-5-sulfophenyl group, a 2-methoxy-4-nitro-5-sulfophenyl group, a 2-methoxy-4-nitrophenyl group, a 4-sulfophenyl group, a 4-carboxy-2-methoxyphenyl group, a 5-carboxy-2-methoxyphenyl group, a 3-carboxy-4-methoxyphenyl group, or a 4-methoxy-5-sulfophenyl group; more preferably a 4-methoxy-3-sulfophenyl group, a 2-methoxy-5-sulfophenyl group, a 3-carboxy-4-methoxyphenyl group, or a 4-methoxy-5-sulfophenyl group; and particularly preferably a 4-methoxy-3-sulfophenyl group, a 4-methoxy-5-sulfophenyl group, or a 2-methoxy-5-sulfophenyl group. By adopting such structures, the color development sensitivity is increased, water-solubility is increased, and also, the stability of the tetrazolium salt and the formazan produced from the tetrazolium salt can be enhanced. Furthermore, since the maximum absorption wavelength of the formazan compound itself can be shifted to a longer wavelength range, it is particularly preferable that the phenyl group existing at the 3-position of the tetrazole skeleton is a 4-methoxy-3-sulfophenyl group.

The total number of sulfo groups (m+p) existing in Formula (1) is preferably 2 or greater, and more preferably 3, from the viewpoint of enhancing the water-solubility of the tetrazolium salt and the formazan produced from the tetrazolium salt.

In Formula (1) described above, X represents a hydrogen atom or an alkali metal atom. Here, X exists in order to neutralize an anion (sulfo group ($-SO_3^-$)). Therefore, the type of the alkali metal is not particularly limited and may be any one of lithium, sodium, potassium, rubidium, and cesium.

Preferred examples of the tetrazolium salt include the following. Meanwhile, in the structures described below, X represents an alkali metal atom.

[Chemical Formula 7-1]

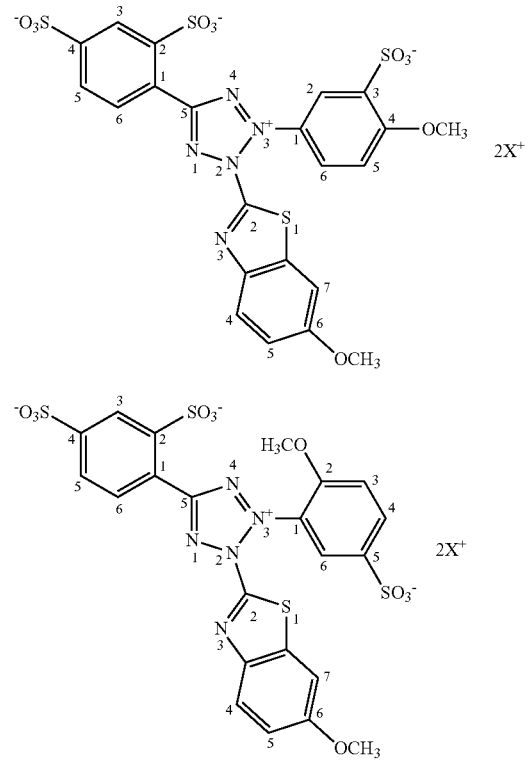

-continued
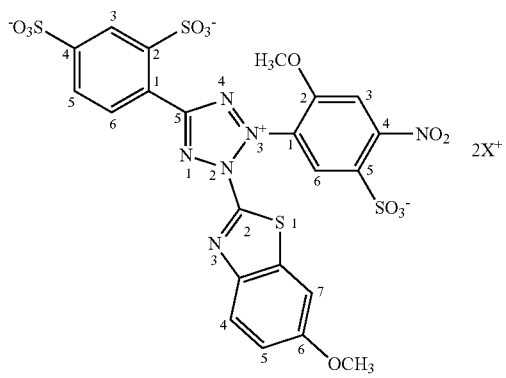
2X⁺
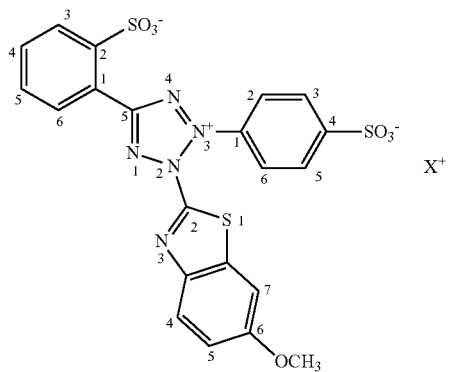
X⁺
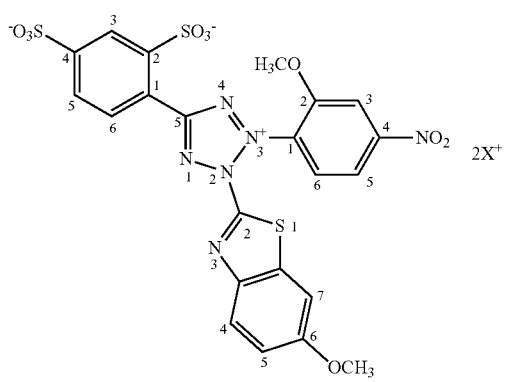
2X⁺
[Chemical Formula 7-3]
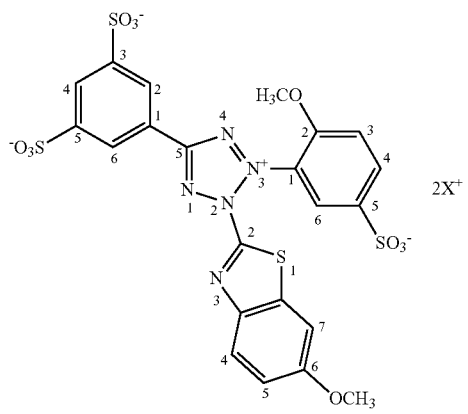
2X⁺
[Chemical Formula 7-2]
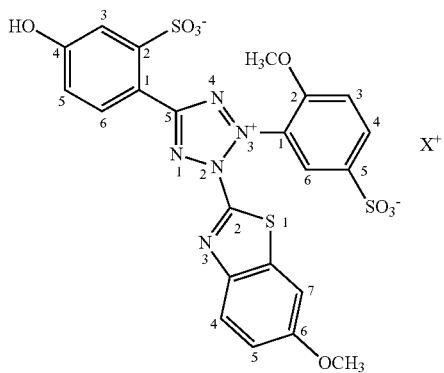
X⁺
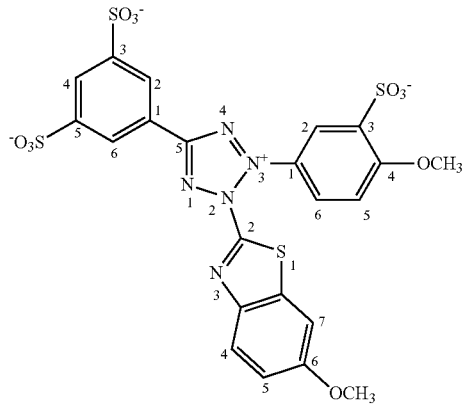
2X⁺
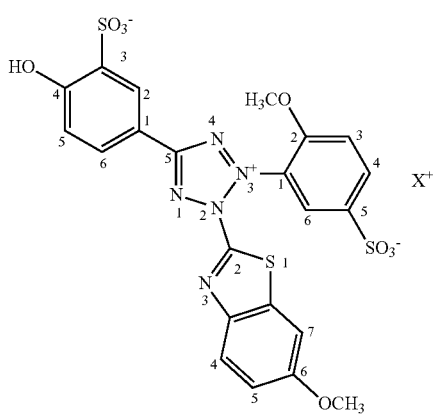
X⁺
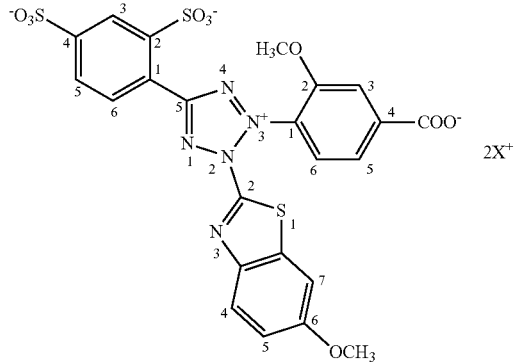
2X⁺

-continued
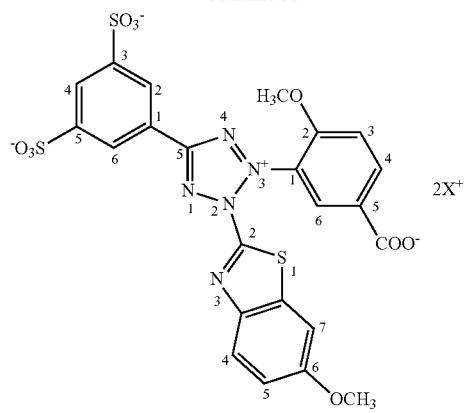
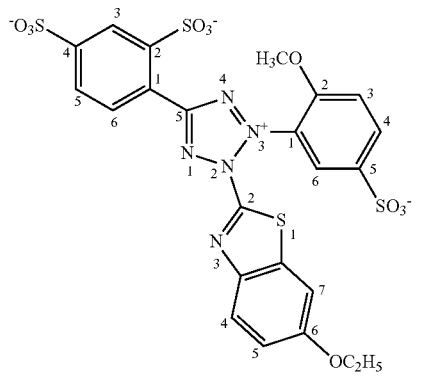
[Chemical Formula 7-4]
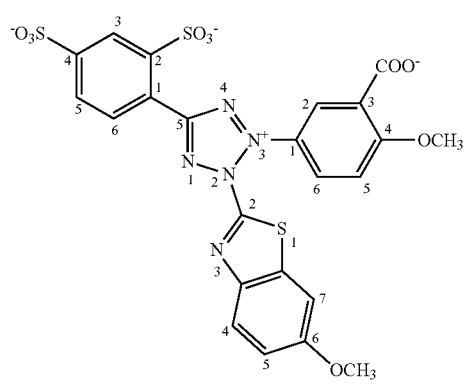
[Chemical Formula 7-5]
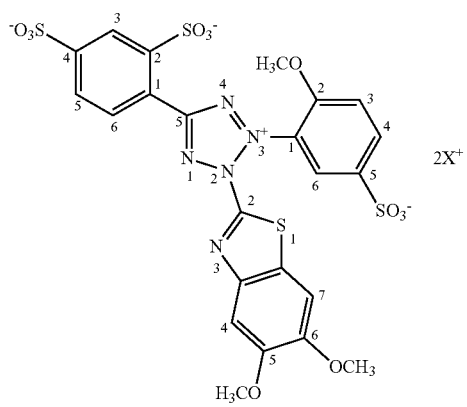
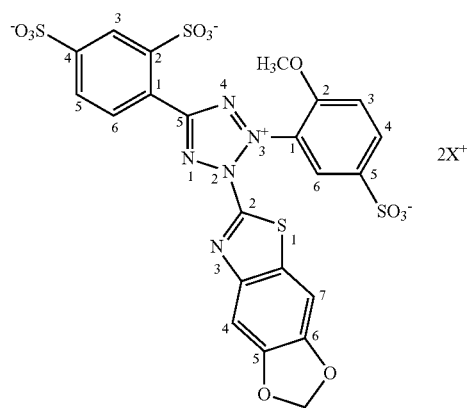
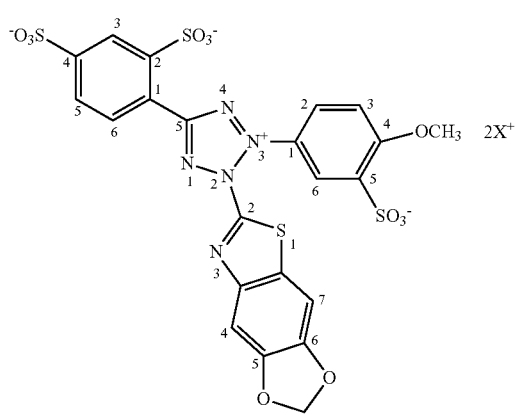
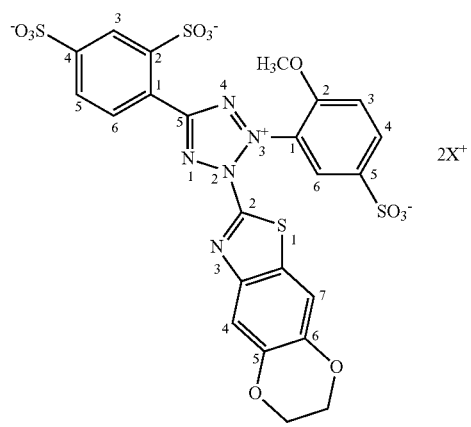
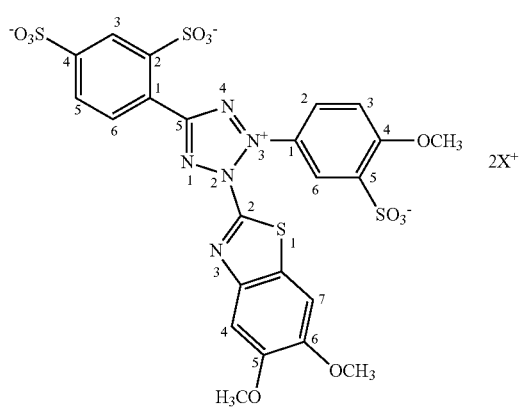

-continued

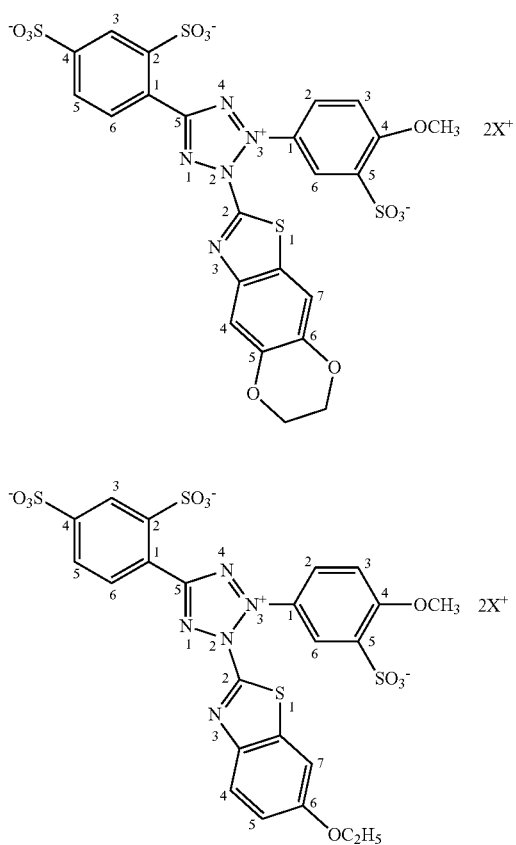

The method for producing the tetrazolium salt of the present disclosure is not particularly limited, and conventionally known methods can be applied in a similar manner or after being appropriately modified. For example, hydrazone is synthesized by dehydration and condensation of aldehyde and hydrazine, and then a corresponding diazonium salt is caused to react in an aqueous solvent under basic conditions. Thereby, formazan is obtained. Here, for the basifying agent, sodium hydroxide, potassium hydroxide, and the like are used. Next, the formazan thus obtained is oxidized in an alcohol solvent (for example, methanol or ethanol) using an oxidizing agent such as ethyl nitrite, butyl nitrite, or sodium hypochlorite, and a tetrazolium salt of Formula (1) can be obtained. According to an embodiment, a hydrazino-substituted benzothiazole having the following structure:

[Chemical Formula 8]

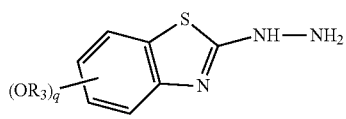

is caused to react with a substituted sulfonated benzaldehyde having the following structure:

[Chemical Formula 9]

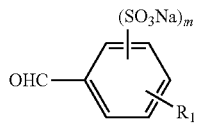

and a hydrazone compound is obtained having the following structure:

[Chemical Formula 10]

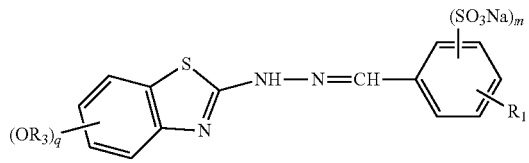

Meanwhile, while a substituted sulfonated aniline having the following structure:

[Chemical Formula 11]

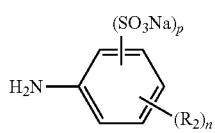

is ice-cooled, hydrochloric acid is added thereto, and a sodium nitrite solution is added dropwise to the mixture. Thus, a benzenediazonium chloride compound having the following structure:

[Chemical Formula 12]

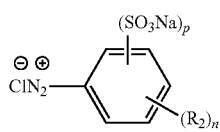

is obtained. The hydrazone compound and the benzenediazonium chloride compound obtained as described above are allowed to react under basic conditions (for example, in the presence of sodium hydroxide or potassium hydroxide), and thereby a formazan compound having the following structure:

[Chemical Formula 13]

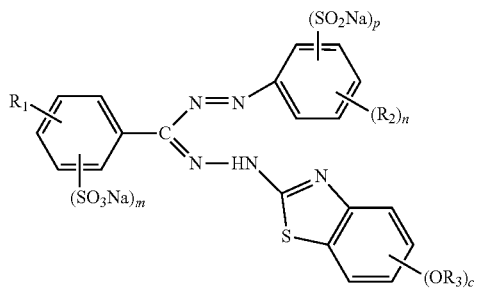

is obtained. Next, the formazan compound obtained in this manner is oxidized in an alcohol solvent (for example, methanol or ethanol) using an oxidizing agent (for example, a nitrous acid ester such as sodium nitrite, ethyl nitrite, or butyl nitrite), and thereby the tetrazolium salt of the present disclosure is obtained.

The formazan produced from the tetrazolium salt of the present disclosure, or a chelate compound of formazan and a transition metal ion acquires the maximum absorption wavelength in a wavelength range (600 nm or greater, particularly 650 nm or greater) that does not overlap with the main absorption band of hemoglobin, by being used alone or by forming a chelate compound with a transition metal compound. Furthermore, the tetrazolium salt of the present disclosure is highly water-soluble. Therefore, the biological component concentration in a biological sample, particularly even in a whole blood sample, can be measured with high sensitivity by using the tetrazolium salt of the present disclosure. Specifically, the maximum absorption wavelength ($\lambda$max) of the formazan produced from the tetrazolium salt of the present disclosure or the chelate compound of formazan and a transition metal ion is preferably 600 nm or greater, more preferably 630 nm or greater, and particularly preferably 650 nm or greater. When formazan or a chelate compound of formazan and a transition metal ion (therefore, a tetrazolium salt capable of producing such a formazan) having such a maximum absorption wavelength is used, the measurement is not likely to be affected by the absorption of blood, and the biological component concentration can be measured more accurately with satisfactory sensitivity. Here, the upper limit of the maximum absorption wavelength ($\lambda$max) of the formazan produced from the tetrazolium salt of the present disclosure or the chelate compound of formazan and a transition metal ion is not particularly limited; however, the upper limit is usually 900 nm or less, and preferably 800 nm or less. Meanwhile, in the present specification, regarding the maximum absorption wavelength ($\lambda$max), a value measured according to the method described in the following Embodiments will be employed.

Therefore, according to a second aspect of the present disclosure, there is provided a reagent for biological component concentration measurement including 2-substituted benzothiazolyl-3-substituted phenyl-5-substituted sulfonated phenyl-2H-tetrazolium salt of the present disclosure. Furthermore, according to a third aspect, there is provided a method for measuring a biological component concentration, the method including adding 2-substituted benzothiazolyl-3-substituted phenyl-5-substituted sulfonated phenyl-2H-tetrazolium salt of the present disclosure, an oxidoreductase, and a transition metal compound to a biological sample, measuring the quantity of color development, and quantitatively determining the concentration of a biological component in the biological sample based on the quantity of color development.

According to the present disclosure, the object of biological component measurement is not particularly limited as long as the object includes the intended biological component. Specific examples of the object of biological component measurement include blood as well as body fluids such as urine, saliva, and interstitial fluid. Furthermore, the biological component is not particularly limited, and usually, a biological component that is measured by a colorimetric method or an electrode method can be used similarly. Specific examples include glucose, cholesterol, neutral lipids, nicotinamide adenine dinucleotide phosphate (NADPH), nicotinamide adenine dinucleotide (NADH), and uric acid. That is, according to a preferred embodiment of the second aspect of the disclosure, the reagent for biological component concentration measurement of the present disclosure is used for the measurement of the concentration of glucose, cholesterol, neutral lipids, nicotinamide adenine dinucleotide phosphate (NADPH), nicotinamide adenine dinucleotide (NADH), and uric acid in the blood or in a body fluid. Furthermore, according to a preferred embodiment of the third aspect of the present disclosure, the biological component in a biological sample is glucose, cholesterol, neutral lipids, nicotinamide adenine dinucleotide phosphate (NADPH), nicotinamide adenine dinucleotide (NADH), or uric acid in the blood or in a body fluid.

The reagent for biological component concentration measurement of the present disclosure essentially includes the tetrazolium salt of the present disclosure. As described above, in the reagent for biological component concentration measurement, the formazan produced by a reduction reaction of the tetrazolium salt has the maximum absorption wavelength on the longer wavelength side, compared to the tetrazolium salts that are currently distributed. As the tetrazolium salt of the present disclosure produces a chelate compound with a transition metal ion, the maximum absorption wavelength can be shifted toward the longer wavelength side. Therefore, particularly in the case of measuring the biological component concentration in a whole blood sample, it is preferable that the measurement system includes a transition metal compound. That is, according to a preferred embodiment of the present disclosure, the reagent for biological component concentration measurement further includes a transition metal compound. According to this embodiment, even in the case of measuring the biological component concentration in a whole blood sample, formazan has the maximum absorption wavelength in a wavelength range (600 nm or greater) that does not overlap with the main absorption band of hemoglobin. Therefore, in a biological sample, particularly even in a whole blood sample, the measurement sensitivity of the biological component concentration can be further increased. The transition metal compound that can be used in a case in which the reagent for biological component concentration measurement includes a transition metal compound is not particularly limited. Specifically, a compound that can produce a transition metal ion such as nickel ion ($Ni^{2+}$), cobalt ion ($Co^{2+}$), zinc ion ($Zn^{2+}$), or copper ion ($Cu^{2+}$), can be used. When such an ion is used, the maximum absorption wavelength of formazan can be further shifted toward the longer wavelength side. Among these, nickel ion is preferred. Since nickel ion is not likely to be subjected to the action of oxidation or reduction, the error of measurement can be reduced more effectively. That is, according to a preferred embodiment of the present disclosure, the transition metal compound is a nickel compound. Furthermore, the compound that produces the transition metal ion is not particularly limited; however, a compound that produces ions in an aqueous liquid (for example, water, a buffer solution, blood, or a body fluid) is preferred. Examples thereof include chlorides, bromides, sulfates, and organic acid salts of the above-mentioned transition metals. The transition metal compounds described above may be used singly or in combination of two or more kinds thereof. Furthermore, according to the present embodiment, the content of the transition metal compound is not particularly limited; however, the content can be appropriately selected according to the desired maximum absorption wavelength of the formazan compound. Specifically, the content of the transition metal compound is preferably an amount such that the proportion of the transition metal (transition metal ions) is 0.1 to 10 mol, and more preferably 0.5 to 4 mol, with respect to 1 mol of the tetrazolium salt. With such an amount, the maximum absorption wavelength of the formazan compound can be shifted to a desired wavelength range.

The reagent for biological component concentration measurement may further include other components, in addition to the transition metal compound or instead of the transition metal compound. Here, regarding the other components, usually, components that are appropriately selected according to the type of the biological component as an object of measurement and are added for the purpose of measuring the concentration of the biological component, can be similarly used. Specific examples include an oxidoreductase, an electron carrier, a pH buffering agent, and a surfactant. Here, the above-mentioned other components may be respectively used singly, or two or more kinds thereof may be used in combination. Furthermore, each of the above-mentioned other components may be used singly or in combination of two or more kinds thereof.

Here, the oxidoreductase is not particularly limited and can be appropriately selected depending on the type of the biological component as an object of measurement. Specific examples include glucose dehydrogenases such as a glucose dehydrogenase (GDH), a glucose dehydrogenase that uses pyrroloquinoline quinone (PQQ) as a coenzyme (PQQ-GDH), a glucose dehydrogenase that uses flavin adenine dinucleotide (FAD) as a coenzyme (GDH-FAD), a glucose dehydrogenase that uses nicotinamide adenine dinucleotide (NAD) as a coenzyme (GDH-NAD), and a glucose dehydrogenase (GDH) that uses nicotine adenine dinucleotide phosphate (NADP) as a coenzyme (GDH-NADP) or the like; glucose oxidase (GOD), lactic acid dehydrogenase (LDH), cholesterol dehydrogenase, cholesterol oxidase, and uric acid dehydrogenase. Here, the oxidoreductases may be used singly, or two or more kinds thereof may be used in combination. For example, in a case in which the biological component is glucose, it is preferable that the oxidoreductase is a glucose dehydrogenase or a glucose oxidase. In a case in which the biological component is cholesterol, it is preferable that the oxidoreductase is a cholesterol dehydrogenase or a cholesterol oxidase. The content of the oxidoreductase in a case in which the reagent for biological component concentration measurement includes an oxidoreductase is not particularly limited, and the content can be selected as appropriate according to the amount of the tetrazolium salt. The electron carrier is not particularly limited, and any known electron carrier may be used. Specific examples include a diaphorase, phenazine methosulfate (PMS), 1-methoxy-5-methylphenazinium methyl sulfate (1-Methoxy PMS or m-PMS), nicotinamide adenine dinucleotide phosphate (NADPH), and nicotinamide adenine dinucleotide (NADH). Here, the electron carriers may be used singly or in combination of two or more kinds thereof. The content of the electron carrier in a case in which the reagent for biological component concentration measurement includes an electron carrier is not particularly limited, and the content can be selected as appropriate according to the amount of the tetrazolium salt. For example, the content of the electron carrier is preferably 0.05% to 10% by mass, and more preferably 0.1% to 5% by mass, with respect to the tetrazolium salt. With such an amount, the reduction reaction can be carried out more efficiently.

In regard to the description given above, it is preferable that the reagent for biological component concentration measurement further includes a transition metal compound and an oxidoreductase, and it is more preferable that the reagent further includes a transition metal compound, an oxidoreductase, and an electron carrier. That is, according to a preferred embodiment of the present disclosure, the reagent for biological component concentration measurement includes the 2-substituted benzothiazolyl-3-substituted phenyl-5-substituted sulfonated phenyl-2H-tetrazolium salt of the present disclosure, a transition metal compound, and an oxidoreductase. Furthermore, according to a more preferred embodiment of the present disclosure, the reagent for biological component concentration measurement includes the 2-substituted benzothiazolyl-3-substituted phenyl-5-substituted sulfonated phenyl-2H-tetrazolium salt of the present disclosure, a transition metal compound, an oxidoreductase, and an electron carrier. Here, in a case in which the biological component is β-D-glucose, the transition metal compound is nickel chloride, the oxidoreductase is a glucose dehydrogenase that uses flavin adenine dinucleotide as a coenzyme (GDH-FAD), and the electron carrier is 1-methoxy-5-methylphenazium methyl sulfate (m-PMS), first, β-D-glucose and m-PMS are subjected to the action of GDH-FAD to become gluconic acid and reduced m-PMS, respectively, and this reduced m-PMS and the tetrazolium salt produce m-PMS and formazan. Thus, color development occurs. Furthermore, this formazan forms a chelate compound with nickel ion, and thereby the maximum absorption wavelength is shifted toward the longer wavelength range side (for example, 600 nm or greater). For this reason, when the reagent for biological component concentration measurement of the present disclosure is used, the influence exerted by the absorption of hemoglobin can be reduced, and therefore, the biological component concentration in a biological sample, particularly even in a whole blood sample, can be measured with high sensitivity.

The form of use of the reagent for biological component concentration measurement is not particularly limited and may be in any one of a solid form, a gel form, a sol form, and a liquid form. The reagent for biological component concentration measurement may also include water, a buffer, a surfactant, and the like. Here, the buffer is not particularly limited, and those buffers generally used at the time of measuring a biological component concentration can be similarly used. Specific examples that can be used include "GOOD" buffers such as a phosphate buffer, a citrate buffer, a citrate-phosphate buffer, a tris(hydroxymethyl)aminomethane HCl buffer (Tris hydrochloride buffer), an MES buffer (2-morpholinoethane sulfonate buffer), a TES buffer (N-tris(hydroxymethyl)methyl-2-aminoethanesulfonate buffer), an acetate buffer, a MOPS buffer (3-morpholinopropane sulfonate buffer), a MOPS-NaOH buffer, a HEPES buffer (4-(2-hydroxyethyl)-1-piperazinethane sulfonate buffer), and a HEPES-NaOH buffer; amino acid-based buffers such as a glycine-hydrochloride buffer, a glycine-NaOH buffer, a glycylglycine-NaOH buffer, and a glycylglycine-KOH buffer; boric acid-based buffers such as a Tris borate buffer, a borate-NaOH buffer, and a borate buffer; and an imidazole buffer. Among these, a phosphate buffer, a citrate buffer, a citrate-phosphate buffer, a Tris hydrochloride buffer, a MES buffer, a citrate buffer, a MOPS buffer, and a HEPES-NaOH buffer are preferred. Here, the concentration of the buffer is not particularly limited; however, it is preferable that the concentration is 0.01 to 1.0 M. Meanwhile, the concentration of the buffer according to the present disclosure refers to the concentration of a buffer included in an aqueous solution (M, mol/L). Furthermore, it is preferable that the pH of the buffer solution does not have any action on the biological component. From the above-described viewpoint, it is preferable that the pH of the buffer solution is near neutrality, for example, about 5.0 to 8.0. In a case in which the reagent for biological component concentration measurement is liquid, the concentration of the tetrazolium salt is not particularly limited as long as it is a concentration at which the concentration of a desired biological component can be measured; however, it is preferable that the tetrazolium salt is included in a sufficient amount with respect to the abundance of the desired biological component. When the above-described viewpoints and the conventional biological component concentrations to be measured are taken into consideration, the concentration of the tetrazolium salt is preferably 0.01 to 0.2 mol/L, and more preferably 0.05 to 0.1 mol/L, with respect to the reagent for biological component concentration measurement. With such an amount, the tetrazolium salt reacts with substantially the entire amount (for example, 95 mol % or more, preferably 98 mo % or more, and particularly preferably 100 mol %) of the biological component included in a biological sample. Therefore, the desired biological component concentration can be measured accurately and rapidly with satisfactory sensitivity.

By using the reagent for biological component concentration measurement of the present disclosure, the concentration of a particular biological component included in a biological sample can be measured with satisfactory sensitivity. Here, the measurement method is not particularly limited and can be selected as appropriate according to the type of the biological component as an object of measurement. For example, in a case in which the biological component is β-D-glucose, and the oxidoreductase is a glucose dehydrogenase (GDH), glucose is oxidized by GDH, thereby gluconic acid is produced, and reduction of a coenzyme of GDH or an electron carrier substance at that time is utilized. Thus, specifically, the measurement methods are roughly classified into methods of photometrically measuring the degree of coloring of the consequently reduced tetrazolium salt (therefore, formazan or a chelate compound of formazan and a transition metal ion) (colorimetric methods), and methods of measuring the electric current produced by an oxidation-reduction reaction (electrode methods). Among the methods described above, the measurement of the blood sugar level according to a colorimetric method has advantages such as easy implementation of correction using the hematocrit value at the time of calculating the blood sugar level, and simple and easy production process. Therefore, the reagent for biological component concentration measurement can be suitably used for a colorimetric method. Particularly, in the case of measuring the glucose concentration in a whole blood sample, a colorimetric method is preferably used.

The reagent for biological component concentration measurement of the present disclosure may be used in the form as received for the measurement of a biological component concentration; however, the reagent may also be incorporated into a chip for biological component concentration measurement. That is, the present disclosure also provides a chip for biological component concentration measurement including the reagent for biological component concentration measurement of the present disclosure (hereinafter, also simply referred to as "sensor chip"). The reagent or method for biological component concentration of the present disclosure can be incorporated into an automatic analyzer, an analytic kit, a simplified blood glucose meter, or the like and used for common clinical examinations. Furthermore, it is also possible to incorporate the reagent of the present disclosure into a commercially available biosensor. In the case of incorporating the reagent for biological component concentration measurement into a chip for biological component concentration measurement, the content of the reagent per chip is not particularly limited, and an amount that is conventionally used in the pertinent art can be similarly employed. However, it is preferable that the tetrazolium salt is included in a sufficient amount with respect to the abundance of a desired biological component. When the above-described viewpoints and the conventional biological component concentrations to be measured are taken into consideration, the concentration of the tetrazolium salt is preferably 3 to 50 nmol, and more preferably 10 to 30 nmol, per chip. With such an amount, the tetrazolium salt reacts according to the amounts of substantially all the biological components included in a biological sample. Therefore, a desired biological component concentration can be measured accurately and rapidly with satisfactory sensitivity.

In the following description, the form of the sensor chips of the present disclosure used for measuring the blood sugar level by a colorimetric method (colorimetric blood glucose meter) will be explained with reference to the drawings. However, the present disclosure is characterized by the use of the reagent for biological component concentration measurement of the present disclosure, and the structure of the chip is not particularly limited. Therefore, the reagent for biological component concentration measurement of the present disclosure may also be applied to a commercially available sensor chip or the chips described in WO 2014/04970 A, WO 2016/051930 A, and the like. Similarly, in the embodiment described below, a specific form of a chip intended for the measurement of the blood sugar level will be explained; however, the sensor chip is not limited to the relevant use and can be applied in the same manner, or after being appropriately modified, to other use applications.

FIG. 9 is a plan view schematically illustrating a blood glucose meter used for the detection of glucose (blood sugar) using the sensor chip according to the present embodiment.

In FIG. 9, the blood glucose meter 10 is configured as an instrument for measuring glucose (blood sugar) in a blood sample. This blood glucose meter 10 can be used mainly for personal use, in which the instrument is operated by the user (testee). The user can implement the blood sugar management of oneself by measuring the preprandial blood sugar. Furthermore, a health care worker may use the blood glucose meter 10 in order to evaluate the health status of a testee, and in this case, the blood glucose meter 10 may be configured to be installable in a medical facility or the like by being modified as appropriate.

The blood glucose meter 10 employs the principle of a colorimetric method, by which the content of glucose in a blood sample (blood sugar level) is photometrically measured. Particularly, this blood glucose meter 10 performs the measurement of blood sugar by means of a transmission type measuring unit 14 that irradiates an analysis sample (blood) with measuring light having a predetermined wavelength and receiving the light transmitted through the analysis sample.

In the blood glucose meter 10, a sensor chip 12 having blood incorporated therein is mounted, or blood is incorporated into the sensor chip 12 in a state of having the sensor chip 12 mounted, and thereby glucose is detected using the measuring unit 14. The sensor chip 12 may be configured into a disposable type that is disposed of after every single measurement. Meanwhile, it is preferable that the blood glucose meter 10 is configured into a portable and tenacious instrument so that the user can repeat measurement simply and easily.

Figure 10:
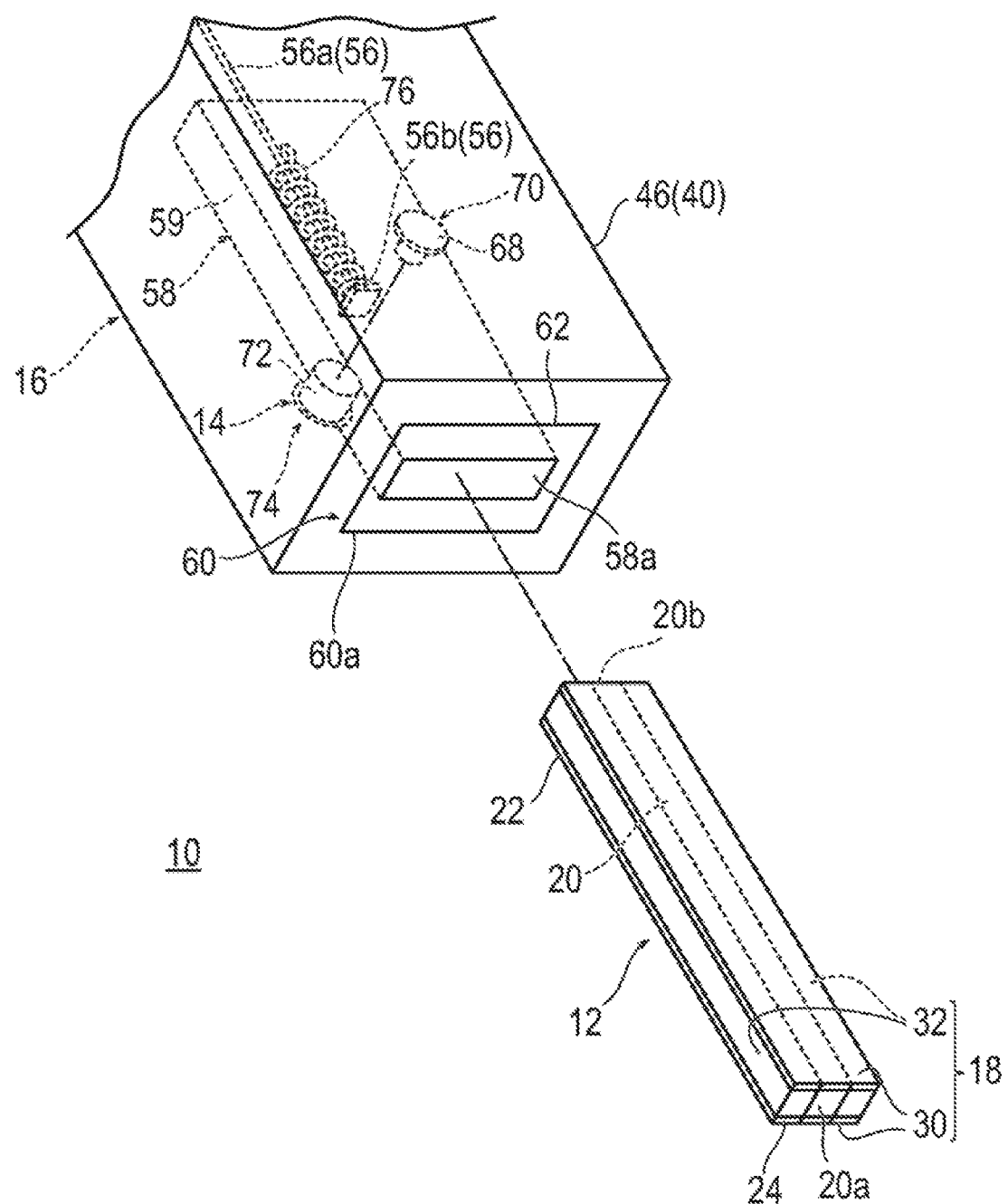
FIG. 10 is a perspective view illustrating a magnification of the sensor chip and a photometric unit of the apparatus main body of FIG. 9.

The sensor chip 12 includes, as illustrated in FIG. 10, a chip main body 18 formed into a plate shape, and a cavity 20 (cavity for liquid) extending in the planar direction of the plate surface in the interior of the chip main body 18.

As illustrated in FIG. 10, the chip main body 18 is formed into a rectangular shape having long edges 22 that are elongated in the direction of plugging and unplugging of the blood glucose meter 10 (direction of the front end and the base end of the blood glucose meter 10, that is, direction B) and also having short edges 24 that are short in direction A. For example, it is desirable that the length of the long edges 22 of the chip main body 18 is set to a length that is two or more times the length of the short edges 24. Thereby, in the sensor chip 12, a sufficient amount of insertion is secured for the blood glucose meter 10.

Furthermore, the thickness of the chip main body 18 is formed to be very small (thin) compared to the lateral surfaces formed into a rectangular shape (in FIG. 10, it is deliberately depicted such that the chip main body has a sufficient thickness). For example, the thickness of the chip main body 18 is preferably set to be 1/10 or less of the length of the short edges 24. The thickness of this chip main body 18 may be designed as appropriate according to the shape of the insertion port 58 of the blood glucose meter 10.

In the sensor chip 12, the chip main body 18 is configured to include a pair of plate pieces 30 and a pair of spacers 32 so that the sensor chip 12 has a cavity 20.

Figure 11:
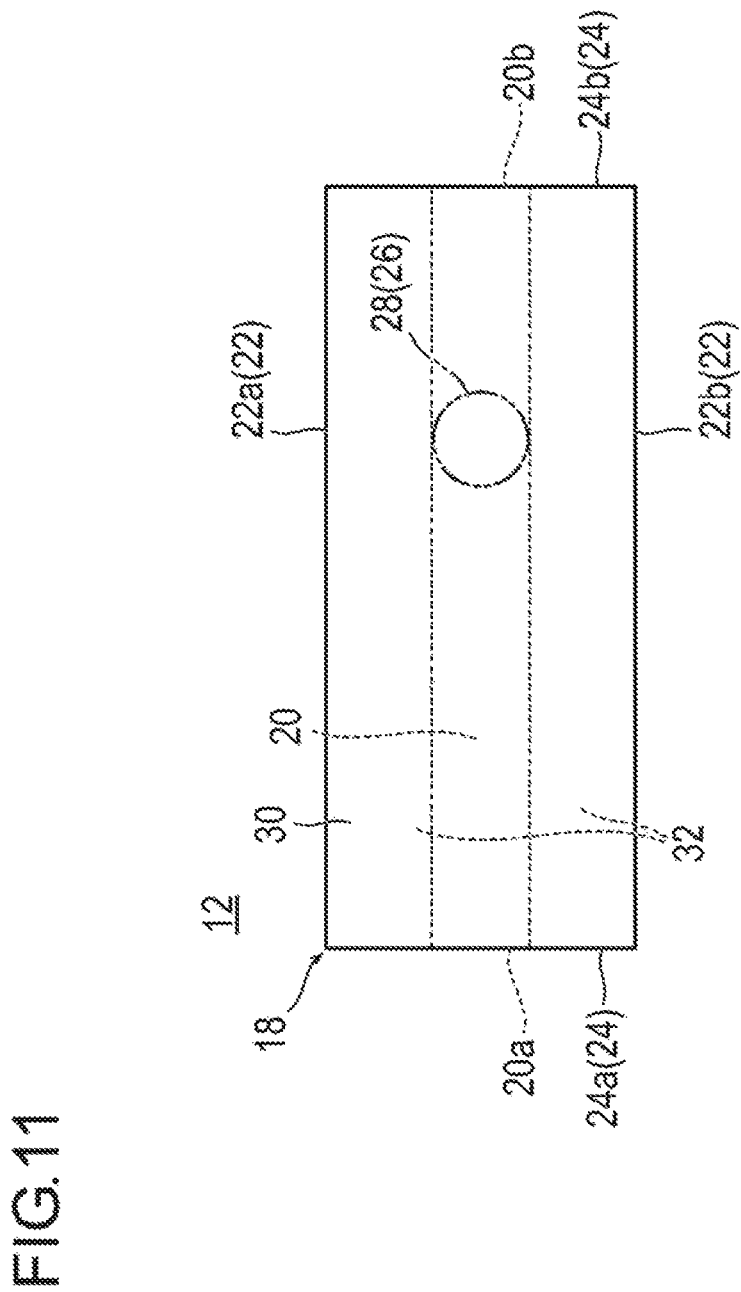
FIG. 11 is a lateral view illustrating the sensor chip of FIG. 9.

FIG. 11 is a top view diagram illustrating the sensor chip of FIG. 9. In FIG. 11, the corners of the chip main body 18 are sharp; however, for example, the corners may be formed into round corners. Furthermore, the chip main body 18 is not limited to a thin plate shape, and the shape may be definitely designed freely. For example, the chip main body 18 may be formed into a square shape, another polygonal shape, a circular shape (including an elliptical shape), or the like as viewed from the top.

The cavity 20 provided inside the chip main body 18 is positioned in the middle in the minor axis direction of the chip main body 18, and is formed into a linear shape along the longitudinal direction of the chip main body 18. This cavity 20 extends into the front end port 20a formed at the front end edge 24a of the chip main body 18 and the base end port 20b formed at the base end edge 24b, respectively, and the cavity is in communication with the outside of the chip main body 18. In the cavity 20, when the user's blood is introduced thereinto through the front end port 20a, the blood can be caused to flow along the direction of extension based on the capillary phenomenon. The quantity of the blood that flows through the cavity 20 is small, and even if the blood moves to the base end port 20b, leakage is suppressed by tension. On the side of the base end edge 24b of the chip main body 18, an absorptive portion that absorbs blood (for example, the spacers 32 that will be described below is formed from a porous material only on the base end side) may be provided.

Furthermore, at a predetermined position of the cavity 20 (for example, a position slightly shifted to the base end from the midpoint between the front end port 20a and the base end port 20b illustrated in FIG. 11), a measuring object portion 28 in which a reagent (indicator reagent) 26 that develops a color correspondingly to the glucose (blood sugar) concentration in the blood by reacting with glucose in the blood (blood sugar) is applied, and measurement is achieved by the blood glucose meter 10, is provided. The blood flowing through the cavity 20 in the direction of the base end comes into contact with the reagent 26 applied on the measuring object portion 28, and the measuring object portion 28 is colored as the blood reacts with the reagent 26. Meanwhile, in the longitudinal direction of the cavity 20, the position of application of the reagent 26 and the measuring object portion 28 may be shifted from each other, and for example, a reaction part applied with the reagent 26 may be provided on the upstream side in the blood flow direction of the measuring object portion 28.

In the sensor chip 12, the chip main body 18 is composed of a pair of plate pieces 30 and a pair of spacers 32 so as to have the cavity 20 described above. The plate pieces 30 that form a pair are respectively formed into the rectangular shape described above as viewed from the lateral side and are disposed in a mutually laminating direction. That is, a pair of plate pieces 30 constitutes the two lateral surfaces (upper surface and lower surface) of the chip main body 18. The plate thickness of each plate piece 30 is very small, and for example, the plate thickness may be set to have the same dimension of about 5 to 50 µm. The thickness of two (a pair) of the plate pieces 30 may be different from each other.

The pair of plate pieces 30 has a strength that maintains the plate shape and does not undergo plastic deformation even if a certain degree of pressing force is applied in a direction orthogonally intersecting the planar direction. Furthermore, each of the plate pieces 30 includes a transparent part or a translucent portion so that the measuring light can be transmitted. Furthermore, it is preferable that each of the plate pieces 30 is formed on a flat plate surface having appropriate hydrophilicity so that blood can be caused to flow in the cavity 20.

The material that constitutes the plate pieces 30 is not particularly limited; however, a thermoplastic resin material, glass, quartz, or the like may be applied. Examples of the thermoplastic resin material include polymeric materials such as a polyolefin (for example, polyethylene or polypropylene), a cycloolefin polymer, a polyester (for example, polyethylene terephthalate or polyethylene naphthalate), polyvinyl chloride, polystyrene, an ABS resin, an acrylic resin, a polyamide, and a fluororesin; and mixtures thereof.

Furthermore, a pair of spacers 32 is disposed so as to be interposed between the pair of plate pieces 30, and the spacers are strongly adhered to the respective facing surfaces of the plate pieces 30 by means of a predetermined joining means (adhesive or the like). That is, the spacers 32 are members that are disposed between the plate pieces 30 constituting a pair so as to separate apart the plate pieces, and thereby form the cavity 20 between the pair of plate pieces 30 and the pair of spacers 32 themselves. In this case, one of the spacers 32 is disposed so as to come into contact with the upper long edge 22a of the chip main body 18 in FIG. 11 and to extend in the direction from the front end to the base end along this upper long edge 22a. The other spacer 32 is disposed so as to come into contact with the lower long edge 22b of the chip main body 18 in FIG. 11 and to extend in the direction from the front end to the base end along this lower long edge 22b.

The material (base material) that constitutes a pair of spacers 32 is not particularly limited; however, examples include various elastomers such as a styrene-based elastomer, a polyolefin-based elastomer, a polyurethane-based elastomer, a polyester-based elastomer, a polyamide-based elastomer, a polybutadiene-based elastomer, a trans-polyisoprene-based elastomer, a fluorine rubber-based elastomer, and a chlorinated polyethylene-based elastomer. Alternatively, in addition to the thermoplastic elastomers, various materials capable of elastic deformation may be applied, or structures such as a porous body (for example, sponge) capable of elastic deformation may also be applied. Furthermore, the spacers may also be applied as spacers 32 having, on one surface or both surfaces of the base material, an adhesive that adheres the plate pieces 30 by being brought into a cured state or a semicured state between the pair of plate pieces 30. Furthermore, the spacers 32 may also be configured such that the spacers contain the reagent 26 and elute the reagent 26 into the cavity 20.

The plate pieces 30 or the spacers 32 may be hydrophilization-treated materials. Examples of the method of performing hydrophilization treatment include a method of applying an aqueous solution containing a hydrophilic polymer such as a surfactant, polyethylene glycol, polypropylene glycol, hydroxypropyl cellulose, a water-soluble silicone, polyacrylic acid, polyvinylpyrrolidone, or polyacrylamide by an immersion method, a spraying method, or the like; and methods of plasma irradiation, glow discharge, corona discharge, ultraviolet irradiation (for example, excimer light irradiation), and the like. These methods may be used singly or in combination.

Next, the apparatus main body 16 of the blood glucose meter 10 will be explained. As illustrated in FIG. 9, the blood glucose meter 10 has a case 40 that constitutes the external appearance. The case 40 includes a box body 44 that accommodates a control unit 42 of the blood glucose meter 10 inside the box body into a size that can be easily gripped and operated by the user; and a cylindrical-shaped photometric unit 46 that protrudes from one edge (front end side) of the box body 44 to the front end direction and accommodates a photometric measuring unit 14 in the inside. Furthermore, on the upper surface of the box body 44, a power supply button 48, an operation button 50, and a display 52 are provided, and on the upper surface of the photometric unit 46, an ejection lever 54 is provided.

The power supply button 48 switches the operation start and stop of the blood glucose meter 10 through the operation of the user. In regard to the blood glucose meter 10 in an activating state, the operation button 50 functions as an operation unit that performs measurement or display of the blood sugar level based on the operation of the user, switches the display of the measurement results (including the past measurement results), and the like. The display 52 is configured to include liquid crystals, organic EL, or the like, and displays the information supplied to the user in a measurement operation, such as the display of measurement results or the display of errors.

The ejection lever 54 is provided so as to be movable in the direction from the front end to the base end, and ejection level releases the lock of an ejection pin that is not shown in the diagram and is provided inside the photometric unit 46, and thereby enables the ejection pin to move in the direction toward the front end.

On the other hand, the photometric unit 46 of the apparatus main body 16 is extended long from the box body 44 in the direction toward the front end, in order to press the front end with the user's finger or the like. As illustrated in FIG. 10, a chip mounting part 60 having an insertion port 58; and a measuring unit 14 that photometrically detects glucose (blood sugar) in the blood are provided in this photometric unit 46.

Figure 12A:
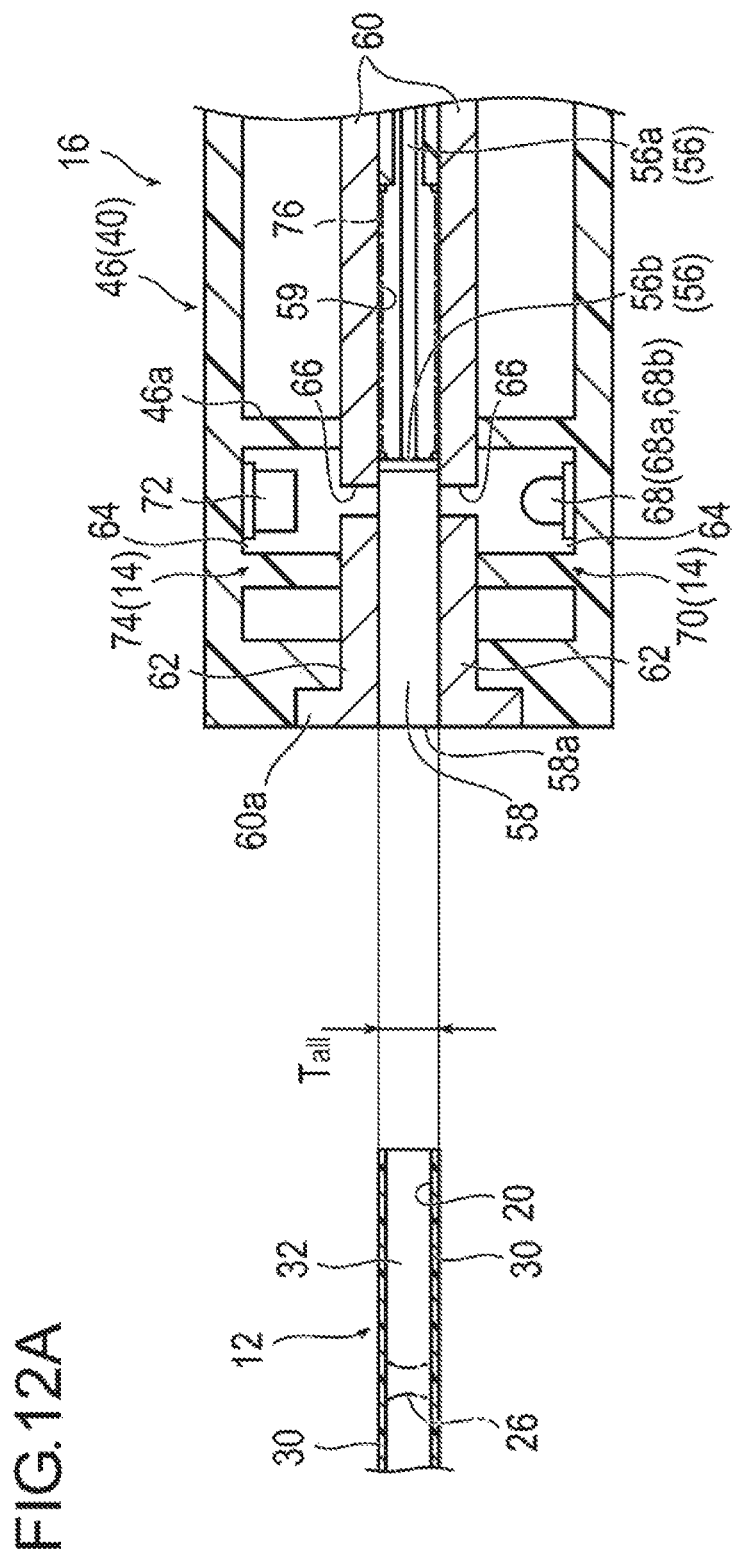
FIG. 12A is a first plan view illustrating the operation of mounting of the sensor chip and the apparatus main body of FIG. 9.

The chip mounting part 60 is formed from a material having high hardness (rigidity) (for example, stainless steel) into a cylindrical shape that includes a flange portion 60a protruding outward on the front end side and has a predetermined length in the axial direction. This chip mounting part 60 is positioned and fixed over the front end surface and the axial center (central portion) of the photometric unit 46 formed from a resin material. On the inner surface of the photometric unit 46, a fixing wall 46a that strongly fixes the chip mounting part 60 is formed in a protruding manner, as illustrated in FIG. 12A.

Regarding the material that constitutes the chip mounting part 60, for example, a material that is hard, does not easily undergo dimensional change, is not likely to be abraded even if plugging and unplugging of the sensor chip is repeatedly performed, and can be processed with satisfactory dimensional accuracy, such as a metal such as stainless steel or titanium; alumite coating-treated aluminum; a liquid crystal polymer; a plastic having a filler such as glass or mica incorporated therein; a plastic having its surface covered with a cured coating film by nickel plating or the like; carbon fibers; or fine ceramics, may be mentioned. Among these, when a metal material is applied, an insertion port 58 can be molded easily with high dimensional accuracy at the time of producing the chip mounting part 60 (injection molding, press molding, or the like). Meanwhile, the apparatus main body 16 may be integrally molded with the chip mounting part 60 by configuring the photometric unit 46 itself with a hard material (for example, a metal material).

At the axial center of the chip mounting part 60, an insertion port 58 is provided as the axis center is surrounded by walls 62 of this chip mounting part 60. The insertion port 58 is formed into a rectangular shape having a cross-section that is long in the direction of insertion (direction B) and is short in the lateral width direction (direction A). The insertion port 58 has a predetermined depth from the front end surface toward the inner side (direction to the base end) in a state in which the chip mounting part 60 is fixed to the photometric unit 46.

On the front end side of the chip mounting part 60, an insertion opening 58a that is connected to the insertion port 58 and is also in communication with the outside, is formed. The dimension in the direction of insertion (direction B) of this insertion opening 58a coincides with the dimension of the short edge 24 of the sensor chip 12 (length in direction A). Furthermore, the dimension in the lateral width direction of the insertion opening 58a, that is, the distance between a pair of walls 62 constituting the side surfaces of the insertion port 58, is substantially the same as the thickness in the direction of lamination of the sensor chip 12 (Tall in FIG. 12A), as illustrated in FIG. 12A.

The chip mounting part 60 forms, together with the fixing wall 46a of the photometric unit 46, a pair of device accommodating space 64 at a position in the middle of the extension of the insertion port 58 (port for measurement 59). The pair of device accommodating spaces 64 is a portion of the measuring unit 14, and the spaces are provided at positions facing each other, with the insertion port 58 disposed therebetween. The device accommodating spaces are each in communication with the port for measurement 59 through a light guide 66 formed by the chip mounting part 60.

The measuring unit 14 constitutes a light emitting unit 70 by accommodating a light emitting device 68 in one of the device accommodating spaces 64, and constitutes a light receiving unit 74 by accommodating a light receiving device 72 in the other device accommodating space 64. The light guides 66 of the chip mounting part 60 plays the role of a so-called aperture by being formed into a circular-shaped hole having an appropriate diameter.

The light emitting device 68 of the light emitting unit 70 includes a first light emitting device 68a that irradiates the sensor chip 12 with measuring light having a first wavelength; and a second light emitting device 68b that irradiates the sensor chip 12 with measuring light having a second wavelength different from the first wavelength (not illustrated in FIG. 10). The first light emitting device 68a and the second light emitting device 68b are provided in parallel at the positions facing the light guides 66 of the device accommodating spaces 64.

The light emitting device 68 (first and second light emitting devices 68a and 68b) can be constructed from light emitting diodes (LED). The first wavelength is a wavelength for detecting the coloration density of the reagent 26 in accordance with the amount of blood sugar, and for example, the first wavelength is 600 nm to 680 nm. The second wavelength is a wavelength for detecting the red blood cell concentration in the blood, and for example, the second wavelength is 510 nm to 540 nm. The control unit 42 inside the box body 44 supplies a driving current and thereby causes the first and second light emitting devices 68a and 68b to emit light respectively at predetermined timings. In this case, the blood sugar level obtainable from the coloration density is corrected using the hematocrit value obtainable from the red blood cell concentration, and the blood sugar level is determined. Meanwhile, it is also acceptable to compensate for noises attributed to blood cells by further making measurements at different measurement wavelengths.

The light receiving unit 74 is configured by disposing one light receiving device 72 at a position facing the light guide 66 of the device accommodating space 64. This light receiving unit 74 is to receive the transmitted light coming from the sensor chip 12, and for example, the light receiving unit 74 can be composed of a photodiode (PD).

Furthermore, the at the bottom (base end surface) of the insertion port 58, the ejection pin 56 (ejection part) connected to the ejection lever 54 is provided. The ejection pin 56 includes a rod portion 56a extending along the axial direction of the photometric unit 46; and a receptor 56b having a large diameter on the outer side in the circumferential direction at the tip of the rod portion 56a. The receptor 56b is brought into contact with the base end edge 24b of the sensor chip 12 inserted into the insertion port 58. Furthermore, between the bottom of the insertion port 58 and the receptor 56b of the ejection pin 56, a coil spring 76 surrounding the ejection pin 56 in a non-contacting manner is provided. The coil spring 76 elastically supports the receptor 56b of the ejection pin 56.

When insertion of the sensor chip 12 is completed, as illustrated in FIG. 12B, the measuring object portion 28 of the sensor chip 12 is disposed at the position that overlaps with the light guides 66.

The ejection pin 56 is displaced in the direction toward the base end as the receptor 56b is pushed along with the insertion of the sensor chip 12 by the user, and the ejection pin 56 is locked (fixed) by a locking mechanism that is provided inside the case 40 and is not shown in the diagram. The coil spring 76 elastically contracts along with the displacement of the receptor 56b. Then, when the ejection pin 56 slightly moves as a result of the user's operation of the ejection lever 54, the lock of the locking mechanism is released, and the sensor chip slides in the direction toward the front end by the elastic restoring force of the coil spring 76. Thereby, the sensor chip 12 is pushed out to the ejection pin 56 and is taken out through the insertion port 58.

Returning to FIG. 9, the control unit 42 of the apparatus main body 16 is composed of a control circuit having, for example, a computation unit, a memory unit, and an input/output unit. For this control unit 42, a well-known computer can be applied. The control unit 42 derives and controls the measuring unit 14 under, for example, the user's operation of the operation button 50, detects and calculates the glucose level in blood, and displays the blood sugar level thus calculated, on the display 52.

For example, in regard to a blood glucose meter 10 that transmits measuring light through a sensor chip 12 and thereby measures an object of analysis (for example, glucose), the control unit 42 calculates the measurement results based on the Beer-Lambert law expressed by the following Formula (A).

[Math. 1]

$$\log_{10}(l_1/l_0) = -\alpha L \qquad (A)$$

In Formula (A) shown above, $l_0$ represents the intensity of light before entering a blood sample; $l_1$ represents the intensity of light after being emitted from the blood sample; α represents the extinction coefficient; and L represents the distance (cell length) through which the measuring light passes.

EXAMPLES

The effects of the present disclosure will be described using the following Examples and Comparative Examples. However, the technical scope of the present disclosure is not intended to be limited only to the following Examples. In the Examples described below, unless particularly stated otherwise, the operation was carried out at room temperature (25° C.). Furthermore, unless particularly stated otherwise, the units "percent (o)" and "parts" mean "percent by mass (mass %)" and "parts by mass", respectively.

Example 1: Synthesis of Tetrazolium Compound 1

A compound (tetrazolium compound 1) having the following structure was synthesized according to the following method.

Tetrazolium compound 1

[Chemical Formula 14]

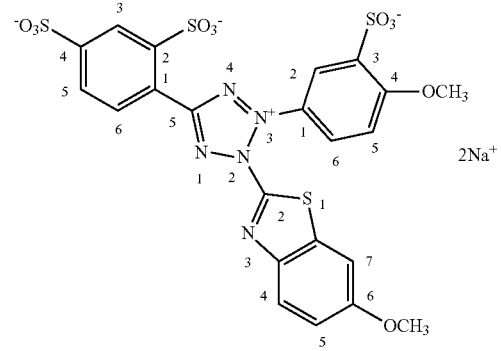

1. Synthesis of Hydrazone Compound 1

1.59 g of disodium 4-formylbenzene-1,3-disulfonate (manufactured by Tokyo Chemical Industry Co., Ltd.) and 1.0 g of (6-methoxy-1,3-benzothiazol-2-yl) hydrazine (also known as 2-hydrazino-6-methoxy-1,3-benzothiazole) (manufactured by Santa Cruz Biotechnology, Inc.) were suspended in 60 mL of RO water. This suspension was heated and stirred in a water bath at 60° C. for 2 hours under the acidity of acetic acid. After completion of the heating and stirring, the solvent was removed. This residue was washed with isopropanol, and then a precipitate was separated by filtration. This precipitate was dried in a draught, and thereby hydrazone compound 1 was obtained. 1.8 g of the compound was recovered, and the yield was 70% by mass.

2. Synthesis of Formazan Compound 1

0.76 g of the hydrazone compound 1 of the above section 1. was dissolved in a mixed liquid of 10 mL of RO water and 10 mL of DMF, and thereby a solution of hydrazone compound 1 was produced. 0.264 g of p-anisidine-3-sulfonic acid (manufactured by Tokyo Chemical Industry Co., Ltd.) was suspended in 4.09 mL of RO water, and 130 μL of 10 N NaOH was added to the suspension to dissolve therein. While this solution as maintained at 0° C., 280 μL of 9.6 N HCl was added thereto, a sodium nitrite solution was added dropwise thereto, and thus diazotization was performed. This diazotized solution was maintained at −20° C., and this solution was added dropwise to the hydrazone compound 1 solution. After completion of the dropwise addition, 300 μL of 10 N NaOH was added dropwise thereto, the mixture was stirred at room temperature (25° C.) for 2 hours, and thus a solution including formazan compound 1 (formazan compound 1 solution) was produced. The pH of this formazan compound 1 solution was adjusted to neutrality with 9.6 N HCl, and the solvent was removed. The residue thus obtained was washed with isopropanol, and then a precipitate was separated by filtration. This precipitate was dried, and formazan compound 1 was obtained.

3. Purification of Formazan Compound 1 and Synthesis of Tetrazolium Compound 1

The formazan compound 1 of the above section 2. was dissolved in 10 mL of RO water, and thereby a formazan compound 1 solution was produced. A disposable column (size: 20 cm×5 cm) was packed with a filler for column chromatography (manufactured by NACALAI TESQUE, INC., COSMOSIL 40$C_{18}$-PREP), and the disposable column was mounted in a column preparative separation system (manufactured by BÜCHI Labortechnik AG, trade name: SEPACORE). The formazan compound 1 solution was purified using this column system. The solvent of a fraction thus collected was removed, and to the solid component thus obtained, 15 mL of methanol, 250 μL of 9.6 N HCl, and 5 mL of a 15% ethyl nitrite ($CH_3CH_2NO_2$)-ethanol solution were added. The mixture was stirred for 72 hours at room temperature (25° C.) in the dark.

4. Collection of Tetrazolium Compound 1

Diethyl ether was added to the reaction solution of the above section 3., and thereby tetrazolium compound 1 was precipitated. This precipitate was centrifuged, the supernatant was removed, and then the residue was further washed with diethyl ether. The precipitate thus obtained was dried in a draught, and thus tetrazolium compound 1 was obtained (120 mg, yield: 11.8% by mass).

Example 2: Synthesis of Tetrazolium Compound 2

A compound having the following structure (tetrazolium compound 2) was synthesized according to the following method.

Tetrazolium compound 2

[Chemical Formula 15]

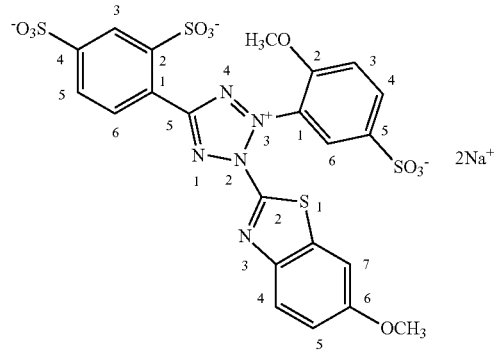

1. Synthesis of Hydrazone Compound 1

Hydrazone compound 1 was synthesized in the same manner as in 1. Synthesis of hydrazone compound 1 of Example 1.

2. Synthesis of Formazan Compound 2

0.76 g of the hydrazone compound 1 was dissolved in a mixed liquid of 10 mL of RO water and 10 mL of DMF, and thereby a hydrazone compound 1 solution was produced. 0.264 g of o-anisidine-5-sulfonic acid (manufactured by Tokyo Chemical Industry Co., Ltd.) was suspended in 4.09 mL of RO water, and 130 μL of 10 N NaOH was added to the suspension to dissolve therein. While this solution was maintained at 0° C., 280 μL of 9.6 N HCl was added to the solution, a sodium nitrite solution was added dropwise thereto, and diazotization was performed. This diazotized solution was maintained at −20° C., and this solution was added dropwise to the hydrazone compound 1 solution. After completion of the dropwise addition, 300 μL of 10 N NaOH was added dropwise thereto, the mixture was stirred at room temperature (25° C.) for 2 hours, and thereby a solution including formazan compound 2 (formazan compound 2 solution) was produced. The pH of this formazan compound 2 solution was adjusted to neutrality with 9.6 N HCl, and the solvent was removed. The residue thus obtained was washed with isopropanol, and then a precipitate was separated by filtration. The precipitate thus obtained was dried, and thereby formazan compound 2 was obtained.

3. Purification of Formazan Compound 2 and Synthesis of Tetrazolium Compound 2

The formazan compound 2 of the above section 2. was dissolved in 10 mL of RO water, and thereby a formazan compound 2 solution was produced. A disposable column (size: 20 cm×5 cm) was packed with a filler for column chromatography (manufactured by NACALAI TESQUE, INC., COSMOSIL 40$C_{18}$-PREP), and the disposable column was mounted in a column preparative separation system (manufactured by BÜCHI Labortechnik AG, trade name: SEPACORE). The formazan compound 2 solution was purified using this column system. The solvent of a red fraction thus collected was removed, and to a solid component thus obtained, 15 mL of methanol, 250 μL of 9.6 N HCl, and 5 mL of a 15% ethyl nitrite ($CH_3CH_2NO_2$)-ethanol solution were added. The mixture was stirred for 72 hours at room temperature (25° C.) in the dark.

4. Collection of Tetrazolium Compound 2

Diethyl ether was added to 5 mL of the reaction solution of the above section 3., and thereby tetrazolium compound 2 was precipitated. The precipitate was centrifuged, the supernatant was removed, and then the residue was further washed with diethyl ether. This precipitate was dried in a draught, and thus tetrazolium compound 2 was obtained.

Example 3: Synthesis of Tetrazolium Compound 3

A compound having the following structure (tetrazolium compound 3) was synthesized according to the following method.

Tetrazolium compound 3

[Chemical Formula 16]

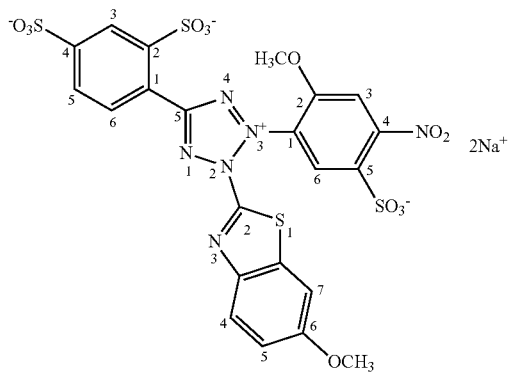

1. Synthesis of Hydrazone Compound 1

Hydrazone compound 1 was synthesized in the same manner as in 1. Synthesis of hydrazone compound 1 of Example 1.

2. Synthesis of Formazan Compound 3

0.76 g of the hydrazone compound 1 was dissolved in a mixed liquid of 10 mL of RO water and 10 mL of DMF, and thereby a hydrazone compound 1 solution was produced. 0.351 g of 2-methoxy-4-nitroaniline-5-sulfonic acid sodium salt (manufactured by Goni Chemical Industry Co., Ltd.) was dissolved in 5.0 mL of RO water. While this solution was maintained at 0° C., 280 µL of 9.6 N HCl was added to the solution, a sodium nitrite solution was added dropwise thereto, and diazotization was performed. This diazotized solution was maintained at −20° C., and this solution was added dropwise to the hydrazone compound 1 solution. After completion of the dropwise addition, 300 µL of 10 N NaOH was added dropwise thereto, the mixture was stirred at room temperature (25° C.) for 2 hours, and thereby a solution including formazan compound 3 (formazan compound 3 solution) was produced. The pH of this formazan compound 3 solution was adjusted to neutrality with 9.6 N HCl, and the solvent was removed. The residue thus obtained was washed with isopropanol, and then a precipitate was separated by filtration. The precipitate thus obtained was dried, and thereby formazan compound 3 was obtained.

3. Purification of Formazan Compound 3 and Synthesis of Tetrazolium Compound 3

The formazan compound 3 of the above section 2. was dissolved in 10 mL of RO water, and thereby a formazan compound 3 solution was produced. A disposable column (size: 20 cm×5 cm) was packed with a filler for column chromatography (manufactured by NACALAI TESQUE, INC., COSMOSIL 40C$_{18}$-PREP), and the disposable column was mounted in a column preparative separation system (manufactured by BÜCHI Labortechnik AG, trade name: SEPACORE). The formazan compound 3 solution was purified using this column system. The solvent of a red fraction thus collected was removed, and to a solid component thus obtained, 15 mL of methanol, 250 µL of 9.6 N HCl, and 5 mL of a 15% ethyl nitrite ($CH_3CH_2NO_2$)-ethanol solution were added. The mixture was stirred for 72 hours at room temperature (25° C.) in the dark.

4. Collection of Tetrazolium Compound 3

Diethyl ether was added to 5 mL of the reaction solution of the above section 3., and thereby tetrazolium compound 3 was precipitated. The precipitate was centrifuged, the supernatant was removed, and then the residue was further washed with diethyl ether. This precipitate was dried, and thus tetrazolium compound 3 was obtained.

Example 4: Synthesis of Tetrazolium Compound 4

A compound having the following structure (tetrazolium compound 4) was synthesized according to the following method.

Tetrazolium compound 4

[Chemical Formula 17]

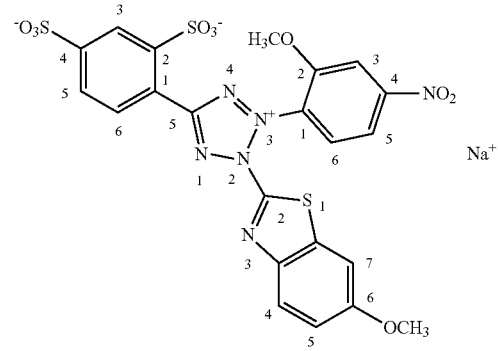

1. Synthesis of Hydrazone Compound 1

Hydrazone compound 1 was synthesized in the same manner as in 1. Synthesis of hydrazone compound 1 of Example 1.

2. Synthesis of Formazan Compound 4

0.76 g of the hydrazone compound 1 was dissolved in a mixed liquid of 10 mL of RO water and 10 mL of DMF, and thereby a hydrazone compound 1 solution was produced. 0.219 g of 2-methoxy-4-nitroaniline (manufactured by Tokyo Chemical Industry Co., Ltd.) was dissolved in 1.5 mL of RO water and 5 mL of acetonitrile. While this solution was maintained at 0° C., 280 µL of 9.6 N HCl was added to the solution, a sodium nitrite solution was added dropwise thereto, and diazotization was performed. This diazotized solution was maintained at −20° C., and this solution was added dropwise to the hydrazone compound 1 solution. After completion of the dropwise addition, 300 µL of 10 N NaOH was added dropwise thereto, the mixture was stirred at room temperature (25° C.) for 2 hours, and thereby a solution including formazan compound 4 (formazan compound 4 solution) was produced. The pH of this formazan compound 4 solution was adjusted to neutrality with 9.6 N HCl, and the solvent was removed. The residue thus obtained was washed with diethyl ether, and then a precipitate was separated by filtration. The precipitate thus obtained was dried, and thereby formazan compound 4 was obtained.

3. Synthesis of Tetrazolium Compound 4

The formazan compound 4 of the above section 2. was suspended in 15 mL of methanol, and 250 µL of 9.6 N HCl and 5 mL of a 15% ethyl nitrite ($CH_3CH_2NO_2$)-ethanol solution were added thereto. The mixture was stirred for 72 hours at room temperature (25° C.) in the dark.

4. Collection of Tetrazolium Compound 4

Diethyl ether was added to 5 mL of the reaction solution of the above section 3., and thereby tetrazolium compound 4 was precipitated. The precipitate was centrifuged, the supernatant was removed, and then the residue was further washed with diethyl ether. This precipitate was dried, and thus tetrazolium compound 4 was obtained.

Example 5: Synthesis of Tetrazolium Compound 5

A compound having the following structure (tetrazolium compound 5) was synthesized according to the following method.

Tetrazolium compound 5

[Chemical Formula 18]

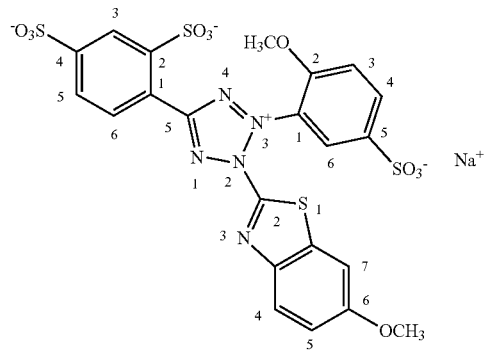

1. Synthesis of Hydrazone Compound 5

1.213 g of sodium 2-formyl-5-hydroxybenzene sulfonate (manufactured by Wako Pure Chemical Industries, Ltd.) and 1.056 g of (6-methoxybenzothiazol-2-yl) hydrazine (also known as 2-hydrazino-6-methoxy-1,3-benzothiazole) (manufactured by Santa Cruz Biotechnology, Inc.) were dissolved in 43 mL of DMF. This solution was heated and stirred in a water bath at 60° C. for 2 hours under the acidity of acetic acid. After completion of the heating and stirring, the solvent was removed. The residue thus obtained was washed with diethyl ether, and then a precipitate was separated. This precipitate was dried, and thereby hydrazone compound 5 was obtained.

2. Synthesis of Formazan Compound 5

1.05 g of the hydrazone compound 5 obtained as described above was dissolved in a mixed liquid of 20 mL of RO water and 20 mL of DMF, and thereby a hydrazone compound 5 solution was produced. 0.528 g of o-anisidine-5-sulfonic acid (manufactured by Tokyo Chemical Industry Co., Ltd.) was suspended in 8.18 mL of RO water, and then 260 μL of 10 N NaOH was added thereto to dissolve the compound. While this solution was maintained at 0° C., 560 μL of 9.6 N HCl was added to the solution, a sodium nitrite solution was added dropwise thereto, and diazotization was performed. This diazotized solution was maintained at −20° C., and this solution was added dropwise to the hydrazone compound 5 solution. After completion of the dropwise addition, 600 μL of 10 N NaOH was added dropwise thereto, the mixture was stirred for 2 hours at room temperature (25° C.), and thereby a solution including formazan compound 5 (formazan compound 5 solution) was produced. The pH of this formazan compound 5 solution was adjusted to neutrality with 9.6 N HCl, and then the solvent was removed. The residue thus obtained was washed with ethyl acetate, and then a precipitate was separated. This precipitate was dried, and thus formazan compound 5 was obtained.

3. Synthesis of Tetrazolium Compound 5

The formazan compound 5 obtained in the above section 2. was dissolved in 10 mL of RO water. A disposable column (size: 20 cm×5 cm) was packed with a filler for column chromatography (manufactured by NACALAI TESQUE, INC., COSMOSIL 40C$_{18}$-PREP), and the disposable column was mounted in a column preparative separation system (manufactured by BÜCHI Labortechnik AG, trade name: SEPACORE). The formazan compound 5 solution was purified using the above-mentioned column system. The solvent of a red fraction thus collected was removed, and to a solid component thus obtained, 15 mL of methanol, 250 μL of 9.6 N HCl, and 5 mL of a 15% ethyl nitrite (CH$_3$CH$_2$NO$_2$)-ethanol solution were added. The mixture was stirred for 72 hours at room temperature (25° C.) in the dark.

4. Collection of Tetrazolium Compound 5

Diethyl ether was added to 5 mL of the reaction solution obtained in the above section 3., and thereby tetrazolium compound 5 was precipitated. The precipitate was centrifuged, the supernatant was removed, and then the residue was further washed with diethyl ether. A precipitate thus obtained was dried in a draught, and thus tetrazolium compound 5 was obtained (120 mg, yield: 7.6% by mass).

Example 6: Synthesis of Tetrazolium Compound 6

A compound having the following structure (tetrazolium compound 6) was synthesized according to the following method.

Tetrazolium compound 6

[Chemical Formula 19]

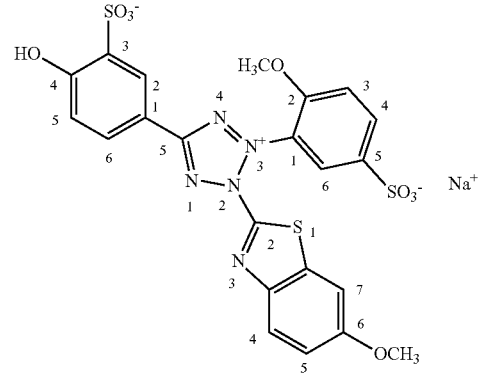

1. Synthesis of Hydrazone Compound 6

1.213 g of sodium 5-formyl-2-hydroxybenzene sulfonate (also known as 4-formyl-1-phenol-2-sulfonic acid sodium salt) (manufactured by T&W GROUP) and 1.056 g of (6-methoxybenzothiazol-2-yl)hydrazine (also known as 2-hydrazino-6-methoxy-1,3-benzothiazole) (manufactured by Santa Cruz Biotechnology, Inc.) were dissolved in 43 mL of DMF. This solution was heated and stirred in a water bath at 60° C. for 2 hours under the acidity of acetic acid. After completion of the heating and stirring, the solvent was removed. The residue thus obtained was washed with diethyl ether, and then a precipitate was separated by centrifuge. The precipitate thus obtained was dried, and thus hydrazone compound 6 was obtained.

2. Synthesis of Formazan Compound 6

1.05 g of the hydrazone compound 6 obtained as described above was dissolved in 20 mL of RO water and 20 mL of DMF, and thereby a hydrazone compound 6 solution was produced. 0.528 g of o-anisidine-5-sulfonic acid (manufactured by Tokyo Chemical Industry Co., Ltd.) was suspended in 8.18 mL of RO water, and 260 μL of 10 N NaOH was added thereto to dissolve the compound. While this solution was maintained at 0° C., 560 μL of 9.6 N HCl was added to the solution, a sodium nitrite solution was added dropwise thereto, and diazotization was performed. While this diazotized solution was maintained at −20° C., this solution was added dropwise to the hydrazone compound 6 solution. After completion of the dropwise addition, 600 μL of 10 N NaOH was added dropwise thereto, the mixture was stirred at room temperature (25° C.) for 2 hours, and thereby a solution including formazan compound 6 (formazan compound 6 solution) was produced. The pH of this formazan compound 6 solution was adjusted to 6.8 with 9.6 N HCl, and the solvent was removed. The residue thus obtained was washed with ethyl acetate, and then a precipitate was separated by centrifugation. The precipitate thus obtained was dried, and thus formazan compound 6 was obtained.

3. Synthesis of Tetrazolium Compound 6

The formazan compound 6 obtained in the above section 2. was added to 15 mL of methanol, 250 μL of 9.6 N HCl, and 5 mL of a 15% ethyl nitrite ($CH_3CH_2NO_2$)-ethanol solution, and the mixture was stirred for 72 hours at room temperature (25° C.) in the dark.

4. Collection of Tetrazolium Compound 6

Diethyl ether was added to the reaction solution obtained in the above section 3., and thereby tetrazolium compound 6 was precipitated. The precipitate was centrifuged, the supernatant was removed, and then the residue was further washed with diethyl ether. A precipitate thus obtained was dried, and thus tetrazolium compound 6 was obtained.

Example 7: Synthesis of Tetrazolium Compound 7

A compound having the following structure (tetrazolium compound 7) was synthesized according to the following method.

Tetrazolium compound 7

[Chemical Formula 20]

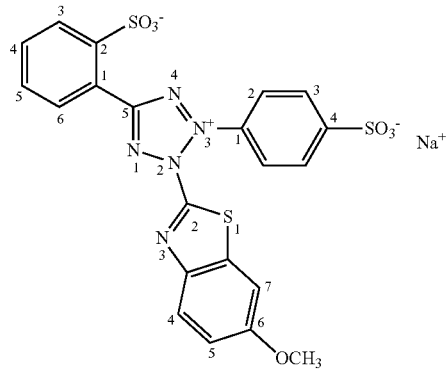

1. Synthesis of Hydrazone Compound 7

25.0 g of 2-sulfobenzaldehyde sodium salt (manufactured by Tokyo Chemical Industry Co., Ltd.) and 22.6 g of p-hydrazinobenzene sulfonic acid 0.5 hydrate (manufactured by Tokyo Chemical Industry Co., Ltd.) were dissolved in 250 mL of RO water, and 11.8 g of sodium acetate was added thereto. The mixture was heated and stirred in a water bath at 60° C. for 2 hours. After completion of the heating and stirring, the solvent was removed. The residue thus obtained was washed with methanol, and then a precipitate was separated by filtration. The precipitate thus obtained was dried, and thus hydrazone compound 7 was obtained.

2. Synthesis of Formazan Compound 7

0.6 g of the hydrazone compound 7 obtained as described above was dissolved in 20 mL of RO water, and thereby a hydrazone compound 7 solution was produced. 0.234 g of 2-amino-6-methoxybenzothiazole (manufactured by Tokyo Chemical Industry Co., Ltd.) was dissolved in 1.5 mL of RO water and 5 mL of acetonitrile. While this solution was maintained at 0° C., 280μ of 9.6 N HCl was added to the solution, a sodium nitrite solution was added dropwise thereto, and diazotization was performed. This diazotized solution was maintained at −20° C., and this solution was added dropwise to the hydrazone compound 7 solution. After completion of the dropwise addition, 300 μL of 10 N NaOH was added dropwise thereto, the mixture was stirred for 2 hours at room temperature (25° C.), and thereby a solution including formazan compound 7 (formazan compound 7 solution) was produced. The pH of this formazan compound 7 solution was adjusted to neutrality with 9.6 N HCl, and the solvent was removed. The residue thus obtained was washed with isopropanol, and then a precipitate was separated by filtration. This precipitate was dried, and thus formazan compound 7 was obtained.

3. Synthesis of Tetrazolium Compound 7

The formazan compound 7 of the above section 2. was added to 15 mL of methanol, 250 μL of 9.6 N HCl, and 5 mL of a 15% ethyl nitrite ($CH_3CH_2NO_2$)-ethanol solution, and the mixture was stirred for 72 hours at room temperature (25° C.) in the dark.

4. Collection of Tetrazolium Compound 7

Diethyl ether was added to 5 mL of the reaction solution of the above section 3., and thereby tetrazolium compound 7 was precipitated. The precipitate was centrifuged, the supernatant was removed, and then the residue was further washed with diethyl ether. A precipitate thus obtained was dried, and thus tetrazolium compound 7 was obtained.

Example 8: Synthesis of Tetrazolium Compound 8

A compound having the following structure (tetrazolium compound 8) was synthesized according to the following method.

Tetrazolium compound 8

[Chemical Formula 21]

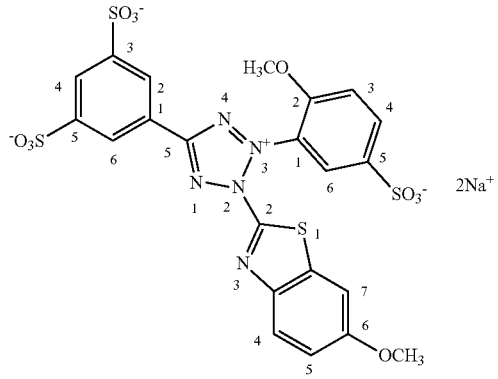

Tetrazolium compound 8 was obtained in the same manner as in Example 1, except that in regard to 1. Synthesis of hydrazone compound 1 of Example 1, disodium 4-formylbenzene-1,3-disulfonate (manufactured by Tokyo Chemical Industry Co., Ltd.) was changed to 5-formylbenzene-1,3-disulfonic acid disodium salt) (manufactured by Tokyo Chemical Industry Co., Ltd.); and in regard to the synthesis of formazan compound 1, the amine was changed from p-anisidine-3-sulfonic acid (manufactured by Tokyo Chemical Industry Co., Ltd.) to o-anisidine-3-sulfonic acid.

Example 9: Synthesis of Tetrazolium Compound 9

A compound having the following structure (tetrazolium compound 9) was synthesized according to the following method.

Tetrazolium compound 9

[Chemical Formula 22]

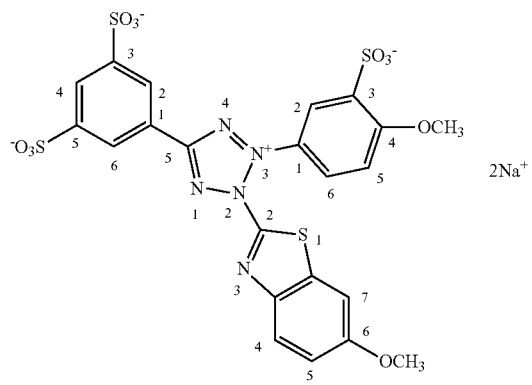

Tetrazolium compound 9 was obtained in the same manner as in Example 1, except that in regard to 1. Synthesis of hydrazone compound 1 of Example 1, disodium 4-formylbenzene-1,3-disulfonate (manufactured by Tokyo Chemical Industry Co., Ltd.) was changed to disodium 5-formylbenzene-1,3-disulfonate.

Example 10: Synthesis of Tetrazolium Compound 10

A compound having the following structure (tetrazolium compound 10) was synthesized according to the following method.

Tetrazolium compound 10

[Chemical Formula 23]

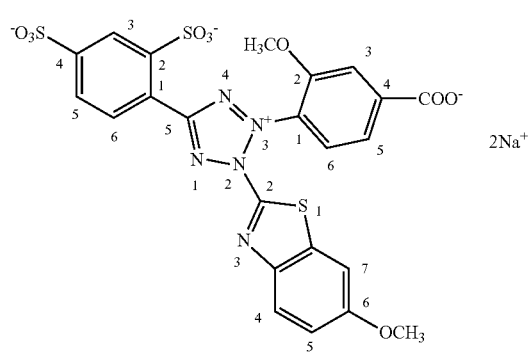

Tetrazolium compound 10 was obtained in the same manner as in Example 1, except that in regard to the synthesis of formazan compound 1 of Example 1, the amine was changed from p-anisidine-3-sulfonic acid (manufactured by Tokyo Chemical Industry Co., Ltd.) to 4-amino-3-methoxybenzoic acid (manufactured by Tokyo Chemical Industry Co., Ltd.).

Example 11: Synthesis of Tetrazolium Compound 11

A compound having the following structure (tetrazolium compound 11) was synthesized according to the following method.

Tetrazolium compound 11

[Chemical Formula 24]

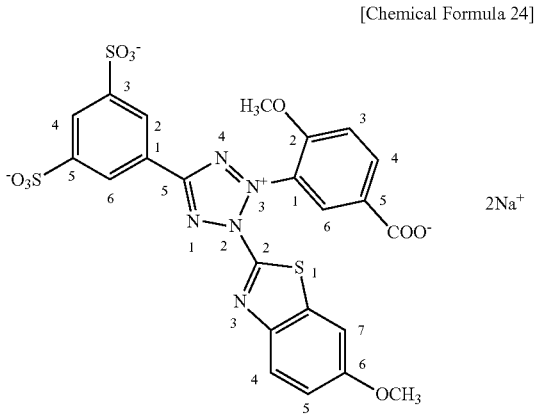

1. Synthesis of Hydrazone Compound 11

4.65 g (0.015 mol) of 5-formylbenzene-1,3-disulfonic acid disodium salt (manufactured by Tokyo Chemical Industry Co., Ltd.) and 2.93 g (0.015 mol) of (6-methoxybenzothiazol-2-yl)hydrazine (also known as 2-hydrazino-6-methoxy-1,3-benzothiazole) (manufactured by Santa Cruz Biotechnology, Inc.) were dissolved in a mixed liquid of 50 mL of DMF and 50 mL of RO water. 860 μL of acetic acid was added to this solution, and the mixture was heated with stirring in a water bath (60° C.) for 2 hours. After completion of the heating and stirring, the solvent was removed, and a residue was obtained. This residue was washed with diethyl ether, and then a precipitate was separated by filtration. This precipitate was dried, and thereby hydrazone compound 11 was obtained.

2. Synthesis of Formazan Compound 11

1.4 g of the hydrazone compound 11 of the above section 1. was dissolved in a mixed liquid of 10 mL of RO water and 5 mL of DMF, and thus a hydrazone compound 11 solution was produced. 0.334 g of 3-amino-4-methoxybenzoic acid (manufactured by Tokyo Chemical Industry Co., Ltd.) was dissolved in a mixed liquid of 1 mL of RO water and 5 mL of DMF. This solution was maintained at 0° C., and 400 μL of 9.6 N HCl was added thereto. Subsequently, a sodium nitrite solution (0.152 g was dissolved in 1 mL) was further added to the mixture, and diazotization was performed. This diazotized solution was maintained at −20° C., and this solution was added to the hydrazone compound 11 solution. Next, 600 μL of 10 N NaOH was added thereto, the mixture was stirred for 2 hours at room temperature, and thereby a solution including the formazan compound 11 (formazan compound 11 solution) was produced. The pH of this formazan compound 11 solution was adjusted to neutrality with 9.6 N HCl, and the solution was concentrated. 10 mL of RO water was added to the concentrated formazan compound 11 to dissolve the compound, and thus a formazan compound 11 solution was produced.

3. Purification of Formazan Compound 11 and Synthesis of Tetrazolium Compound 11

A disposable column (size: 20 cm×5 cm) was packed with a filler for column chromatography (manufactured by NACALAI TESQUE, INC., COSMOSIL 40$C_{18}$-PREP), and the disposable column was mounted in a column preparative separation system (manufactured by BÜCHI Labortechnik AG, trade name: SEPACORE). The formazan compound 11 solution was purified using this column system. The solvent of a red fraction thus collected was removed, and to a solid component thus obtained, 100 mL of methanol, 400 µL of 9.6 N HCl, and 5 mL of a 15% ethyl nitrite ($CH_3CH_2NO_2$)-ethanol solution were added. The mixture was stirred for 48 hours at room temperature in the dark.

4. Collection of Tetrazolium Compound 11

The above-described solution was dried with an evaporator. Next, 10 mL of RO water was added to the residue, the mixture was neutralized with 1 M $Na_2CO_3$, and the mixture was dissolved. This was purified by a SEPACORE preparative separation system, and an orange-colored fraction was collected. The solvent was removed from this fraction with an evaporator, and a solid content was obtained. 5 mL of methanol was added to this solid content to dissolve the solid, and then 50 mL of diethyl ether was added thereto, and there by a precipitate was obtained. This precipitate was dried, and thus tetrazolium compound 11 was obtained.

Example 12: Synthesis of Tetrazolium Compound 12

A compound having the following structure (tetrazolium compound 12) was synthesized according to the following method.

Tetrazolium compound 12

[Chemical Formula 25]

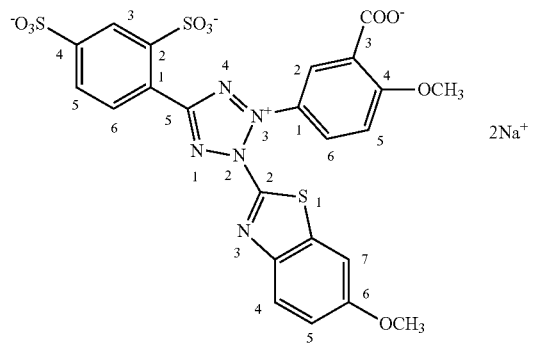

1. Synthesis of Hydrazone Compound 1

Hydrazone compound 1 was synthesized in the same manner as in 1. Synthesis of hydrazone compound 1 of Example 1.

2. Synthesis of Formazan Compound 12

1.4 g of hydrazone compound 1 was added to a mixed solution of 10 mL of RO water and 5 mL of DMF, and thereby a hydrazone compound 1 solution was produced. 0.334 g of 5-amino-2-methoxybenzoic acid (manufactured by Tokyo Chemical Industry Co., Ltd.) was added to 1 mL of RO water and 5 mL of DMF to dissolve the compound. This solution was maintained at 0° C., and 400 µL of 9.6 N HCl was added thereto. Subsequently, a sodium nitrite solution (0.152 g dissolved in 1 mL; Wako Pure Chemical Industries, Ltd.) was further added thereto, and diazotization was performed. This diazotized solution was maintained at −20° C., and this solution was added to a hydrazone compound 1 solution. Subsequently, 600 µL of 10 N NaOH was added thereto, subsequently the mixture was stirred at room temperature for 2 hours, and thereby, a solution including formazan compound 12 (formazan compound 12 solution) was produced. The pH of the formazan compound 12 solution was adjusted to neutrality with 9.6 N HCl, the solvent was removed, and thereby formazan compound 12 was obtained.

3. Purification of Formazan Compound 12 and Synthesis of Tetrazolium Compound 12

The formazan compound 12 of the above section 2. was dissolved in 10 mL of RO water, and thereby a formazan compound 12 solution was produced. A disposable column (size: 20 cm×5 cm) was packed with a filler for column chromatography (manufactured by NACALAI TESQUE, INC., COSMOSIL 40$C_{18}$-PREP), and the disposable column was mounted in a column preparative separation system (manufactured by BÜCHI Labortechnik AG, trade name: SEPACORE). The formazan compound 12 solution was purified using this column system. The solvent of a red fraction thus collected was removed, and to a solid component thus obtained, 100 mL of methanol, 400 µL of 9.6 N HCl, and 15 mL of a 15% ethyl nitrite ($CH_3CH_2NO_2$)-ethanol solution were added. The mixture was stirred for 48 hours at room temperature in the dark.

4. Collection of Tetrazolium Compound 12 and Repurification with Column

The solution of the above section 3. was dried, and then 10 mL of RO water was added thereto. The solution was neutralized with 1 M $Na_2CO_3$ to dissolve the compound. This was purified with a column preparative separation system (manufactured by BÜCHI Labortechnik AG, trade name: SEPACORE), and an orange-colored fraction was collected. The solvent of this fraction was removed with an evaporator, and a solid content was obtained. 5 mL of methanol was added to this solid content to dissolve the solid, and then 50 mL of diethyl ether was added thereto. Thereby, a precipitate was obtained. This precipitate was dried, and thus tetrazolium compound 12 was obtained (300 mg, yield: 17%).

Example 13: Synthesis of Tetrazolium Compound 13

A compound having the following structure (tetrazolium compound 13) was synthesized according to the following method.

Tetrazolium compound 13

[Chemical Formulla 26]

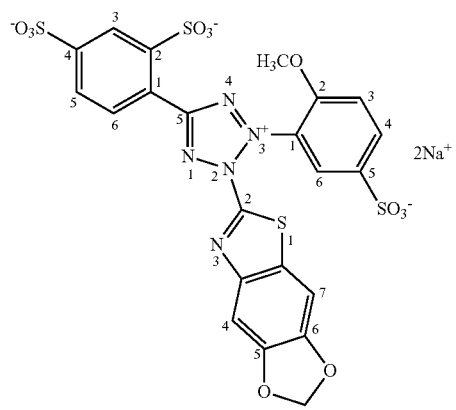

1. Synthesis of Hydrazone Compound 13

1.38 g of disodium 4-formylbenzene-1,3-disulfonate (manufactured by Tokyo Chemical Industry Co., Ltd.) and 0.9831 g of 6-hydrazino[1,3]dioxolo[4,5-f][1,3]benzothiazole (manufactured by Matrix Scientific) were suspended in 10 mL of DMF and 10 mL of RO water. This suspension was stirred in a water bath (60° C.) for 90 minutes under the acidity of acetic acid. After completion of the heating and stirring, the suspension was concentrated (0 Torr, 60° C.). This residue was washed two times with diethyl ether, and then a precipitate was preoperatively separated. This precipitate was dried, and thereby hydrazone compound 13 was obtained.

2. Synthesis of Formazan Compound 13

0.1 g of the hydrazone compound 13 was dissolved in a mixed liquid of 1 mL of RO water and 1 mL of DMF, and thereby a hydrazone compound 13 solution was produced. This hydrazone compound 13 solution was maintained at 0° C., and 0.04 g of o-anisidine-5-sulfonic acid (manufactured by Tokyo Chemical Industry Co., Ltd.) was suspended in 1 mL of RO water. 20 µL of 10 N NaOH was added thereto, and the compound was dissolved. This solution was maintained at 0° C., 40 µL of 10 N HCl was added to the solution, and then a sodium nitrite solution was further added thereto. Thereby, diazotization was performed. This diazotized solution was maintained at −20° C., and this solution was added dropwise to the hydrazone compound 13 solution. Subsequently, 40 µL of 10 N NaOH was added thereto, the mixture was stirred at 4° C., and thereby, a solution including formazan compound 13 (formazan compound 13 solution) was produced. The pH of this formazan compound 13 solution was adjusted to neutrality with 9.6 N HCl, and the solvent was removed. The residue thus obtained was washed with isopropanol, and then a precipitate was separated by filtration. The precipitate thus obtained was dried, and thereby formazan compound 13 was obtained.

The formazan compound thus obtained was purified in the same manner as in Example 1, and a tetrazolium compound was synthesized and collected in the same manner. Thus, tetrazolium compound 13 was synthesized.

Examples 14 to 16: Synthesis of Tetrazolium Compounds 14 to 16

Compounds having the following structures (tetrazolium compounds 14 to 16) were synthesized according to the following method.

Tetrazolium compound 14

[Chemical Formula 27]

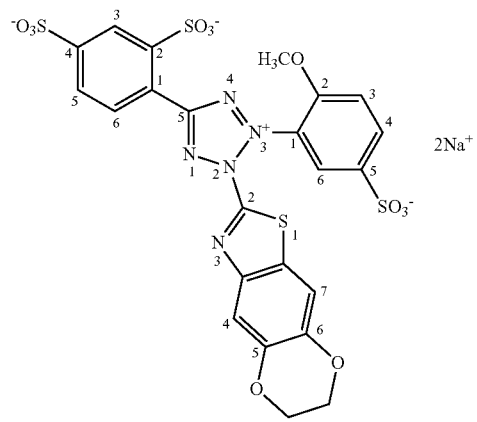

Tetrazolium compound 15

[Chemical Formula 28]

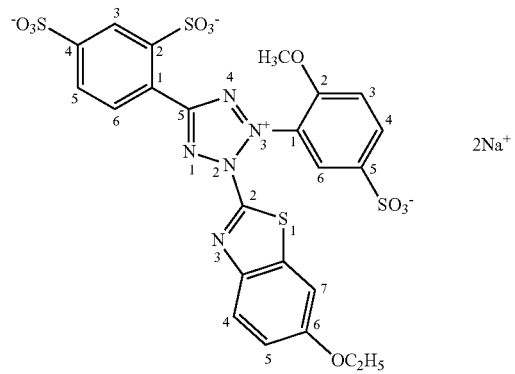

Tetrazolium compound 16

[Chemical Formula 29]

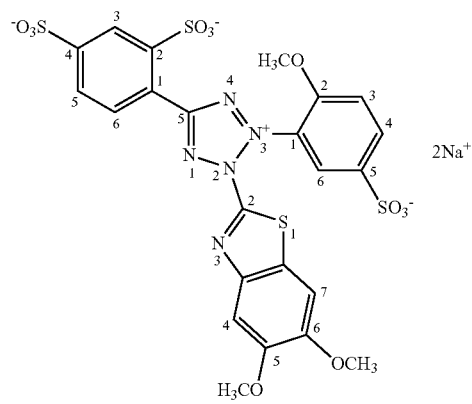

1. Synthesis of Hydrazone Compounds 14 to 16

Hydrazone compounds 14 to 16 were synthesized in the same manner as in Example 13, except that various reagents and various solvents were added as described below.

TABLE 1

|  | Hydrazine※1 | Amount of addition (g) | Aldehyde※2 | Amount of addition (g) | Acetic acid (μL) | DMF (mL) | RO water (mL) |
|---|---|---|---|---|---|---|---|
| Example 13 | 6-Hydrazino[1,3]dioxolo[4,5-f][1,3]benzothiazole | 0.9831 | Disodium 4-Formylbenzene-1,3-disulfonate | 1.38 | 256 | 10 mL | 10 mL |
| Example 14 | 2-Hydrazino-6,7-dihydro[1,4]dioxino[2,3-f][1,3]benzothiazole | 0.9666 |  | 1.27 | 236 |  |  |
| Example 15 | 2-Hydrazino-6-methoxy-1,3-benzothiazole | 0.984 |  | 1.38 | 256 |  |  |
| Example 16 | 2-Hydrazino-5,6-dimethoxy-1,3-benzothiazole | 0.9767 |  | 1.27 | 236 |  |  |

※1All manufactured by Matrix Scientific
※2All manufactured by Tokyo Chemical Industry Co., Ltd.

2. Synthesis of Formazan Compounds 14 to 16

Synthesis of formazan compounds 14 to 16 was performed in the same manner as in Example 13, except that various reagents and various solvents were added as described below.

TABLE 2

|  |  | Amount of addition (mg) | Amine※3 | Amount of addition (mg) |
|---|---|---|---|---|
| Example 13 | Hydrazone compound 13 | 100 | o-anisidin-5-sulfonic acid | 40 |
| Example 14 | Hydrazone compound 14 | 103 |  |  |
| Example 15 | Hydrazone compound 15 | 100 |  |  |
| Example 16 | Hydrazone compound 16 | 104 |  |  |

The formazan compounds thus obtained were purified in the same manner as in Example 1, and tetrazolium compounds synthesized and collected in the same manner. Thus, tetrazolium compounds 14 to 16 were synthesized.

Example 17: Synthesis of Tetrazolium Compound 17

A compound having the following structure (tetrazolium compound 17) was synthesized according to the following method.

Tetrazolium compound 17

[Chemical Formula 30]

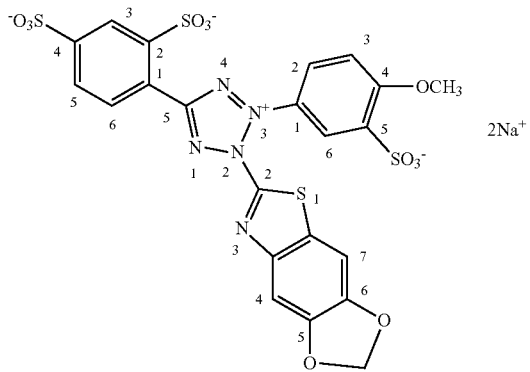

1. Synthesis of Hydrazone Compound 17

1.38 g (4.46 mmol) of disodium 4-formylbenzene-1,3-disulfonate (manufactured by Tokyo Chemical Industry Co., Ltd.) and 0.98 g (4.46 mmol) of 6-hydrazino[1,3]dioxolo[4,5-f][1,3]benzothiazole (manufactured by Matrix Scientific) were dissolved in a mixed liquid of 10 mL of DMF and 10 mL of RO water. 256 μL of acetic acid was added to this solution, and the mixture was stirred in a water bath (60° C.) for 2 hours. After completion of the heating and stirring, the solvent was removed, and a residue was obtained. This residue was stirred for one hour in diethyl ether, the residue was washed, and then a precipitate was separated by filtration. This precipitate was dried, and thus hydrazone compound 17 was obtained.

2. Synthesis of Formazan Compound 17

1.81 g of hydrazone compound 17 of the above section 1. was dissolved in a mixed liquid of 15 mL of RO water and 15 mL of DMF, and thereby, a hydrazone compound 17 solution was produced. 0.528 g of p-anisidine-3-sulfonic acid (manufactured by Tokyo Chemical Industry Co., Ltd.) was suspended in 8.18 mL of RO water, 260 μL of 10 N NaOH was further added thereto to dissolve the compound. This solution was maintained at 0° C., and 560 μL of 9.6 N HCl was added to the solution. A sodium nitrite solution (0.194 g was dissolved in 1 mL; Wako Pure Chemical Industries, Ltd.) was added thereto, and diazotization was performed. This diazotized solution as maintained at −20° C., and this solution was added dropwise to the hydrazone compound 17 solution. After completion of the dropwise addition, 600 μL of 10 N NaOH was added thereto, and the mixture was stirred at −20° C. Subsequently, the solvent of this solution was removed, the residue was dried, and thereby, formazan compound 17 was obtained.

3. Purification of Formazan Compound 17 and Synthesis of Tetrazolium Compound 17

15 mL of RO water was added to the formazan compound 17 of the above section 2., and thereby, a formazan compound 17 solution was produced. A disposable column (size: 20 cm×5 cm) was packed with a filler for column chromatography (manufactured by NACALAI TESQUE, INC., COSMOSIL 40C$_{18}$-PREP), and the disposable column was mounted in a column preparative separation system (manufactured by BÜCHI Labortechnik AG, trade name: SEPA-CORE). The formazan compound 17 solution was purified using this column system, and a red fraction was collected. The solvent of this fraction was removed, and to the solid content thus obtained, 15 mL of methanol, 250 μL of 9.6 N HCl, and 5 mL of a 15% ethyl nitrite (CH$_3$CH$_2$NO$_2$)-ethanol solution were added. The mixture was stirred for 72 hours at room temperature in the dark.

4. Purification and Collection of Tetrazolium Compound 17

The solution obtained in the above section 3. was dried to solid under reduced pressure, and a residue was obtained. 15 mL of RO water was added to this residue, and the residue was dissolved. This solution was mounted in a column preparative separation system (manufactured by BÜCHI Labortechnik AG, trade name: SEPACORE), and an orange-colored fraction including tetrazolium compound 17 was collected. This fraction was dried to solid under reduced pressure, and a purification product including the tetrazolium compound 17 was obtained. 5 mL of methanol was added to this purification product, and the purification product was dissolved therein. Subsequently, diethyl ether was added thereto under stirring, and thereby tetrazolium compound 17 was precipitated. This liquid was centrifuged, and the supernatant was removed. The remaining precipitate (tetrazolium compound 17) was dried, and thus tetrazolium compound 17 was obtained (620 mg, yield: 26% by mass, results of purity analysis by UPLC: 96.1%).

Example 18: Synthesis of Tetrazolium Compound 18

A compound having the following structure (tetrazolium compound 18) was synthesized according to the following method.

Tetrazolium compound 18

[Chemical Formula 31]

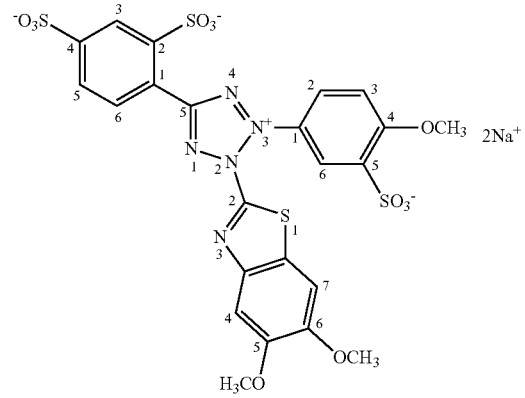

1. Synthesis of Hydrazone Compound 18

1.27 g (4.11 mmol) of disodium 4-formylbenzene-1,3-disulfonate (manufactured by Tokyo Chemical Industry Co., Ltd.) and 0.966 g (4.11 mmol) of 2-hydrazino-5,6-dimethoxy-1,3-benzothiazole (manufactured by Matrix Scientific) were added to a mixed liquid of 10 mL of DMF and 10 mL of RO water to dissolve the compounds. 236 μL of acetic acid was added to this solution, and the mixture was stirred in a water bath (60° C.) for 2 hours. After completion of the heating and stirring, the mixture was dried to solid under reduced pressure, and a residue was obtained. This residue was washed with diethyl ether under stirring, and then a precipitate was preoperatively separated. This precipitate was dried, and thus hydrazone compound 18 was obtained.

2. Synthesis of Formazan Compound 18

1.81 g of formazan compound 18 was added to a mixed liquid of 15 mL of RO water and 15 mL of DMF, and the compound was dissolved therein. 0.528 g of p-anisidine-3-sulfonic acid (manufactured by Tokyo Chemical Industry Co., Ltd.) was suspended in 8.18 mL of RO water, and then 260 μL of 10 N NaOH was added to this suspension to dissolve the compound. This solution was maintained at 0° C., and 560 μL of 9.6 N HCl was added thereto. A sodium nitrite solution (0.194 g was dissolved in 1 mL; Wako Pure Chemical Industries, Ltd.) was added dropwise to the mixture, and diazotization was performed. This diazotized solution was maintained at −20° C., and this solution was added dropwise to the hydrazone solution. After completion of the dropwise addition, 600 μL of 10 N NaOH was added dropwise thereto, and the mixture was stirred for one hour at −20° C. Thus, a formazan compound 18 solution was obtained. This formazan compound 18 solution was dried to solid under reduced pressure, and thereby a residue was obtained. This residue was washed with isopropanol, and then a precipitate was separated by filtration. This precipitate was dried, and thus formazan compound 18 was obtained.

3. Purification of Formazan Compound 18 and Synthesis of Tetrazolium Compound 18

Formazan compound 18 of the above section 2. was added to 15 mL of RO water to dissolve the compound, and a formazan compound 18 solution was produced. A disposable column (size: 20 cm×5 cm) was packed with COSMOSIL 40C$_{18}$-PREP (NACALAI TESQUE, INC.), and the disposable column was mounted in a column preparative separation system (manufactured by BÜCHI Labortechnik AG, trade name: SEPACORE). A fraction including the formazan compound 18 solution was collected using this column system. The solvent of this fraction was removed, and to the solid content thus obtained, 100 mL of methanol, 20 mL of a 15% ethyl nitrite-ethanol solution (manufactured by Tokyo Chemical Industry Co., Ltd.), and 0.5 mL of 9.6 N HCl were added. The mixture was stirred for 48 hours at room temperature in the dark, and thus a solution including the tetrazolium compound 18 was obtained.

4. Collection of Tetrazolium Compound 18

The solution obtained in the above section 3. was dried to solid under reduced pressure, and a crude purification product of the tetrazolium compound 18 was obtained. 15 mL of RO water was added to this crude purification product, and the purification product was dissolved therein. This solution was mounted in a column preparative separation system (manufactured by BÜCHI Labortechnik AG, trade name: SEPACORE). The tetrazolium compound 18 was purified using this column system. A fraction solution thus collected was dried to solid under reduced pressure, and thus a residue was obtained. This residue was suspended in 10 mL of methanol. Furthermore, 100 mL of diethyl ether was added to the suspension under stirring, and thereby the tetrazolium compound 18 was precipitated. This liquid was centrifuged, the supernatant was removed, and thereby a precipitate was washed. The remaining precipitate (tetrazolium compound 18) was dried (yield amount: 1.2 g, yield: 51%, purity analysis by UPLC: 99.2%).

Example 19: Synthesis of Tetrazolium Compound 19

A compound having the following structure (tetrazolium compound 19) was synthesized according to the following method.

Tetrazolium compound 19

[Chemical Formula 32]

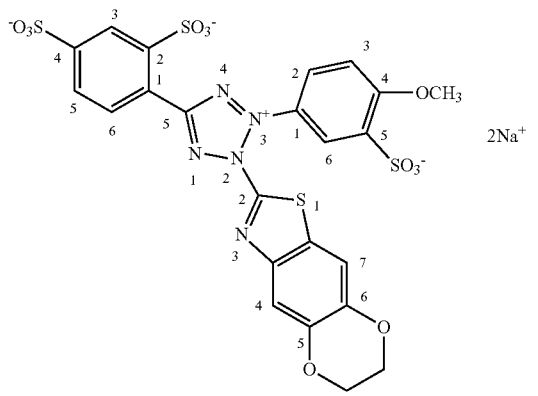

1. Synthesis of Hydrazone Compound 19

1.27 (4.11 mmol) of disodium 4-formylbenzene-1,3-disulfonate (manufactured by Tokyo Chemical Industry Co., Ltd.) and 0.976 g (4.11 mmol) of 2-hydrazino-6,7-dihydro[1,4]dioxino[2,3-f][1,3]benzothiazole (manufactured by Matrix Scientific) were dissolved in a mixed liquid of 10 mL of DMF and 10 mL of RO water. 236 µL of acetic acid was added to this solution, and the mixture was heated and stirred in a water bath (60° C.) for 2 hours. After completion of the heating and stirring, the mixture was dried to solid under reduced pressure, and a residue was obtained. Diethyl ether was added to this residue, and the mixture was stirred and washed for one hour. Subsequently, a precipitate was preparatively separated by centrifugation. Subsequently, the precipitate was dried overnight under reduced pressure, and thus hydrazone compound 19 was obtained.

2. Synthesis of Formazan Compound 19

1.81 g of hydrazone compound 19 was dissolved in a mixed liquid of 10 mL of RO water and 10 mL of DMF, and thereby a hydrazone compound 19 solution was produced. 0.528 g of p-anisidine-3-sulfonic acid (manufactured by Tokyo Chemical Industry Co., Ltd.) was suspended in 8.18 mL of RO water. 260 µL of 10 N NaOH was added to this suspension, and the compound was dissolved therein. This solution was maintained at 0° C., and 560 µL of 9.6 N HCl was added thereto. A sodium nitrite solution (0.194 g was dissolved in 1 mL) was added dropwise to the mixture, and diazotization was performed. This diazotized solution was maintained at −20° C., and this solution was added dropwise to the hydrazone compound 19 solution. After completion of the dropwise addition, 600 µL of 10 N NaOH was added thereto, and the mixture was stirred for one hour at −20° C. Thus, a solution including formazan compound 19 was obtained. This solution was dried to solid under reduced pressure, and a residue was obtained. This residue was washed with isopropanol, and then a precipitate was separated by filtration. This precipitate was dried, and thus formazan compound 19 was obtained.

3. Purification of Formazan Compound 19 and Synthesis of Tetrazolium Compound 19

15 mL of RO water was added to the formazan compound 19 of the above section 2., and the compound was dissolved therein. Thus, a formazan compound 19 solution was produced. A disposable column (size: 20 cm×5 cm) was packed with COSMOSIL $40C_{18}$-PREP (NACALAI TESQUE, INC.), and the disposable column was mounted in a column preparative separation system (manufactured by BÜCHI Labortechnik AG, trade name: SEPACORE). The formazan compound 19 solution was purified using this column system. The solvent of a red fraction thus collected was dried to solid under reduced pressure, and thereby, a residue was obtained. To this residue, 100 mL of methanol, 20 mL of a 15% ethyl nitrite-ethanol solution (manufactured by Tokyo Chemical Industry Co., Ltd.), and 0.5 mL of 9.6 N HCl were added, and the mixture was stirred for 48 hours at room temperature in the dark.

4, Collection of Tetrazolium Compound 19

The solution obtained in the above section 3. was dried to solid under reduced pressure, and a residue was obtained. 15 mL of RO water was added to a residue including this tetrazolium compound 19, and the compound was dissolved therein. This solution was purified with a SEPACORE preparative separation system. A fraction thus collected was dried to solid under reduced pressure, and a residue including the tetrazolium compound 19 was obtained. 5 mL of methanol was added to this residue to dissolve the residue. While this solution was stirred, 100 mL of diethyl ether was added thereto, and the tetrazolium compound 19 was precipitated. This was centrifuged, the supernatant was removed, and thereby the precipitate was washed. The remaining precipitate (tetrazolium compound 19) was dried, and thus, tetrazolium compound 19 was obtained (yield amount: 0.93 g, yield: 40% by mass, purity analysis by UPLC: 96.4%).

Example 20: Synthesis of Tetrazolium Compound 20

A compound having the following structure (tetrazolium compound 20) was synthesized according to the following method.

Tetrazolium compound 20

[Chemical Formula 33]

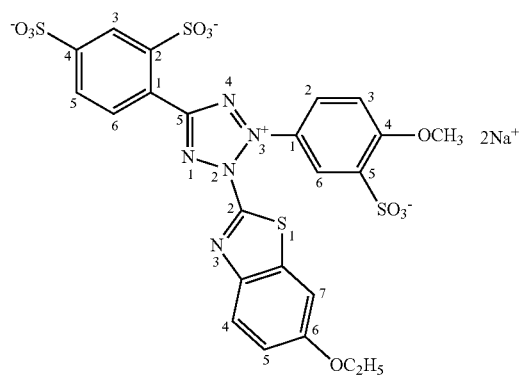

1. Synthesis of Hydrazone Compound 20

1.38 g (4.46 mmol) of disodium 4-formylbenzene-1,3-disulfonate (manufactured by Tokyo Chemical Industry Co., Ltd.) and 0.98 g (4.46 mmol) of (6-ethoxy-benzothiazol-2-yl)hydrazine (manufactured by Matrix Scientific) were dissolved in a mixed liquid of 10 mL of DMF and 10 mL of RO water, and thereby a hydrazone compound 20 was produced. 256 µL of acetic acid was added to this solution, and the mixture was heated and stirred in a water bath (60° C.) for 2 hours. After completion of the heating and stirring, the solvent was removed, and a residue was obtained. 100 mL of diethyl ether was added to this residue, the mixture was stirred for one hour, and then a precipitate was preoperatively separated by centrifugation. The precipitate was left to stand for 2 hours in a draught, and subsequently the precipitate was dried overnight under reduced pressure. Thus, hydrazone compound 20 was obtained.

2. Synthesis of Formazan Compound 20

1.81 g of hydrazone compound 20 was dissolved in a mixed liquid of 15 mL of RO water and 15 mL of DMF, and thereby a hydrazone compound 20 solution was produced. Apart from this, 0.528 g of p-anisidine-3-sulfonic acid (manufactured by Tokyo Chemical Industry Co., Ltd.) was suspended in 8.18 mL of RO water, 260 µL of 10 N NaOH was added to the suspension, and the compound was dissolved therein. This solution was maintained at 0° C., and 560 µL of 9.6 N HCl was added thereto (turbid, dissolved when nitrous acid was added). A sodium nitrite solution (0.194 g was dissolved in 1 mL) was added dropwise thereto, and diazotization was performed. This diazotization solution was maintained at −20° C., and this solution was added dropwise to the hydrazone compound 20 solution. After completion of the dropwise addition, 600 µL of 10 N NaOH was added dropwise thereto, the mixture was stirred for one hour at −20° C., and thereby a formazan compound 20 solution was obtained. The solvent of this formazan compound 20 solution was removed with an evaporator. The residue thus obtained was washed with isopropanol, and then a precipitate was separated by filtration. This precipitate was dried, and thus formazan compound 20 was obtained.

3. Purification of Formazan Compound 20 and Synthesis of Tetrazolium Compound 20

The formazan compound 20 of the above section 2. was dissolved in 15 mL of RO water, and thereby a formazan compound 20 solution was produced. A disposable column (size: 20 cm×5 cm) was packed with a filler for column chromatography (manufactured by NACALAI TESQUE, INC., COSMOSIL 40$C_{18}$-PREP), and the disposable column was mounted in a column preparative separation system (manufactured by BÜCHI Labortechnik AG, trade name: SEPACORE). A fraction including the formazan compound 20 solution was collected using this column system. The solvent of this fraction was removed, and to a solid content thus obtained, 100 mL of methanol, 20 mL of 15% ethyl nitrite-ethanol solution (manufactured by Tokyo Chemical Industry Co., Ltd.), and 0.5 mL of 9.6 N HCl were added. The mixture was stirred for 48 hours at room temperature in the dark.

4. Collection of Tetrazolium Compound 20

The solution of the above section 3. was dried to solid under reduced pressure, and a crude purification product of tetrazolium compound 20 was obtained. 15 mL of RO water was added to this crude purification product, and the purification product was dissolved therein. This solution was purified with a SEPACORE preparative separation system. The solvent of a fraction solution thus collected was removed, and a residue including tetrazolium compound 20 was obtained. This residue was dissolved in 5 mL of methanol. Subsequently, diethyl ether was added thereto with stirring, and thereby tetrazolium compound 20 was precipitated. This was centrifuged, a precipitate was washed, and then the precipitate was preoperatively separated. This precipitate was dried, and thus tetrazolium compound 20 was obtained (amount of yield: 1.4 g, yield: 60%, result of purity analysis by UPLC: 100.0%).

For the tetrazolium compounds 1 to 20 obtained in Examples 1 to 20 described above, and comparative compounds 1 to 5 (Comparative Examples 1 to 5) having the following structures, the maximum absorption wavelength (λmax), the chelation rate, sensitivity, and water-solubility were evaluated according to the methods described below, and the results are presented in the following Table 3.

Comparative Compound 1

[Chemical Formula 34]

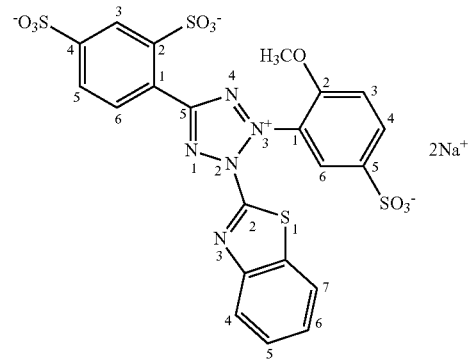

(Comparative Example 1)

-continued

Comparative Compound 2

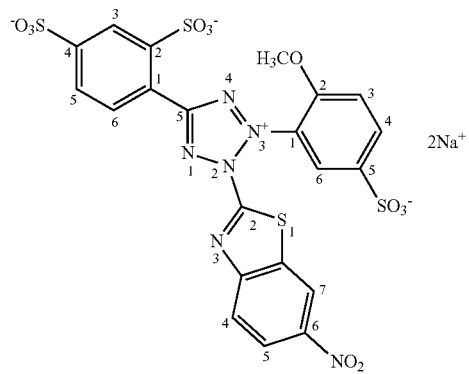

(Comparative Example 2)

Comparative Compound 3

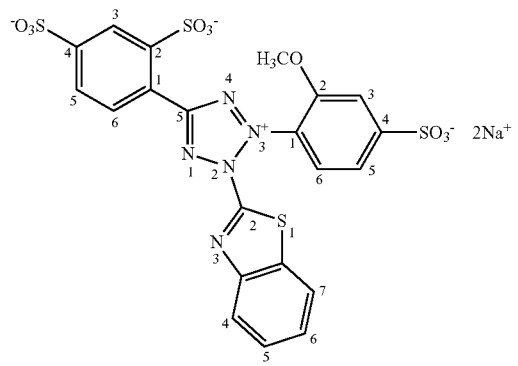

(Comparative Example 3)

Comparative Compound 4

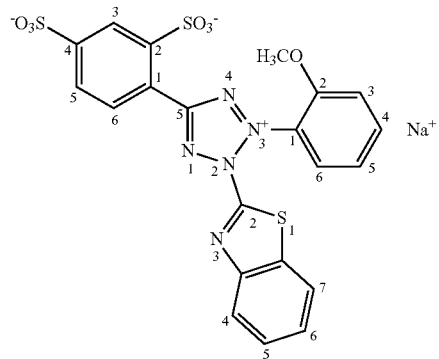

(Comparative Example 4)

Comparative Compound 5

2-benzothiazolyl-3-(4-carboxy-2-methoxyphenyl)-5-[4-(2-sulfoethylcarbamoyl)phenyl]-2H-tetrazolium(WST-4)

(Comparative Example 5)

(Evaluation of Chelation Rate and Maximum Absorption Wavelength (λMax))

10 mM aqueous solution of MOPS was added to each of the formazan compounds so as to obtain a final concentration of 50 to 200 mM, and thereby 100 μL of a sample was produced. At this time, all of the samples were red-brown in color. Apart from this, a 1 M aqueous solution of nickel ion was produced.

10 μL of the aqueous solution of nickel ion thus produced was added to the sample described above, and while the mixture was rapidly stirred, a change in the color tone was observed. The time taken to visually confirm color development after addition of the aqueous nickel solution was measured. In a case in which the time was one minute or less, the chelation rate was rated as "○"; and in a case in which the time was longer than one minute, the chelation rate was rated as "×". In Comparative Examples 2 and 5, since no change in the color tone was observed, it was considered that no chelate was formed. Thus, in Table 3, it was indicated that "No chelation".

For mixed solutions of various compounds in an aqueous solution of formazan and an aqueous solution of nickel, the spectra were measured with a spectrophotometer (measurement cell length: 10 mm) (n=1). Based on each of the spectra, the maximum absorption wavelength (λmax) (nm) of each of the compounds in formazan was determined. The respective results are presented in Table 3. As an example, the spectrum of a chelate compound of formazan compound 1 and nickel ion is shown in FIG. 1. From FIG. 1, it is understood that the maximum absorption wavelength (λmax) of the chelate compound of formazan compound 1 and nickel ion is 630 nm.

Figure 19:
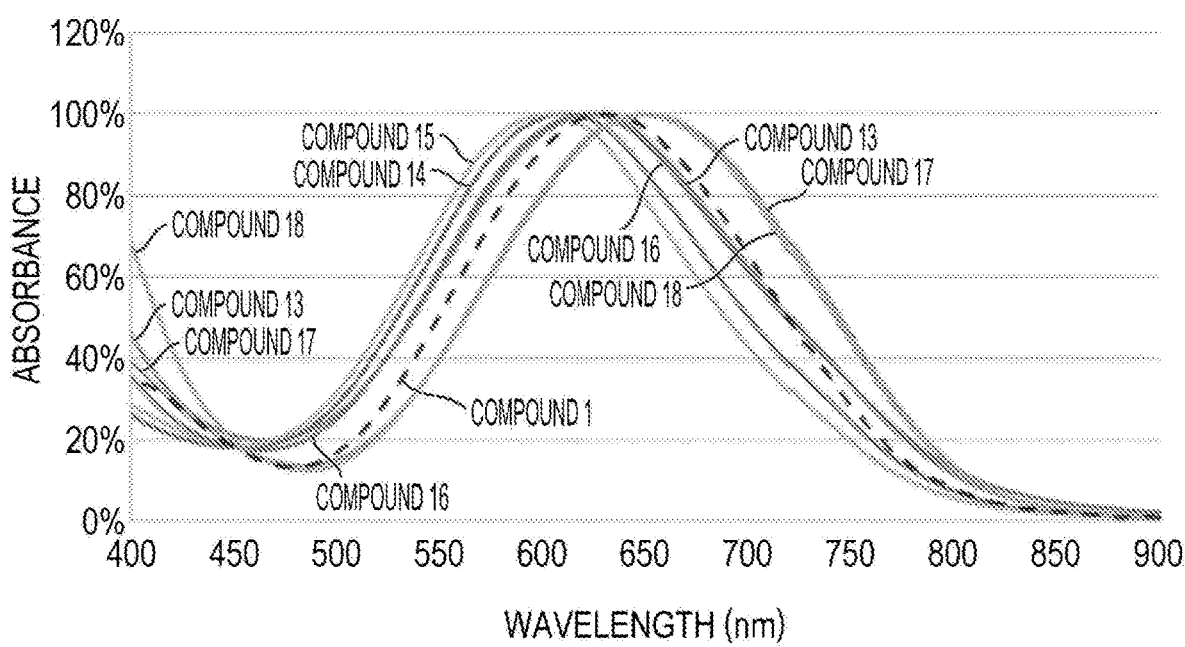
FIG. 19 is a diagram showing the spectra of a Ni²⁺ chelate compound of formazan produced from tetrazolium compounds 1 and 13 to 18. The absorbances of the respective compounds at the maximum absorption wavelength are taken as 100%.

FIG. 19 shows the spectra of $Ni^{2+}$ chelate compounds of formazan produced from tetrazolium compounds 1 and 13 to 18. The absorbance at the maximum absorption wavelength is denoted as 100%. The maximum absorption wavelength of formazan compound 17 or 18 having a 4-methoxy-5-sulfophenyl group and having a q value of 2 was shifted toward the higher wavelength side.

(Evaluation of Sensitivity)

To 0.02 mmol of each compound, 75 μL of RO water and 100 μL of a 0.5 M MOPS solution (pH 7.2) were added to dissolve the compound, and thereby a sample was produced. As a control, 85 μL of RO water and 100 μL of a 0.5 mMOPS solution (pH 7.2) were added to 11.6 mg of 2-benzothiazolyl-3-(4-carboxy-2-methoxyphenyl)-5-[4-(2-sulfoethylcarbamoyl)phenyl]-2H-tetrazolium (WST-4) to dissolve the compound, and thereby a control sample was produced.

Separately, 100 μL of RO water was added to 7 mg of a glucose dehydrogenase that uses flavin adenine dinucleotide (FAD) as a coenzyme (GDH-FAD) (manufactured by TOYOBO CO., LTD., product No.: GLD-351), the enzyme was dissolved, and thus a GDH solution was produced. Furthermore, 200 μL of RO water was added to 3.5 mg of 1-methoxy-5-methylphenazium methyl sulfate (m-PMS) (manufactured by DOJINDO LABORATORIES), and the compound was dissolved therein. Thus, an s-PMS solution was produced. 1 mL of RO water was added to 129 mg of nickel chloride to dissolve the salt, and thus a nickel solution was produced.

To 175 μL of each sample, 10 μL of the GDH solution, 5 μL of the m-PMS solution, and 10 μL of the nickel solution, all of which had been produced as described above, were added, and the mixture was called a reaction solution. Furthermore, to 175 μL of a control sample, 10 μL of the GDH solution and 5 μL of the m-PMS solution, both of which had been produced as described above, and 10 μL of RO water were added, and the mixture was called a control reaction solution.

40 μL of the reaction solution was added to 10 μL each of an aqueous glucose solution at a concentration of 125 mg/dL, an aqueous glucose solution at a concentration of 250 mg/dL, and an aqueous glucose solution at a concentration of 1,000 mg/dL, and the mixtures were allowed to develop color. The spectra were measured with a spectrophotometer (measurement cell length: 50 μm) (n=1). For each of the spectra, the absorbance at the maximum absorption wavelength (λmax) of each of the compounds determined as described above was measured, and the glucose concentration in the colored solution and the absorbance were plotted on the horizontal axis and the vertical axis, respectively. Thus, the gradient (gradient$_{sample}$) was determined.

40 μL of the control reaction solution was added to 10 μL each of an aqueous glucose solution at a concentration of 125 mg/dL, an aqueous glucose solution at a concentration of 250 mg/dL, and an aqueous glucose solution at a concentration of 1,000 mg/dL, and the mixtures were allowed to develop color. The spectra were measured with a spectrophotometer (measurement cell length: 50 μm) (n=1). For each of the spectra, the absorbance at 650 nm, which is the measurement wavelength (λmax) of WST-4, was measured, and the glucose concentration in the colored solution and the absorbance were plotted on the horizontal axis and the vertical axis, respectively. Thus, the gradient (gradient$_{WST-4}$) was determined.

Figure 2:
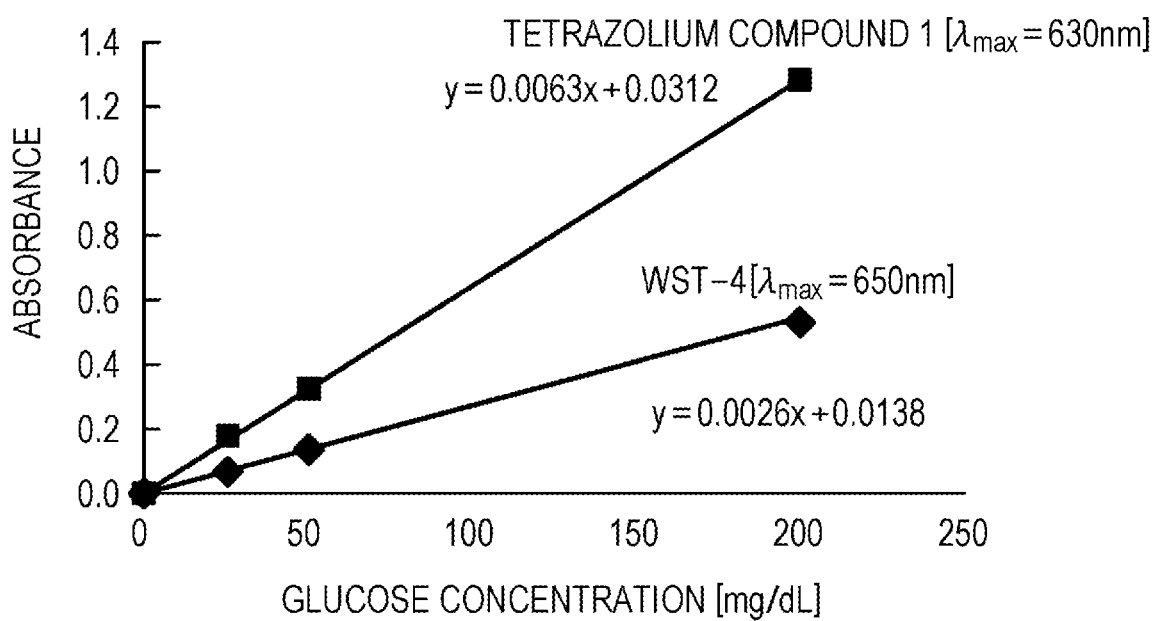
FIG. 2 is a graph showing the relationship between the glucose concentration with regard to tetrazolium compound 1 and WST-4 and the light absorbances of the respective formazans produced (for the tetrazolium compound 1, a Ni²⁺ chelate compound of formazan).

In a case in which the value obtained by dividing the gradient$_{sample}$ determined as described above by the gradient (gradient$_{sample}$/gradient$_{WST-4}$) was 2 or greater, the sensitivity was rated as "⊙"; in a case in which the value of the ratio gradient$_{sample}$/gradient$_{wST-4}$ was 1.5 or greater and less than 2, the sensitivity was rated as "○"; in a case in which the value of the ratio gradient$_{sample}$/gradient$_{wsT-4}$ was greater than 1 and less than 1.5, the sensitivity was rated as "Δ"; and in a case in which the value of the ratio gradient$_{sample}$/gradient$_{WST-4}$ was 1 or less, the sensitivity was rated as "×". As an example, the plot diagrams for the tetrazolium compound 1 and WST-4 are presented in FIG. 2. FIG. 2 is a graph showing the relationship between the glucose concentration and the absorbance of produced formazan in relation to the tetrazolium compound 1 and WST-4. From FIG. 2, it was found that since the gradients of the compound 1 and WST-4 were 0.0063 and 0.0026, respectively, the ratio gradient$_{sample}$/gradient$_{WST-4}$ was about 2.4. Meanwhile, the gradient serves as an index for the color development intensity of each compound. Therefore, when the value obtained by dividing the gradient$_{sample}$ by the gradient$_{WST-4}$ (gradient$_{sample}$/gradient$_{WST-4}$) is greater than one-fold, it is implied that the intensity of color development on the longer wavelength side is higher compared to WST-4, which is a well-known indicator reagent.

(Evaluation of Water-Solubility)

Each compound was added to 100 μL of RO water and 100 μL of a 0.5 M MOPS solution (pH 7.2), in an amount such that the concentration of the compound in the aqueous solution would be 200 mM. After the mixture was stirred for 5 minutes, a precipitate was checked by visual inspection. Separately, each compound was added to 100 μL of RO water and 100 μL of a 0.5 M MOPS solution (pH 7.2), in an amount such that the concentration of the compound in the aqueous solution would be 100 mM. After the mixture was stirred for 5 minutes, a precipitate was checked by visual inspection. Separately, each compound was added to 100 μL of RO water and 100 μL of a 0.5 M MOPS solution (pH 7.2), in an amount such that the concentration of the compound in the aqueous solution would be 20 mM. After the mixture was stirred for 5 minutes, a precipitate was checked by visual inspection. In a case in which there was no precipitate in the 200 mM aqueous solution, the solubility was rated as ⊙. In a case in which a precipitate was seen in the 200 mM aqueous solution, but there was no precipitate in the 100 mM aqueous solution, the solubility was rated as ○. In a case in which a precipitate was seen in the 100 mM aqueous solution, but there was not precipitate in the 20 mM aqueous solution, the solubility was rated as "Δ". In a case in which a precipitate was recognized even in the 20 mM aqueous solution, the solubility was rated as "×".

(Evaluation of Stability)

To 0.02 mmol of each compound, 75 μL of RO water and 100 μL of a 0.5 M MOPS solution (pH 7.2) were added, and the compound was dissolved therein. The solution was used as a sample.

To 175 μL of this sample, 10 μL of the GDH solution, 5 μL of the m-PMS solution, and 10 μL of the nickel solution, all of which had been produced in the same manner as in the above section (Evaluation of sensitivity), were added, and thereby a measurement solution was produced.

As a control, 85 μL of RO water and 100 μL of a 0.5 M MOPS solution (pH 7.2) were added to 11.6 mg of 2-benzothiazolyl-3-(4-carboxy-2-methoxyphenyl)-5-[4-(2-sulfoethylcarbamoyl)phenyl]-2H-tetrazolium (WST-4), and the compound was dissolved. Thus, a control sample was produced. To 175 μL of the control sample, 10 μL of the GDH solution and 5 μL of the m-PMS solution, both of which had been produced as described above, and 10 μL of RO water were added. Thus, a control reaction solution was produced.

Figure 3:
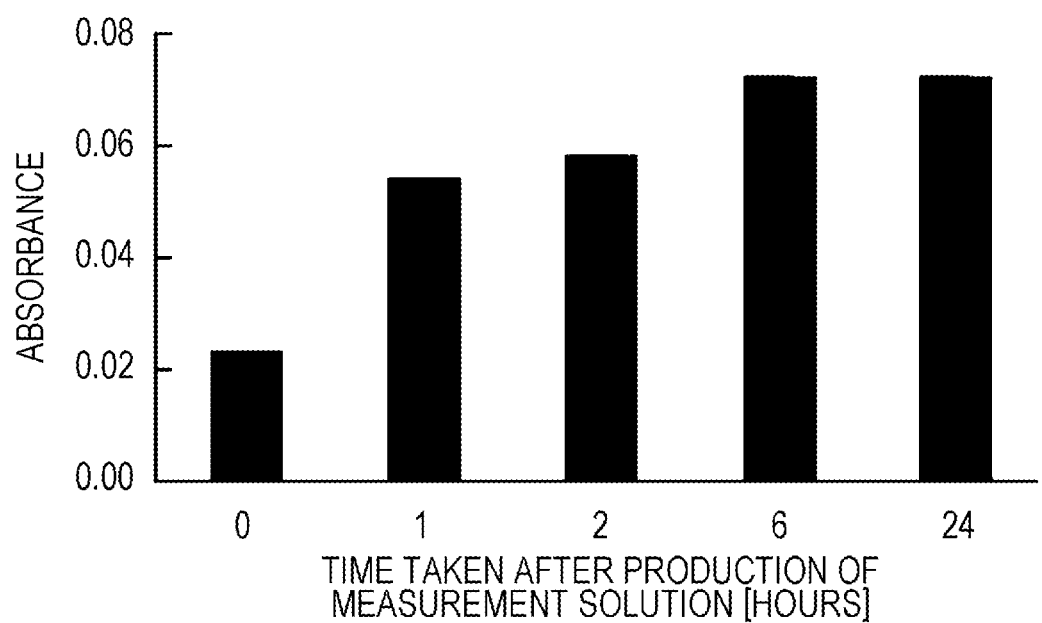
FIG. 3 is a diagram showing the stability evaluation results for the tetrazolium compound 1.

At the time of production of the measurement solution (0 hour), and after 1 hour, 2 hours, and 6 hours from the production, the spectra of the measurement solutions produced as described above were measured using a spectrophotometer (measurement cell length: 50 μm) (n=1). For each spectrum, the absorbance at the maximum absorption wavelength (λmax) of each compound as determined above was measured. The absorbances measured at the time of production of the measurement solution (0 hour) and after 6 hours from the production were designated as $Abs_{0\,h}$ and $Abs_{6\,h}$, respectively. In a case in which the value obtained by subtracting the absorbance at the time of production of the measurement solution (0 hour) from the absorbance after 6 hours and dividing the resultant by the measurement time [($Abs_{6\,h}$−$Abs_{0\,h}$)/6] was 0.01 or less, the stability was rated as "⊙"; in a case in which the above-mentioned value was more than 0.01 and 0.05 or less, the stability was rated as "○"; in a case in which the above-mentioned value was more than 0.05 and 0.1 or less, the stability was rated as "Δ"; and in a case in which the above-mentioned value was more than 0.1, the stability was rated as "×". For example, the stability evaluation results for tetrazolium compound 1 are presented in FIG. 3. In FIG. 3, the absorbances after 1 hour, after 2 hours, and after 24 hours from the production of the measurement solution are also shown. From FIG. 3, it is understood that since the [($Abs_{6\,h}$-$Abs_{0\,h}$)/6] value of the compound 1 was about 0.008, the stability was ⊙. Meanwhile, the [($Abs_{6\,h}$−$Abs_{0\,h}$)/6] value of the control reaction solution was about 0.01.

TABLE 3

| | | Substituted benzothiazolyl group existing at 2-position of tetrazole skeleton | Substituted sulfonated phenyl group existing at 5-position of tetrazole skeleton | | | Substituted sulfonated phenyl group existing at 3-position of tetrazole skeleton | | | | Maximum absorption wavelength (λmax) (nm) | Chelation | rate | Sensitivity Comparison with Comparative Example 5 | Water-solubility | Stability |
|---|---|---|---|---|---|---|---|---|---|---|---|---|---|---|---|
| | | OR³ | R¹ | q | m | Position of sulfuric acid group | R² | n | Position of R² | p | Position of sulfuric acid group | | | | | |
| Example 1 | Compound 1 | 6-Methoxy group | Hydrogen | 1 | 2 | 2,4-position | Methoxy group | 1 | 4-position | 1 | 3-position | 630 | ◯ | ◯ | ⊚ | ⊚ |
| Example 2 | Compound 2 | 6-Methoxy group | Hydrogen | 1 | 2 | 2,4-position | Methoxy group | 1 | 2-position | 1 | 5-position | 600 | ◯ | ⊚ | ⊚ | ⊚ |
| Example 3 | Compound 3 | 6-Methoxy group | Hydrogen | 1 | 2 | 2,4-position | Methoxy group, Nitro group | 2 | 2-position, 4-position | 1 | 5-position | 630 | ◯ | ◯ | ◯ | ◯ |
| Example 4 | Compound 4 | 6-Methoxy group | Hydrogen | 1 | 2 | 2,4-position | Methoxy group, Nitro group | 2 | 2-position, 4-position | 0 | X | 650 | ◯ | ⊚ | △ | ⊚ |
| Example 5 | Compound 5 | 6-Methoxy group | Hydroxyl group | 1 | 1 | 2-position | Methoxy group | 1 | 2-position | 1 | 5-position | 630 | ◯ | ◯ | ◯ | ⊚ |
| Example 6 | Compound 6 | 6-Methoxy group | Hydroxyl group | 1 | 1 | 3-position | Methoxy group | 1 | 2-position | 1 | 5-position | 650 | ◯ | ⊚ | △ | ⊚ |
| Example 7 | Compound 7 | 6-Methoxy group | Hydrogen | 1 | 2 | 2-position | — | 0 | — | 1 | 4-position | 645 | ◯ | ⊚ | ◯ | △ |
| Example 8 | Compound 8 | 6-Methoxy group | Hydrogen | 1 | 2 | 3,5-position | Methoxy group | 1 | 2-position | 1 | 5-position | 620 | ◯ | ◯ | ⊚ | ⊚ |
| Example 9 | Compound 9 | 6-Methoxy group | Hydrogen | 1 | 2 | 3,5-position | Methoxy group | 1 | 4-position | 1 | 3-position | 640 | ◯ | ◯ | ⊚ | ⊚ |
| Example 10 | Compound 10 | 6-Methoxy group | Hydrogen | 1 | 2 | 2,4-position | Methoxy group, Carboxy group | 2 | 2-position, 4-position | 0 | X | 620 | ◯ | ◯ | ⊚ | ⊚ |
| Example 11 | Compound 11 | 6-Methoxy group | Hydrogen | 1 | 2 | 3,5-position | Methoxy group, carboxy group | 2 | 3-position, 5-position | 0 | X | 605 | ◯ | ◯ | ◯ | ⊚ |
| Example 12 | Compound 12 | 6-Methoxy group | Hydrogen | 1 | 2 | 2,4-position | Carboxy group, methoxy group | 2 | 3-position, 4-position | 0 | X | 630 | ◯ | ⊚ 2.4 times | ◯ | ⊚ |
| Example 13 | Compound 13 | 5,6-Methylenedioxy-1,3-benzothiazole | Hydrogen | 2 | 2 | 2,4-position | Methoxy group | 1 | 2-position | 1 | 5-position | 625 | ◯ | ⊚ 2.4 times | ◯ | ⊚ |
| Example 14 | Compound 14 | 6,7-dihydro[1,4]dioxino[2,3-f][1,3]benzothiazole | Hydrogen | 2 | 2 | 2,4-position | Methoxy group | 1 | 2-position | 1 | 5-position | 610 | ◯ | ⊚ 2.4 times | ◯ | ⊚ |
| Example 15 | Compound 15 | 6-Ethoxy group | Hydrogen | 1 | 2 | 2,4-position | Methoxy group | 1 | 2-position | 1 | 5-position | 605 | ◯ | ⊚ 2.4 times | ⊚ | ⊚ |
| Example 16 | Compound 16 | 5,6-Dimethoxy | Hydrogen | 2 | 2 | 2,4-position | Methoxy group | 1 | 2-position | 1 | 5-position | 625 | ◯ | ⊚ 2.4 times | ⊚ | ⊚ |
| Example 17 | Compound 17 | 5,6-Methylenedioxy-1,3-benzothiazole | Hydrogen | 2 | 2 | 2,4-position | Methoxy group | 1 | 4-position | 1 | 5-position | 650 | ◯ | ⊚ 2.4 times | ⊚ | ⊚ |
| Example 18 | Compound 18 | 5,6-Dimethoxy | Hydrogen | 2 | 2 | 2,4-position | Methoxy group | 1 | 4-position | 1 | 5-position | 650 | ◯ | ⊚ 2.4 times | ⊚ | ⊚ |
| Example 19 | Compound 19 | 6,7-dihydro[1,4]dioxino[2,3-f][1,3]benzothiazole | Hydrogen | 2 | 2 | 2,4-position | Methoxy group | 1 | 4-position | 1 | 5-position | 640 | ◯ | ⊚ 2.4 times | ⊚ | ⊚ |
| Example 20 | Compound 20 | 6-Methoxy group | Hydrogen | 1 | 2 | 2,4-position | Methoxy group | 1 | 4-position | 1 | 5-position | 630 | ◯ | ⊚ 2.4 times | ⊚ | ⊚ |
| Comparative Example 1 | Comparative Compound 1 | — | Hydrogen | — | 2 | 2,4-position | Methoxy group | 1 | 2-position | 1 | 5-position | 580 | ◯ | △ | ◯ | ◯ |
| Comparative Example 2 | Comparative Compound 2 | Nitro group | — | — | 2 | 2,4-position | Methoxy group | 1 | 2-position | 1 | 5-position | No chelation | X | — | — | — |
| Comparative Example 3 | Comparative Compound 3 | — | — | — | 2 | 2,4-position | Methyl group | 1 | 2-position | 1 | 4-position | 560 | ◯ | ⊚ | ◯ | ◯ |
| Comparative Example 4 | Comparative Compound 4 | — | — | — | 2 | 2,4-position | Methoxy group | 1 | 2-position | 0 | — | 580 | ◯ | ⊚ | ◯ | ◯ |
| Comparative Example 5 | Comparative Compound 5 | — | 2-Sulfoethyl-carbamoyl group | — | 0 | — | Methoxy group, carboxyl group | 2 | — | 0 | — | No chelation | X | 1 | ◯ | ◯ |

From the results of Table 3 shown above, it can be seen that the blood sugar level can be measured rapidly with satisfactory sensitivity by using the tetrazolium salts of the Examples.

Furthermore, the chelate compounds of the formazans produced from the tetrazolium salts of the Examples and nickel ion exhibit maximum absorption wavelengths (λmax) of 600 nm or higher. Therefore, it is contemplated that even for a whole blood sample, the biological component concentration such as the blood sugar level can be measured accurately with high sensitivity.

As shown in Table 3, the tetrazolium salts of the present disclosure exhibit satisfactory water-solubility. From the results given above, it is speculated that the formazans produced from the tetrazolium salts of the present disclosure, and chelate compounds of those formazans and transition metal ions also exhibit satisfactory water-solubility, similarly to the tetrazolium salts of the present disclosure.

In addition, tetrazolium salts 1 to 3, 5, and 7 to 20, each satisfying any one of the following conditions: (1) m=2 and p=1; (2) m=1 and n=0; or (3) $R^1$ represents a hydroxyl group, and at this time, the sulfo group ($SO^{3-}$) and the hydroxyl group are at the 2,4-position or at the 4- and 6-positions; or (4) p=0 and at least one of $R^2$'s represents a carboxyl group, exhibit more satisfactory water-solubility. Examples 1 to 3 and 8 to 20, in which (1) m=2 and p=1, or (4) p=0 and at least one of $R^2$'s represents a carboxyl group, exhibit particularly satisfactory water-solubility.

Meanwhile, the compound of Comparative Example 2, which is a tetrazolium salt obtained by changing the alkoxy group of the benzothiazolyl group of Example 2 into an electron-withdrawing nitro group, does not form a chelate between formazan and a transition metal ion. Therefore, it is understood that substituting the benzothiazolyl group existing at the 2-position of the tetrazole ring with an alkoxy group is very important for shifting the maximum absorption wavelength toward the longer wavelength side while maintaining the ability of formazan produced from the tetrazolium salt to forma chelate with a transition metal compound.

Evaluation Example 1: Evaluation as Blood Glucose Meter Sensor

1. Production of Coating Liquid

75 μL of RO water and 100 μL of a 0.5 M MOPS solution (pH 7.2) were added to 14.5 mg of tetrazolium compound 1 obtained in Example 1 to dissolve the tetrazolium compound therein, and thus a sample was produced. As a control, 85 μL of RO water and 100 μL of a 0.5 M MOPS solution (pH 7.2) were added to 11.6 mg of 2-benzothiazolyl-3-(4-carboxy-2-methoxyphenyl)-5-[4-(2-sulfoethylcarbamoyl)phenyl]-2H-tetrazolium (WST-4) to dissolve the compound therein, and thus a control sample was produced.

Separately, 100 μL of RO water was added to 7 mg of a glucose dehydrogenase (GDH-FAD) (manufacturedby-TOYOBOCO., LTD., product No.: GLD-351) to dissolve the enzyme, and thus a GDH solution was produced. Furthermore, 200 μL of RO water was added to 3.5 mg of 1-methoxy-5-methylphenazium methyl sulfate (m-PMS) (manufactured by DOJINDO LABORATORIES) to dissolve the compound, and thus an s-PMS solution was produced. 1 mL of RO water was added to 129 mg of nickel chloride to dissolve the salt, and thus a nickel solution was produced.

To the sample, 10 μL of the GDH solution, 5 μL of the s-PMS solution, and 10 μL of the nickel solution, all of which had been produced as described above, were added, and thereby a coating liquid was produced. Furthermore, 10 μL of the GDH solution and 5 μL of the s-PMS solution produced as described above were added to the control sample, and thereby a control coating liquid was produced.

2. Production of Reagent Ribbon

The coating liquid obtained as described above was applied on a PET film, and a reagent ribbon 1 was produced. The area of coating was 1.5 mm×75 mm (total coating amount 5.6 μL). This reagent ribbon 1 was cut in the longitudinal direction, and a reagent piece 2 was obtained (1.5 mm×3 mm).

3. Assembly of Blood Glucose Meter Sensor

Figure 4:
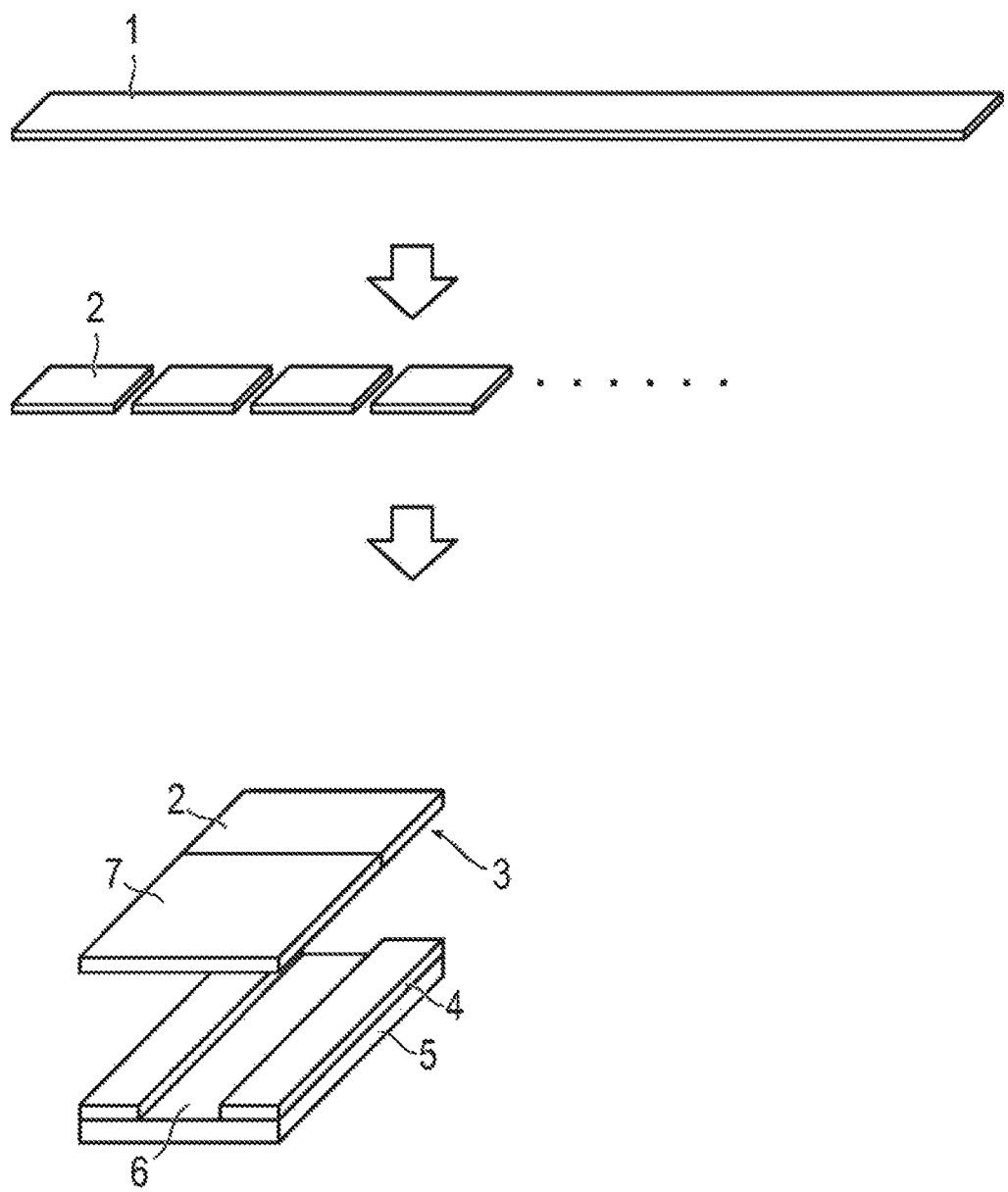
FIG. 4 is a schematic diagram illustrating a blood glucose meter sensor used in Evaluation Example 1.

Along the two edges of a PET film 5 that would become one surface of a blood glucose meter sensor, a double-sided tape having a thickness of 50 μm was provided as a spacer. Next, the reagent-coated surface of the reagent piece 2 was placed to face downward, and the reagent piece 2 was mounted on the double-sided tape 4. Thus, a blood glucose meter sensor was assembled. FIG. 4 is a schematic diagram illustrating the assembly of a blood glucose meter sensor. In FIG. 4, a reagent piece 2 is obtained by cutting the reagent ribbon 1, and then with the reagent-coated surface 3 of the reagent piece 2 being arranged to face downward, the reagent piece 2 is installed on the double-sided tape 4 disposed at the two edges of the PET film 5. Subsequently, a PET film 7 is installed at the remaining adhesive parts of the double-sided tape as shown in the diagram. At this time, a flow channel 6 is formed between the double-sided tapes.

A whole blood sample (Ht40, 100 mg/dL) (hematocrit value 40%, glucose concentration 100 mg/dL) was spotted at the flow channel inlet port of the blood glucose meter sensor thus produced. The whole blood sample (Ht40, 100 mg/dL) was produced as follows: whole blood was collected into a heparin-containing blood sampling tube, the hematocrit value of this whole blood was measured, and the hematocrit value of the whole blood sample was regulated to be Ht40 by adding the blood plasma obtained by separation in advance, or by removing the blood plasma of the whole blood sample, as appropriate. Furthermore, a highly concentrated glucose solution (40 g/dL) was added as appropriate to this whole blood sample, and a whole blood sample (Ht40, 100 mg/dL) was produced. The specimen was spotted on the reagent part, and then after 9 seconds, the spectrum was measured using a fiber spectrophotometer. The absorbance at the maximum absorption wavelength was measured using the spectrum measured with each of the blood glucose meter sensors that used various compounds. The absorbance obtainable in the case of measuring the whole blood sample (Ht40, 100 mg/dL) was designated as $Abs_{BG100}$.

Furthermore, a spectrum was similarly measured using a specimen having a blood sugar level of 0 mg/dL (Ht40, 0 mg/dL) as a control, and the absorbance at the maximum absorption wavelength with each of various compounds (compound 1 and WST-4) was designated as $Abs_{BG0}$. Here, the specimen having a blood sugar level of 0 mg/dL (Ht40, 0 mg/dL) was produced as follows. To 1 mL of the whole blood sample (Ht40, 100 mg/dL), 0.1 mg of a glucose oxidase (GLO-201 manufactured by TOYOBO CO., LTD.) was added. After the addition, the mixture was left to stand at room temperature for 5 minutes, and thus a whole blood sample (Ht40, 0 mg/dL) was produced.

Figure 5:
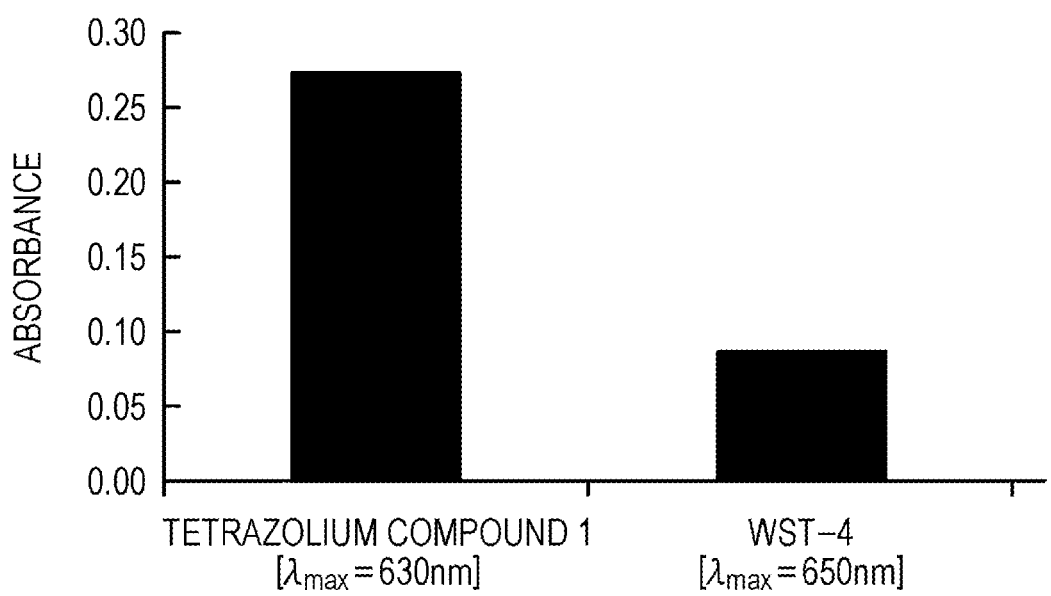
FIG. 5 is a diagram showing the results of the quantity of signal (absorbance) obtainable when a whole blood sample is applied to blood glucose meter sensors to which tetrazolium compound 1 and WST-4 are applied.

The results of determining the values of $\Delta Abs=Abs_{BG100}-Abs_{BG0}$ of various compounds are presented in FIG. 5.

As shown in FIG. 5, in the blood glucose meter sensor to which tetrazolium compound 1 of Example 1 was applied, color development occurred to an extent of about 3 times the color development of WST-4 (650 nm). Therefore, it can be seen that the reagent for biological component concentration measurement including the tetrazolium salt of the present disclosure can detect a biological component with high sensitivity, even in the case of using a whole blood sample.

Figure 6A:
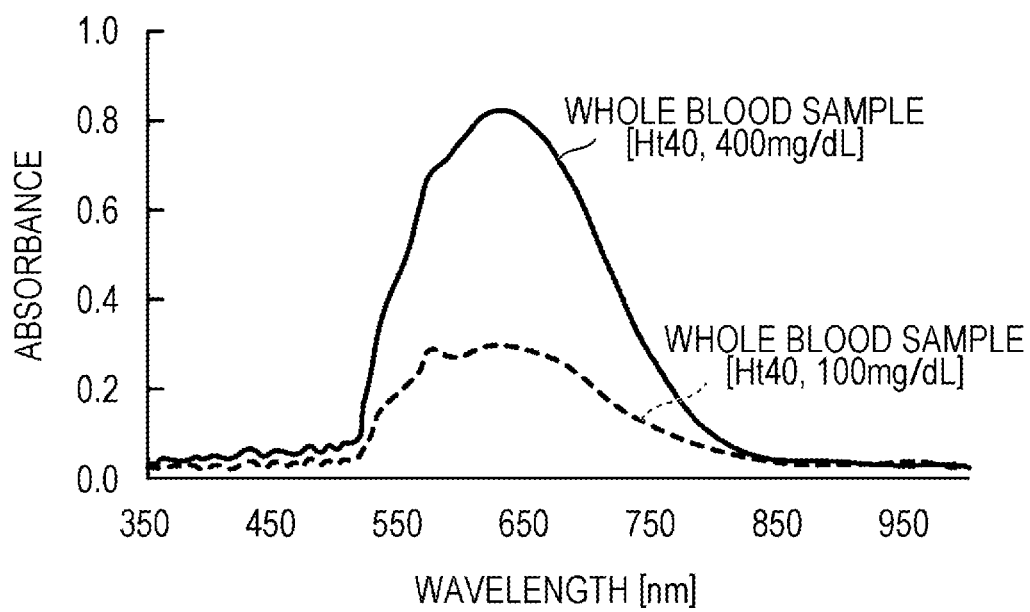
FIG. 6A is a diagram showing the spectra of a Ni²⁺ chelate compound of formazan produced when whole blood sample is spotted on a blood glucose meter sensor employing tetrazolium compound 1.
Figure 6B:
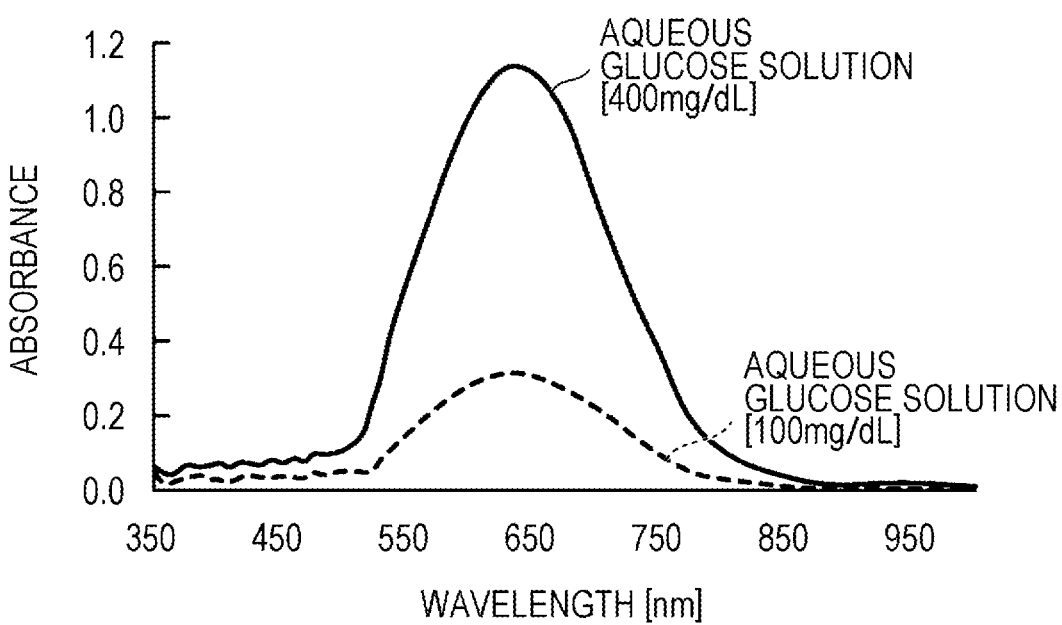
FIG. 6B is a diagram showing the spectra of a Ni²⁺ chelate compound of formazan produced when aqueous glucose solution is spotted on a blood glucose meter sensor employing tetrazolium compound 1.

Furthermore, a whole blood sample (Ht40, 400 mg/dL) (hematocrit value 40%, glucose concentration 400 mg/dL) was produced similarly to the whole blood sample (Ht40, 100 mg/dL). Separately, an aqueous glucose solution (100 mg/dL) and an aqueous glucose solution (400 mg/dL) were produced. For these samples, spectra were measured with a spectrophotometer after 9 seconds from the initiation of reaction in the same manner, using a blood glucose meter sensor to which the tetrazolium . . . compound 1 obtained in Example 1 was applied. The results are shown in FIG. 6. Meanwhile, FIG. 6A is a diagram showing the spectra obtained when the whole blood samples were submitted to the blood glucose meter sensor to which the tetrazolium compound 1 was applied. FIG. 6B is a diagram showing the spectra obtained when aqueous glucose solutions were submitted to the blood glucose meter sensor to which the tetrazolium compound 1 was applied.

As shown in FIG. 6, with the blood glucose meter sensor to which the tetrazolium compound 1 of Example 1 was applied, the absorbances of both the whole blood and the aqueous glucose solutions were higher than 0.2. Therefore, it can be seen that even in the case of using whole blood samples, the noise caused by colored components among the blood components is low, and biological components can be detected with high sensitivity.

Furthermore, an aqueous glucose solution (800 mg/dL) was produced.

Figure 7A:
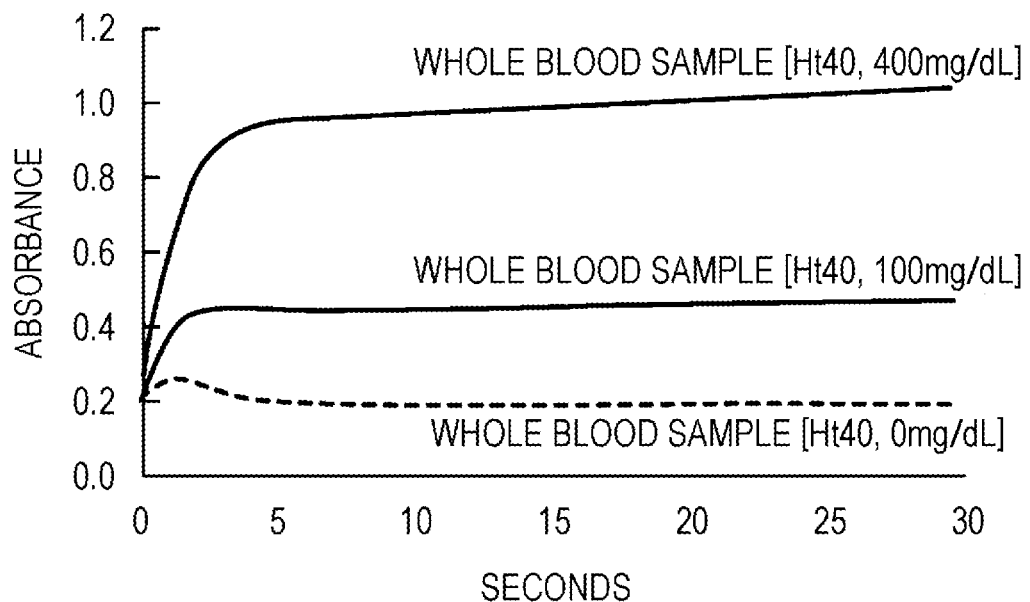
FIG. 7A is a diagram showing the relationship between the time taken from the initiation of measurement when a whole blood sample is spotted on a blood glucose meter sensor employing tetrazolium compound 1, and the absorbance of a Ni²⁺ chelate compound of formazan produced at the maximum absorption wavelength.
Figure 7B:
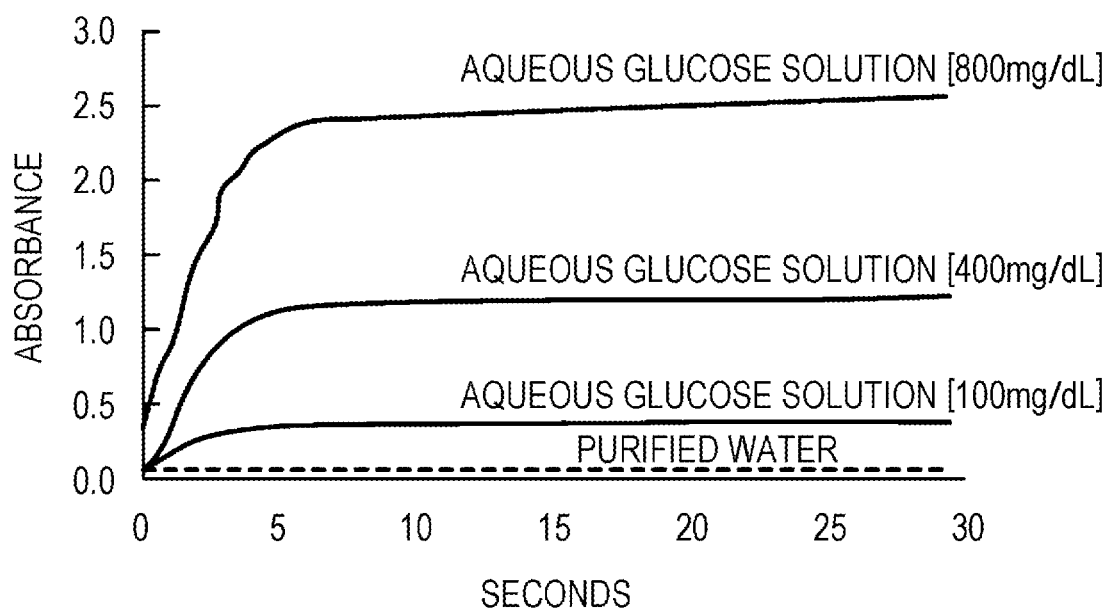
FIG. 7B is a diagram showing the relationship between the time taken from the initiation of measurement when an aqueous glucose solution is spotted on a blood glucose meter sensor employing tetrazolium compound 1, and the absorbance of a Ni²⁺ chelate compound of formazan produced at the maximum absorption wavelength.

Each sample of the whole blood sample (Ht40, 0 mg/dL), the whole blood sample (Ht40, 100 mg/dL), the whole blood sample (Ht40, 400 mg/dL), the aqueous glucose solution (100 mg/dL), the aqueous glucose solution (400 mg/dL), and the aqueous glucose solution (800 mg/dL) thus produced was measured with a blood glucose meter sensor to which the tetrazolium compound 1 of Example 1 was applied, and the relationship between the time taken from the initiation of reaction and the absorbance at 630 nm was determined. The results are shown in FIG. 7. FIG. 7A is a diagram showing the relationship between the time taken from the initiation of reaction when each of the whole blood samples was spotted on the blood glucose meter sensor to which the tetrazolium compound 1 was applied, and the absorbance at 630 nm. FIG. 7B is a diagram showing the relationship between the time taken from the initiation of reaction when each of the glucose solutions was submitted to the blood glucose meter sensor to which the tetrazolium compound 1 was applied, and the absorbance at 630 nm.

As shown in FIG. 7, in the blood glucose meter sensor to which the tetrazolium compound 1 of Example 1, color development was completed in 5 seconds for both the whole blood and the aqueous glucose solution, and the rate of color development and sensitivity were all satisfactory. Therefore, the reagent for biological component concentration measurement including the tetrazolium salt of the present disclosure can detect biological components rapidly with high sensitivity, even in the case of using whole blood samples.

Figure 8A:
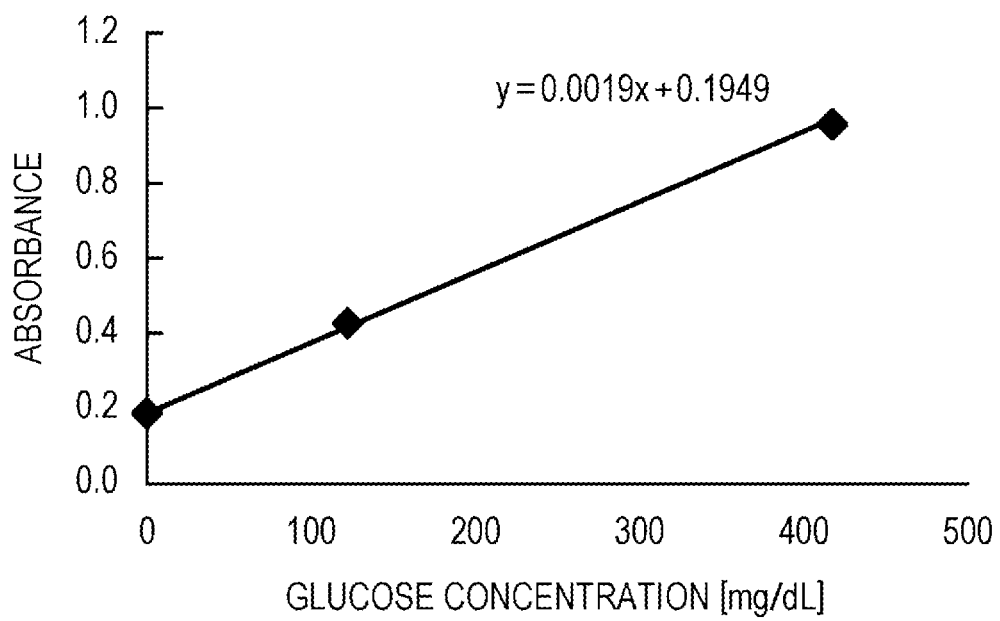
FIG. 8A is a graph showing the relationship between the glucose concentration obtainable when whole blood sample is spotted on a blood glucose meter sensor employing tetrazolium compound 1, and the absorbance of a Ni²⁺ chelate compound of formazan produced.
Figure 8B:
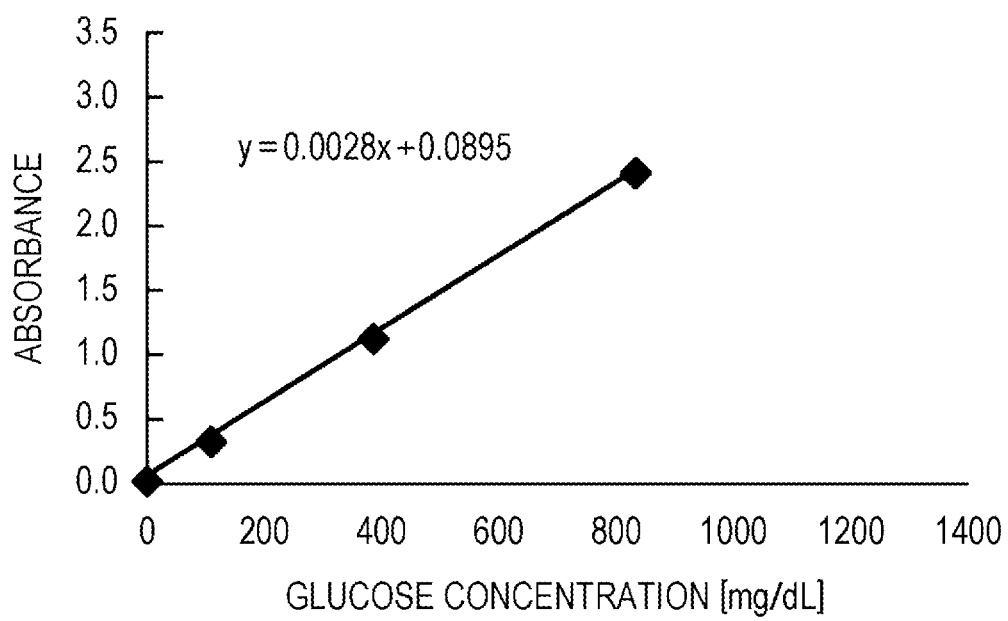
FIG. 8B is a graph showing the relationship between the glucose concentration obtainable when an aqueous glucose solution is spotted on a blood glucose meter sensor employing tetrazolium compound 1, and the absorbance of a Ni²⁺ chelate compound of formazan produced.

Furthermore, FIG. 8 presents a graph showing the relationship between the glucose concentration and the absorbance at the maximum absorption wavelength of a chelate compound of formazan and $Ni^{2+}$ when the whole blood sample (Ht40) and aqueous glucose solutions were measured with a blood glucose meter sensor. The measurement of the absorbance was carried out after 9 seconds from the initiation of reaction. FIG. 8A is a graph showing the relationship between the glucose concentration and the absorbance of a chelate compound of formazan and $Ni^{2+}$ when a whole blood sample was submitted to the blood glucose meter sensor to which the tetrazolium compound 1 was applied. FIG. 8B is a graph showing the relationship between the glucose concentration and the absorbance of a chelate compound of formazan and $Ni^{2+}$ when an aqueous glucose solution was submitted to the blood glucose meter sensor to which the tetrazolium compound 1 was applied.

As shown in FIG. 8, the absorbance and the blood sugar level exhibit a linear relationship (proportional relationship). From this, it is contemplated that the blood sugar level can be measured accurately by means of the absorbance.

From these findings, when the tetrazolium salt of the present disclosure, an oxidoreductase, and a transition metal compound are added to a biological sample, the quantity of color development is measured, and a calibration curve is produced based on this quantity of color development, the concentration of a biological component in a biological sample can be calculated accurately.

Evaluation Example 2: Evaluation with Blood Glucose Meter Sensor

1. Production of Ni Acetate and DSB 20 mM Solution 0.6 mL of a 0.5 M Ni acetate solution, 0.4 mL of RO water, and 8.7 mg of DSB (benzene-1,3-disulfonic acid) were mixed, and a Ni acetate-DSB solution was produced.

2. Production of Coating Liquid

To 87 µL of the Ni acetate-DSB solution, 4.7 µL of a 1 N NaOH solution, 30.3 µL of RO water, and 4.8 mg of each of the tetrazolium salts (compounds 17 to 20 and compound 1) were added, and the mixture was mixed. Furthermore, 4 µL of methanol and 1.7 mg of GDH-FAD were added to this liquid. This liquid was centrifuged, and the supernatant was used as a coating liquid.

3. Production of Reagent Piece

The coating liquid obtained as described above was applied on a PET film by an inkjet method, and a reagent ribbon was produced. This reagent ribbon was cut in the longitudinal direction (1.5 mm×3 mm), and this was designated as reagent piece 2.

4. Assembly of Blood Glucose Meter Sensor

FIG. 13A is a schematic diagram illustrating the assembly of a blood glucose meter sensor. In FIG. 13A, after the reagent piece 2 was obtained, a reagent-coated surface 3 of the reagent piece 2 was arranged to face downward, and the reagent piece 2 was installed on a PET film 5. Thus, a blood glucose meter sensor was assembled. In FIG. 13A, the reagent-coated surface 3 of the reagent piece 2 was arranged to face downward, and the reagent piece 2 was installed on double-sided tapes 4 disposed as spacers along the two edges of the PET film 5. Subsequently, a PET film 7 having the same shape as that of the PET film 5 was further attached by pressing on the reagent piece 2, and thereby, a sensor chip in which the blood flow channel at the inner surface had a stepped shape was obtained. FIG. 13B is a cross-sectional view in the longitudinal direction or the transverse direction of the sensor chip. Here, in FIG. 13B, regarding the flow channel length (L1), the flow channel width (W), and the flow channel thickness (t1) of the flow channel part, and the flow channel length (L2), the flow channel width (W), and the flow channel thickness (t2) of the reagent part (measuring unit) corresponding to a reagent-coated part, the dimensions indicated in the following table were used. In FIG. 13B, the flow channel of the chip is composed of a reagent part formed by a reagent-coated surface disposed thereon;

and a flow channel part formed from the portion of flow channel without the reagent-coated surface disposed thereon in the flow channel.

TABLE 4

| Flow channel part | | Reagent part (measuring unit) | |
|---|---|---|---|
| Length L1 | 9 mm | Length L2 | 3 mm |
| Width W | 1.5 mm | Width W | 1.5 mm |
| Thickness t1 | 0.13 mm | Thickness t2 | 0.05 mm |

The length L1 in a direction orthogonally intersecting the chip thickness direction (flow channel longitudinal direction) in the flow channel part is not particularly limited and can be selected as appropriate according to the purpose; however, the length L1 is preferably 5 to 10 mm. Here, when the length L1 is long, it is advantageous from the viewpoint that mounting (insertion) into a component analyzer is easy, and from the viewpoint that the intrusion of ambient light into the photometric part is reduced. When the length L1 is short, it is advantageous from the viewpoint that the amount of specimen can be reduced. Therefore, in the light of the balance between the ease of mounting (insertion) into a component analyzer, the influence of ambient light, and the amount of specimen, the upper limit and the lower limit of the length L1 are determined. The length L2 in a direction orthogonally intersecting the chip thickness direction (flow channel longitudinal direction) of the flow channel in the reagent part is not particularly limited and can be selected as appropriate according to the purpose; however, the length L2 is preferably 1 to 4 mm. Here, when the length L2 is long, it is advantageous from the viewpoint that since the area of the irradiation spot is taken to be large in the length direction, measurement can be carried out very accurately. Meanwhile, when the length L2 is short, it is advantageous from the viewpoint that the amount of specimen can be reduced. Therefore, in the light of the balance between the measurement accuracy and the amount of specimen, the upper limit and the lower limit of the length L2 are determined.

4. Evaluation of Produced Sensor

Aqueous glucose solution (n=3) or whole blood (n=5) was spotted on a sensor including each of the tetrazolium salts thus produced, and the blank spectrum, the color development spectrum, and the color development time course were checked using a fiber spectrophotometer. As the absorbance of the indicator compound, the absorbance at 650 nm was measured.

Figure 14:
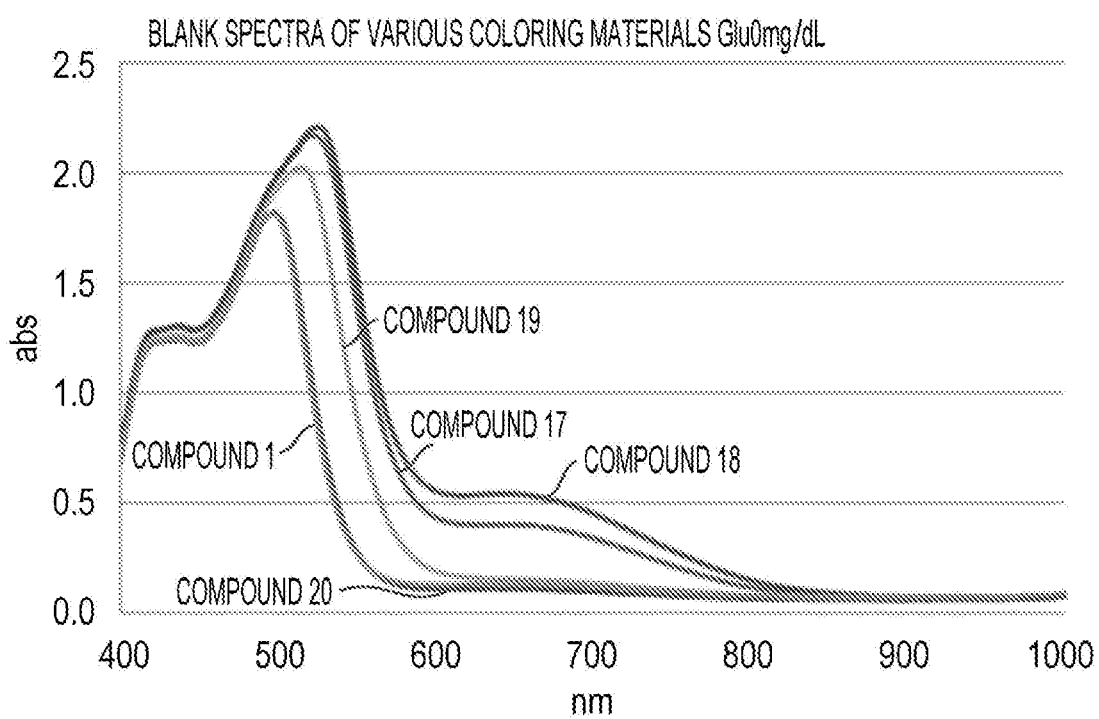
FIG. 14 is an absorbance spectrum (blank) of a blood glucose meter sensor having water spotted thereon.
Figure 15:
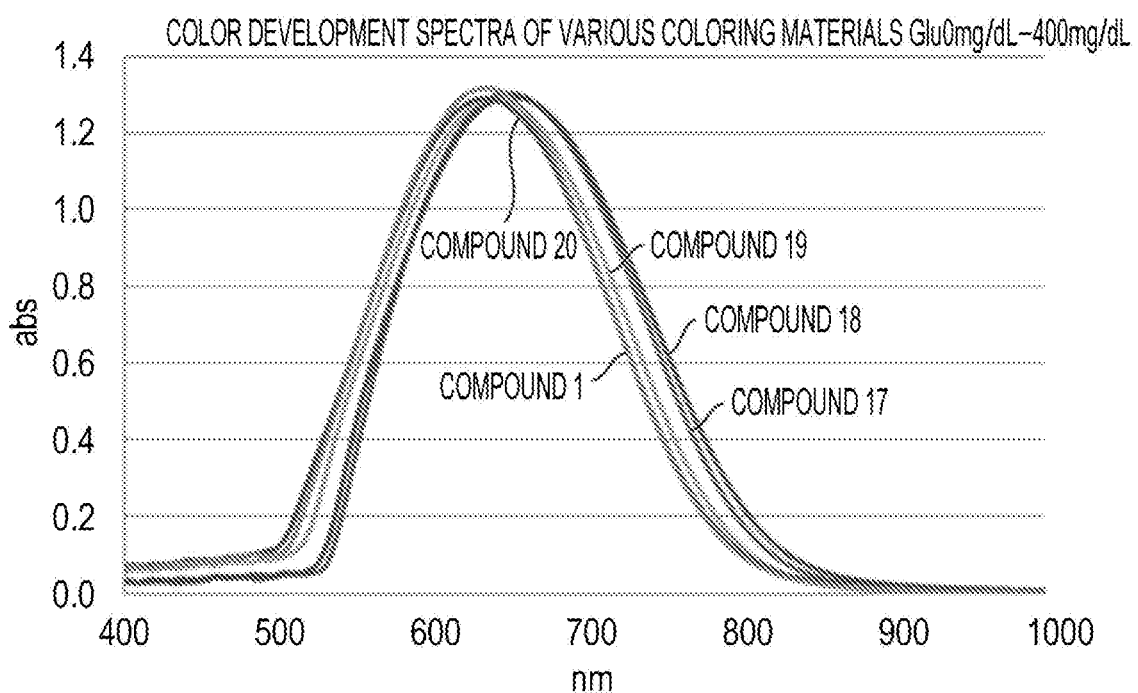
FIG. 15 shows a differential spectrum (meaning the net quantity of color development of glucose) obtained by subtracting the absorbance spectrum having water spotted thereon (FIG. 14) from the absorbance spectrum of the sensor having spotted thereon aqueous glucose solution at a glucose concentration of 400 mg/dL.

FIG. 14 presents the blank spectrum obtained at the time of spotting water having a glucose concentration of 0 mg/dL on the sensor, and FIG. 15 presents a differential spectrum obtained by subtracting the absorbance spectrum obtained by spotting water having a glucose concentration of 0 mg/dL (FIG. 14), from the absorbance spectrum of the sensor on which aqueous glucose solution having a glucose concentration of 400 mg/dL was spotted (the differential spectrum means the net quantity of color development of glucose).

Figure 16:
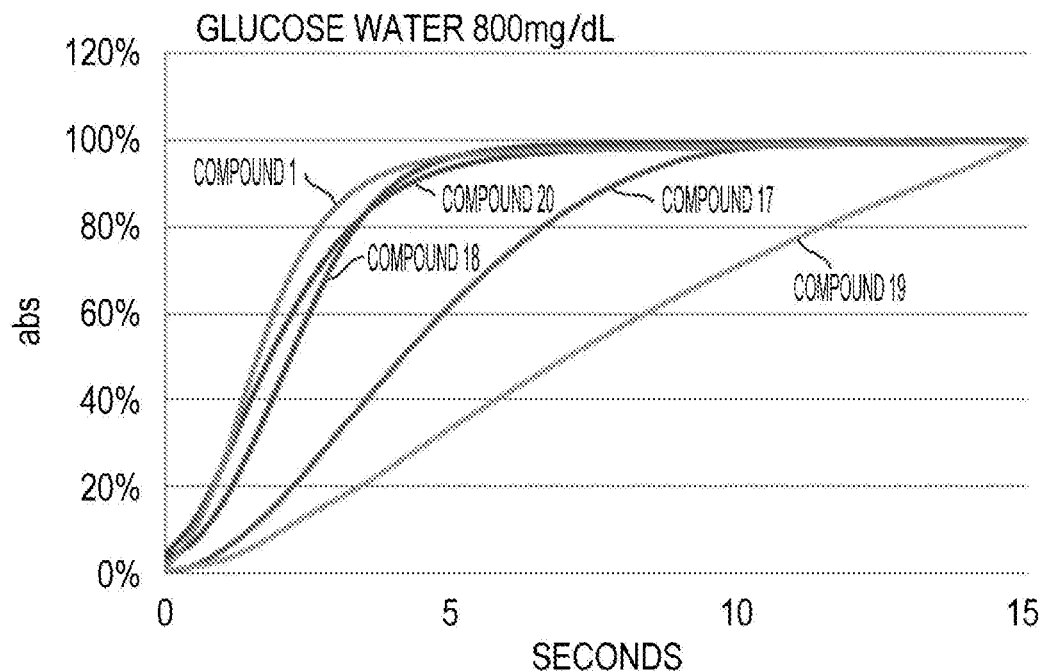
FIG. 16 is a diagram showing the relationship between the time taken from the initiation of measurement at the time of spotting an aqueous glucose solution (800 mg/dL) on blood glucose meter sensors employing various tetrazolium compounds, and the absorbance of a Ni²⁺ chelate compound of formazan produced at the maximum absorption wavelength (assuming the absorbance obtained 15 seconds after the initiation of reaction as 100%).
Figure 17:
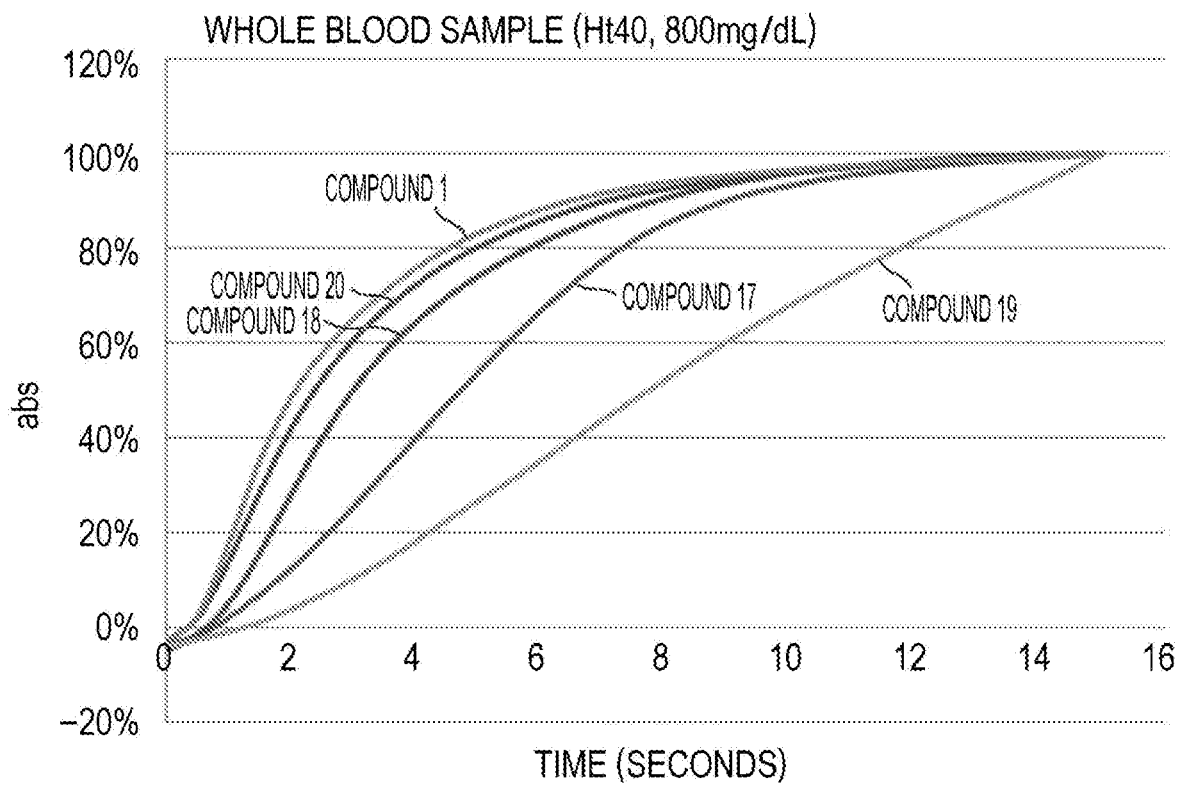
FIG. 17 is a diagram showing the relationship between the time taken from the initiation of measurement at the time of spotting a whole blood sample (Ht40, 800 mg/dL) (hematocrit value 40%, glucose concentration 800 mg/dL) on blood glucose meter sensor employing various tetrazolium compounds, and the absorbance of a Ni²⁺ chelate compound of formazan produced at the maximum absorption wavelength (assuming the absorbance obtained 15 seconds after the initiation of reaction as 100%).

In regard to the tetrazolium compound of the present disclosure, the time course of the net quantity of color development (measurement wavelength 650 nm) was measured for various substituents of the alkoxy group substituted at the 6-position (or the 5,6-position) of the benzothiazole ring. As a compensating wavelength that reflects the noise component originating from the blood sample, the absorbance at 900 nm was also measured. The time course of the quantity of color development was described as the proportion % at various times obtained when the absorbance after 15 seconds from the initiation of reaction was denoted as 100% with regard to the measurement wavelength 650 nm. The "net quantity of color development" is the net quantity of color development obtained by subtracting the absorbance obtained when blood having a blood sugar level of 0 mg/dL was reacted with the blood sugar level measuring reagent, from the absorbance obtained when blood having a desired blood sugar level (for example, 800 mg/mL) was reacted with the blood sugar level measuring reagent, with regard to blood samples having the same hematocrit value. Regarding the absorbances used for the calculation of the quantity of color development, a value obtained by subtracting the absorbance at 900 nm for compensating optical fluctuations, from the absorbance at 650 nm was used, in order to eliminate any optical fluctuations other than color development. The absorbance at 650 nm includes noise caused by the quantity of color development originating from glucose and the scattered light originating from blood cells. The absorbance at 900 nm reflects the quantity of the noise at 650 nm caused by the scattered light. FIG. 16 presents the absorbance spectrum obtainable when an aqueous glucose solution (800 mg/dL) was used, and FIG. 17 presents the absorbance spectrum obtainable when a whole blood sample (Ht40, 800 mg/dL) (hematocrit value 40%, glucose concentration 800 mg/dL) was used. From these results, it was confirmed that compound 17, compound 18, compound 19, and compound 20, in which the benzothiazole ring of compound 1 was substituted with various alkoxy groups at the 6-position or at the 5,6-position, can all be used as reagents for glucose measurement. Meanwhile, in Evaluation Examples 1 and 2, evaluation was made in consideration of the influence of the cell length in the measurement of transmitted light.

Evaluation Example 3: Estimation of Molar Extinction Coefficient

A measurement solution was produced in the same manner as described in the section for the evaluation of the chelation rate and the maximum absorption wavelength (λmax), using the tetrazolium compound 1 of Example 1.

Estimation of the molar extinction coefficient was carried out using the blood glucose meter sensor of FIG. 13. At this time, it is assumed that tetrazolium compound 1 reacts with glucose at a ratio of 1:1 (molar ratio). The concentration (mol/L) of β-glucose include in the spotted aqueous glucose solution was designated as x, and the value obtained by calculating the absorbance at 630 nm of the blood glucose meter sensor having aqueous glucose solution spotted thereon, to a value per 1 cm, was designated as y. The gradient of a straight line obtained at that time is designated as the molar extinction coefficient (calculated based on a glucose molecular weight 180.16, and a β-glucose ratio in the solution of 62%).

Figure 18:
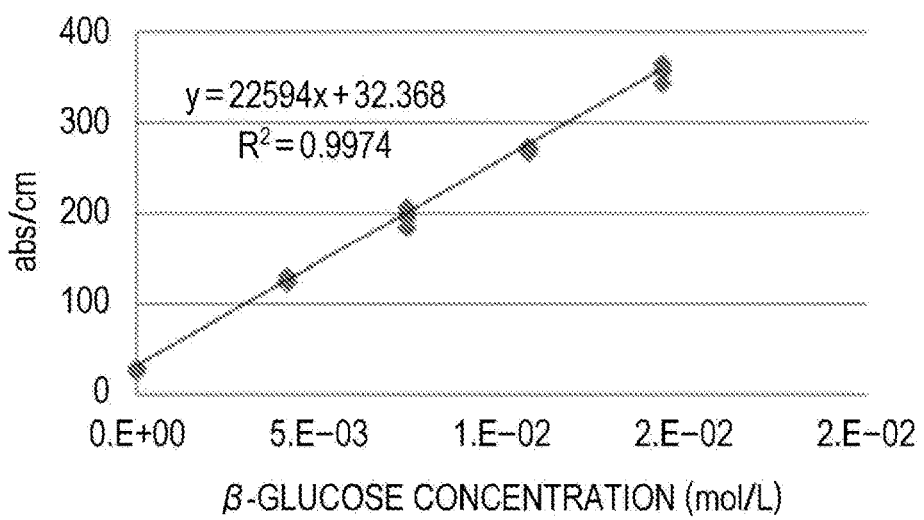
FIG. 18 is a graph obtained by plotting the β-glucose concentration (mol/L) on the x-axis, and plotting the absorbance at λmax=635 nm of a colored chelate compound of formazan and Ni²⁺ calculated to a value per 1 cm (abs/cm), on the y-axis.

FIG. 18 presents a graph obtained when the concentration (mol/L) of β-glucose was used as x value, and the absorbance at λmax=635 nm of colored chelate compound of formazan and $Ni^{2+}$, which was calculated into a value per 1 cm (abs/cm), was used as y value. From the graph, the molar extinction coefficient at λmax=635 nm of a colored chelate compound of formazan and $Ni^{2+}$ is c=22,594 L/mol·cm.

REFERENCE SIGNS LIST

1 REAGENT RIBBON; 2 REAGENT PIECE; 3 REAGENT-COATED SURFACE; 4 DOUBLE-SIDED TAPE; 5 PET FILM; 6 FLOW CHANNEL; 7 PET FILM; 10 BLOOD GLUCOSE METER; 12 SENSOR CHIP; 14 MEASURING UNIT; 16 APPARATUS MAIN BODY; 18 CHIP MAIN BODY; 20 CAVITY; 20a FRONT END PORT; 20b BASE END PORT; 22 LONG EDGE; 22a UPPER LONG EDGE; 22b LOWER LONG EDGE; 24 SHORT EDGE; 24a FRONT END EDGE; 24b BASE END EDGE; 26 REAGENT; 28 MEASURING OBJECT PORTION; 30 PLATE PIECE; 32 SPACER; 40 CASE; 42 CONTROL UNIT; 44 BOX BODY; 46 PHOTOMETRIC UNIT; 48 POWER SUPPLY BUTTON; 50 OPERATION BUTTON; 52 DISPLAY; 54 EJECTION LEVER; 56 EJECTION PIN; 56a ROD PORTION; 56b RECEPTOR; 58 INSERTION PORT; 58a INSERTION OPENING; 59 PORT FOR MEASUREMENT; 60 CHIP MOUNTING PART; 60a FLANGE PORTION; 62 WALL; 64 DEVICE ACCOMMODATING SPACE; 66 LIGHT GUIDE; 68 LIGHT EMITTING DEVICE; 70 LIGHT EMITTING UNIT; 72 LIGHT RECEIVING DEVICE; 74 LIGHT RECEIVING UNIT; 76 COIL SPRING.

What is claimed is:

1. A 2-substituted benzothiazolyl-3-substituted phenyl-5-substituted sulfonated phenyl-2H-tetrazolium salt represented by the following Formula (1):

[Chemical Formula 1]

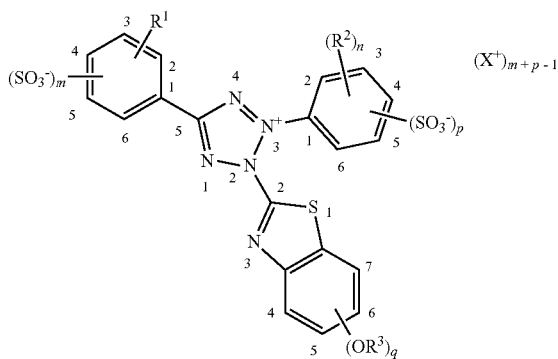

wherein in Formula (1), $R^1$ represents any one selected from the group consisting of a hydrogen atom, a hydroxyl group, a methoxy group, and an ethoxy group; $R^2$ represents any one selected from the group consisting of a nitro group, $-OR^4$, and a carboxyl group; $R^3$ represents a hydrogen atom, a methyl group, or an ethyl group, while at least one is a methyl group or an ethyl group; $R^4$ represents a methyl group or an ethyl group; m represents the number of sulfo groups ($-SO_3^-$) bonded to the phenyl group at the 5-position of the tetrazole skeleton, and is 1 or 2; n represents the number of $R^2$ bonded to the phenyl group at the 3-position of the tetrazole skeleton, and is an integer from 0 to 2; p represents the number of sulfo groups ($-SO_3^-$) bonded to the phenyl group at the 3-position of the tetrazole skeleton, and is 0 or 1; n+p is 1 or greater; q is 1 or 2; when q is 2, the $OR^3$'s are disposed adjacently to each other and may be bonded to each other and forma ring; and X represents a hydrogen atom or an alkali metal atom.

2. The tetrazolium salt of claim 1, wherein in Formula (1), m is 2.

3. The tetrazolium salt of claim 1, wherein in Formula (1), p is 1, or p is 0, with at least one $R^2$ is a carboxyl group.

4. The tetrazolium salt of claim 1, wherein in Formula (1), the phenyl group at the 5-position of the tetrazole skeleton is a phenyl group having a sulfo group ($-SO_3^-$) at the 2-position or the 4-position.

5. The tetrazolium salt of claim 1, wherein in Formula (1), at least one $-OR^3$ of the substituted benzothiazolyl group existing at the 2-position of the tetrazole skeleton is bonded to the 6-position of the benzothiazolyl group.

6. The tetrazolium salt of claim 1, wherein in Formula (1), n is 1 or 2, and at least one $R^2$ is an $-OR^4$ group.

7. The tetrazolium salt of claim 6, wherein the $-OR^4$ group is a methoxy group.

8. The tetrazolium salt of claim 1, wherein in Formula (1), p is 1, and the phenyl group at the 3-position of the tetrazole skeleton is a phenyl group having a sulfo group ($-SO_3^-$) existing at the 3-position or the 5-position.

9. The tetrazolium salt of claim 1, wherein in Formula (1), the phenyl group existing at the 3-position of the tetrazole skeleton is a 4-methoxy-3-sulfophenyl group, a 2-methoxy-5-sulfophenyl group, a 3-carboxy-4-methoxyphenyl group, or a 4-methoxy-5-sulfophenyl group.

10. A reagent for biological component concentration measurement, the reagent comprising the tetrazolium salt of claim 1.

11. The reagent for biological component concentration measurement of claim 10, the reagent further comprising a transition metal compound.

12. The reagent for biological component concentration measurement of claim 11, wherein the transition metal compound is a nickel compound.

13. The reagent for biological component concentration measurement of claim 10, wherein the reagent is used for the measurement of the concentration of glucose, cholesterol, neutral lipids, nicotinamide adenine dinucleotide phosphate (NADPH), nicotinamide adenine dinucleotide (NADH), or uric acid in blood or a body fluid.

14. A method for measuring a concentration of a biological component, the method comprising:
adding the 2-substituted benzothiazolyl-3-substituted phenyl-5-substituted sulfonated phenyl-2H-tetrazolium salt of claim 1, an oxidoreductase, and a transition metal compound to a biological sample;
measuring the quantity of color development; and
quantitatively determining the concentration of a biological component in the biological sample based on the quantity of color development.

15. The method of claim 14, wherein the biological component in the biological sample is glucose, cholesterol, neutral lipids, nicotinamide adenine dinucleotide phosphate (NADPH), nicotinamide adenine dinucleotide (NADH), or uric acid in blood or a body fluid.

16. A blood sugar level measuring reagent, comprising a 2-substituted benzothiazolyl-3-substituted phenyl-5-substituted sulfonated phenyl-2H-tetrazolium salt, GDH-FAD, and a transition metal ion.

17. A method for measuring blood sugar level, the method comprising adding a reagent of a 2-substituted benzothiazolyl-3-substituted phenyl-5-substituted sulfonated phenyl-2H-tetrazolium salt, GDH-FAD, and a transition metal ion to a sample.

* * * * *

UNITED STATES PATENT AND TRADEMARK OFFICE
CERTIFICATE OF CORRECTION

PATENT NO. : 10,851,094 B2  
APPLICATION NO. : 16/255535  
DATED : December 1, 2020  
INVENTOR(S) : Hiroya Sato Page 1 of 1

It is certified that error appears in the above-identified patent and that said Letters Patent is hereby corrected as shown below:

In the Claims

Claim 1, Column 65, Line 65:
Please delete "other and forma ring" and insert -- other and form a ring --.

Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*